US009061002B2

(12) United States Patent
Gómez Casado

(10) Patent No.: US 9,061,002 B2
(45) Date of Patent: Jun. 23, 2015

(54) **USE OF FLAGELLINS FROM THE GENUS *MARINOBACTER* AS VACCINATION ADJUVANTS**

(75) Inventor: Eduardo Gómez Casado, Madrid (ES)

(73) Assignee: INSTITUTO NACIONAL DE INVESTIGACIÓN TECNOLOGÍA AGRARIA Y ALIMENTARIA (INIA), Madrid (ES)

( * ) Notice: Subject to any disclaimer, the term of this patent is extended or adjusted under 35 U.S.C. 154(b) by 83 days.

(21) Appl. No.: 13/576,764

(22) PCT Filed: Feb. 2, 2010

(86) PCT No.: PCT/ES2010/070052
§ 371 (c)(1),
(2), (4) Date: Oct. 24, 2012

(87) PCT Pub. No.: WO2011/095649
PCT Pub. Date: Aug. 11, 2011

(65) Prior Publication Data
US 2013/0202627 A1 Aug. 8, 2013

(51) Int. Cl.
| | | |
|---|---|---|
| *A61K 39/02* | (2006.01) | |
| *A61K 39/39* | (2006.01) | |
| *A61K 39/112* | (2006.01) | |
| *A61K 39/145* | (2006.01) | |
| *C07K 14/195* | (2006.01) | |
| *C07K 14/255* | (2006.01) | |
| *C12N 15/86* | (2006.01) | |
| *A61K 39/00* | (2006.01) | |

(52) U.S. Cl.
CPC ............. *A61K 39/39* (2013.01); *A61K 39/0275* (2013.01); *A61K 39/145* (2013.01); *A61K 2039/55516* (2013.01); *C07K 14/195* (2013.01); *C07K 14/255* (2013.01); *C12N 15/86* (2013.01); *C12N 2710/14043* (2013.01); *C12N 2760/16134* (2013.01)

(58) Field of Classification Search
USPC .......... 424/185.1, 190.1, 192.1, 203.1, 234.1, 424/258.1, 278.1, 282.1; 530/350
See application file for complete search history.

(56) References Cited

FOREIGN PATENT DOCUMENTS

| | | |
|---|---|---|
| WO | 2005070455 A1 | 8/2005 |
| WO | 2005077408 A2 | 8/2005 |
| WO | 2009079564 A2 | 6/2009 |

OTHER PUBLICATIONS

Honko et al (Infect. Immun. 2006. 74(2): 1113-1120).*
Chothia et al (The EMBO Journal, 1986, 5/4:823-26.*
Greenspan et al (Nature Biotechnology 7: 936-937, 1999).*
Mikayama et al. (Nov. 1993. Proc.Natl.Acad.Sci. USA, vol. 90 : 10056-10060.*
Rudinger et al. (Jun. 1976. Peptide Hormones. Biol.Council. pp. 5-7).*
Green, D., et al.; "*Marinobacter algicola* DG893 Flagellin Domain Protein," Database UniProt [Online]; XP002598765, Database accession No. A6F1F9; Abstract, Jan. 2010.
Lee, Shee Eun, et al.; "A Bacterial Flagellin, *Vibrio vulnificus* FlaB, Has a Strong Mucosal Adjuvant Activity to Induce Protective Immunity," Infection and Immunity, 2006, pp. 694-702, vol. 74, No. 1.
Velan, Baruch.; "Reversal of Signal-mediated Cellular Retention by Subunit Assembly of Human Acetylcholinesterase," The Journal of Biological Chemistry, 1994, pp. 22719-22725, vol. 269.
Database WPI Week 200418, Thomson Scientific, London, 2004-181218, XP002598767 & CN 1458161A, Nov. 26, 2003, Abstract.
Green, David H., et al.; "*Marinobacter algicola* sp. nov., isolated from laboratory cultures of paralytic shellfish toxin-producing dinoflagellates," International Journal of Systematic and Evolutionary Microbiology, 2006, pp. 523-527, vol. 56.
McSorley, S. J., et al.; "Bacterial Flagellin Is an Effective Adjuvant for CD4 + Cells In Vivo 1," The Journal of Immunology, pp. 3914-3919, vol. 169 2002.
Green, D., et al.; "*Marinobacter algicola* DG893 Flagellin," Database UniProt [Online]; XP002598764, Database accession No. A6F1G0; Abstract, Jan. 2010.
International Search Report, Sep. 28, 2010.

* cited by examiner

*Primary Examiner* — Jennifer Graser
(74) *Attorney, Agent, or Firm* — Tristan A. Fuierer; Moore & Van Allen, PLLC

(57) ABSTRACT

Use of flagellins from the genus *Marinobacter* as vaccine adjuvants. This invention is based on the use of two recombinant flagellins, F and FR, from the species *Marinobacter algicola* (DG893T strain), as vaccine adjuvants capable of developing a specific immune response, against peptides or proteins fused to said flagellins, or administered unfused jointly with the flagellins. This invention also describes new combined vaccination strategies, based on the two *Marinobacter algicola* flagellins and the *Salmonella typhimurium* flagellin.

6 Claims, 9 Drawing Sheets

USE OF FLAGELLINS FROM THE GENUS *MARINOBACTER* AS VACCINATION ADJUVANTS

CROSS-REFERENCE TO RELATED APPLICATIONS

Figure 1:
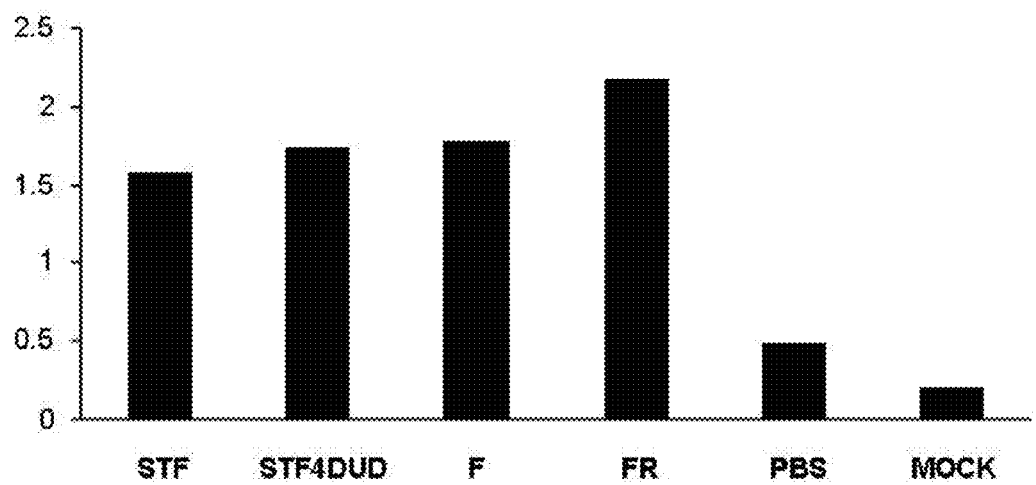

This application is filed under the provisions of 35 U.S.C. §371 and claims the priority of International Patent Application No. PCT/ES2010/070052 filed on 2 Feb. 2010 entitled "Use of Flagellins from the Genus *Marinobacter* as Vaccination Adjuvants" in the name of Eduardo Gómez Casado, which is hereby incorporated by reference herein in its entirety.

FIELD OF THE INVENTION

This invention may be ascribed to the technical field of medicine, preferably within the branch of immunology, as well as the pharmaceutical industry, specifically the technological field of vaccine development.

This invention relates to the use of recombinant bacterial flagellins from the species *Marinobacter algicola* as vaccine adjuvants capable of developing a specific immune response against peptides or proteins, fused or unfused, toward said flagellins. This invention also relates to vaccines that combine bacterial flagellins from the species *Marinobacter algicola* and bacterial flagellins from the species *Salmonella typhimurium*.

BACKGROUND

Flagellin is the generic name for the main structural protein that makes up bacterial flagella. They are cylindrical structures of variable length (approx. 530 nm) and about 21 nm in diameter [1]. The flagella are observed in both Gram-positive and Gram-negative bacteria; they are structures of variable length that allow bacteria to move in liquid media. In addition to being formed by flagellin, the bacterial flagellum is also composed of many other proteins that intervene in the assembly, the interaction with the cell's external envelopes, or participate in chemotactic processes.

The X-ray diffraction study of the structure of bacterial flagellin from the genus *Salmonella* has made it possible to increase the knowledge about its function and biological implications [1, 2]. Flagellin may play a significant role in bacterial pathogenesis [3] and has been defined as a prototype of "pathogen-associated molecular patterns" (PAMPs), since it is capable of activating the innate immune system through interaction with specific receptors [4], [5].

Most bacterial flagellins are recognised by the "Toll-like-5" (TLR5) receptor, which is located in the membrane of epithelial cells and immune system cells: monocytes, T lymphocytes, NK cells and immature dendritic cells. TLR5 is one of the receptors in the "Toll-like" family which have the capacity to interact with PAMPs [6], each TLR having the capacity to recognise specific PAMPs [7]. Once the flagellin is bound to TLR5, a signal transduction cascade is initiated through MyD88 (Myeloid differentiation primary response gene 88) in order to mediate in the production of cytokines necessary for the development and regulation of an innate and adaptive immune response in the host [8-10]. The binding of *Salmonella* flagellin to TLR5 is very specific and acts with a high affinity, at concentrations as low as $8.5 \times 10^{-10}$ M [11]. On the other hand, it is also well-known that some bacterial flagellins are not capable of activating the immune system when a natural infection occurs, that is, they do not bind to the TLR5 receptor to induce the inflammatory response [12]. The immunological escape of these flagellins has been circumscribed to bacteria from the alpha and epsilon subgroups (*Helicobacter pylori*, for example), whereas responding flagellins, those which activate the host's immune system, would belong to the beta and gamma groups [12]. The molecular and functional analysis of non-responding flagellins, those which do not activate the host's immune system, made it possible to define a specific interaction region with the TLR5 receptor in flagellins, this specific region being that comprised between amino acids 89-96 of the flagellin protein sequences [13].

Most current vaccines are composed of the antigen of interest and adjuvants [14], [15]. Although adjuvants improve the immune response, they may also cause adverse secondary effects, as in the case of Freund's complete adjuvant [16], [17], or even in the case of other adjuvants approved by the FDA or the EMEA. In order to solve said problem associated with the manufacturing of vaccines and improve the effectiveness thereof, the *Salmonella typhimurium* flagellin has been used as a vaccine adjuvant, since it has been shown that this flagellin, in transcriptional fusion with peptides or proteins, induces a humoural and cellular immune response, innate and adaptive, toward them, which is very rapid and potent. Some of the vaccines based on the *Salmonella* flagellin have been aimed against cholera [18], influenza [19], 20[20], plague (*Yersinia pestis*) [21], 22[22], malaria (*Plasmodium falciparum*) [23] and the West Nile virus [24].

The *Salmonella* bacterium is currently classified into the species *S. bongori* and *S. enterica* [25]. Most *Salmonella* that infect mammals and birds belong to *S. enterica*, which is divided into six subspecies (enterica, salamae, arizonae, diarizonae, houtenae, indica), with approximately 2,000 serotypes defined on the basis of differences in the composition of lipopolysaccharides (LPS) and flagellar antigens [25]. Some serotypes are host-exclusive, such as *S. typhi* (humans) and *S. pullorum* (birds), and others are primarily adapted to specific hosts, such as *S. cholerae-suis* (porcines), *S. abortus-ovis* (ovines), and *S. dublin* (bovines) [25].

Infection by *Salmonella* causes the appearance of cellular and humoural immunity against various antigens of said bacteria. One of these antigens is flagellin, as has been shown in various studies performed on people of Caucasian origin in Denmark and the United States [26]-[27]. In a random population study in the U.S., 30% of the subjects had antibodies against the Salmonella flagellin [28]. On the other hand, the response capacity toward flagellin in bacterial infections is diverse, and high responders and low responders to re-immunisation with flagellin may be found [27]; these results are attributed to certain Gm genotypes of flagellin [27]. Likewise, birds and other animals are very susceptible to infection by enteric Salmonella [29]. Therefore, infections by Salmonella occur in different species and countries, which indicates the scope of these pathologies; for this reason, control programmes for humans have been implemented for many years, and it is a mandatory declaration disease in bovines, ovines and caprines. All these data indicate that a significant percentage of the population that is infected presents antibodies against the *Salmonella* flagellin.

Most variants of *Salmonella* have two types of different genes that encode flagellin, although only the flagellin from one of these genes is expressed at each time. The bacterium is capable of alternating the expression of the two flagellins, called phase-1 flagellin and phase-2 flagellin. The operon that controls the synthesis of phase-1 flagellin also encodes a repressor of the synthesis of phase-2 flagellin, and vice-versa. The change mechanism from phase 1 to phase 2 in the synthesis of flagellin may be a consequence of the bacteria's attempt to avoid cellular immunity.

A recent study [30] has provided much clarification about those aspects related to the immunogenicity of the *Salmonella typhimurium* flagellin. Mice that are immunised with the flagellin on successive occasions produce antibodies that neutralise the TLR5-flagellin interaction capacity. These antibodies are primarily aimed at the hypervariable region (HPVR) of the flagellin. The obtainment of various flagellins the hypervariable regions whereof are eliminated to different extents has made it possible to observe that these modified flagellins preserve their capacity to interact with TLR5, and react to a lesser extent with a hyperimmune mouse serum obtained from immunisation with wild-type flagellin. However, the reactivity of a hyperimmune mouse serum following immunisation with a version of flagellin without HPVR between the wild-type flagellin and others without HPVR is very similar, which indicates the presence of antibodies that neutralise the conserved regions of the flagellins, including the regions of interaction with TLR5. On the other hand, the complete elimination of the HPVR prevents the modified flagellin from normally initiating the production of inflammatory cytokines (CCL20 and CXCL2) at the systemic level, although this alteration in the flagellin does not cause the same effect at the mucous membrane level [30]. That is, when this flagellin is injected, it fails to produce inflammatory mediators, but it has an adequate behaviour when it is applied to mucous membranes. In summary, all these data indicate that:

1. The function of flagellin may be neutralised by pre-existing antibodies against the wild-type flagellin (complete). The antibodies generated against a wild-type flagellin are primarily directed against the hypervariable region.

2. If the hypervariable region is completely eliminated, the anti-flagellin antibodies generated recognise the conserved domains, which include the region of interaction with TLR5. Therefore, it would be preferable not to eliminate the hypervariable region, since it is more immunodominant and, thus, the antibodies generated are not directed against the region of interaction with TLR5.

3. Different versions of flagellin without HPVR fragments are functional upon activating TLR5 at the mucous membrane level, but do not work equally well at the systemic level, except for one of the versions obtained, which has an HPVR part, and does behave like the wild-type flagellin. However, it may be neutralised, albeit to a lesser extent than the wild type, by serum antibodies that have reacted against the wild-type flagellin [30].

All of the above suggests that a vaccine based on the *Salmonella* flagellin capable of activating the immune system in all its forms could not be used repeatedly because the pre-existing antibodies would neutralise the potential thereof.

For all these reasons, a very significant advance would be made in the development and application of flagellin-based vaccines if other flagellins were available that induce the same activation of the innate immune system and escape the immunological response triggered against the *Salmonella* flagellins.

In this regard, this invention has surprisingly discovered that vaccines based on flagellins from marine bacteria of the species *Marinobacter algicola* are equally effective, or even more so, than vaccines based on *Salmonella* flagellins. Since *Marinobacter algicola* bacteria are marine bacteria, prior infection of non-aquatic organisms is very unlikely. To this date, it has not even been determined whether said bacteria are capable of infecting aquatic organisms. Thus far, 12 species of *Marinobacter* have been recognised, isolated from different sources, such as crude oil extraction ducts in off-shore platforms [31], coastal thermal waters [32], hot springs [33] and Antarctic waters [34], saline soils [35] and marine sediments [36]. In laboratory studies of different algae, three bacterial strains from the genus *Marinobacter* have been isolated, which have been called *Marinobacter algicola*, two of them originating in the Yellow Sea off the coast of Korea (DG893T and DG1136) and one from the Vigo Estuary in Galicia (GC21V) [37].

As in the case of *Salmonella*, the *Marinobacter algicola* bacterium has two genes that encode two flagellins. Thus, this invention describes the use of the two recombinant flagellin protein sequences from the species *Marinobacter algicola* (DG893T strain), called flagellin F and flagellin FR, capable of inducing and developing a specific immune response by themselves, without the aid of other adjuvants, which indicates that said flagellins are capable of appropriately interacting with the TLR5 receptor, triggering the immunological response. But this invention also shows that *Marinobacter algicola* flagellins F and FR may fuse to peptides, proteins or vaccinal antigens, or be jointly administered with said peptides and proteins, without being fused thereto, and developing a specific immune response.

Moreover, it shows the limited cross-reactivity between the flagellins from the genus *Marinobacter* described in this invention and the *Salmonella* flagellin. This limited reactivity between flagellins from both species is due to the relatively low sequence homology between both flagellins (33%-36%). It is worth noting that the low cross-reactivity between said flagellins represents an advantage in the effectiveness of vaccines based on *Marinobacter* flagellins, since, as previously discussed, there could be partial neutralisation of vaccines based on the *Salmonella* flagellin in subjects that have been infected by or had previous contact with *Salmonella*, or have been previously immunised with the *Salmonella* flagellin. However, prior immunity against bacteria from the genus *Marinobacter* is unlikely, since it is a marine bacterium that is not known to infect human beings or other organisms, and the likelihood of contact with non-marine organisms to produce an immunological response therein is very low.

We also describe different combined vaccination strategies based on the use of the two *Marinobacter* flagellins described in this invention and the *Salmonella typhimurium* flagellin. In this regard, subjects that have had prior contact with *Salmonella* could be vaccinated using the *Marinobacter* flagellins (F and FR), whereas in subjects not previously exposed to *Salmonella* a different strategy could be used: in the first place, they could be immunised with a vaccine based on the *Marinobacter* flagellin and, subsequently, another vaccine based on the *Salmonella* flagellin could be applied. This would enhance the use of these vaccines for multiple antigens without reducing the efficacy thereof due to cross-seroneutralisation between the flagellins.

DESCRIPTION OF THE INVENTION

Brief Description of the Invention

This invention is based on the use of two recombinant flagellins, from the species *Marinobacter algicola* (DG893T strain), as vaccine adjuvants capable of developing a specific immune response against peptides or proteins fused to said flagellins, or jointly administered without being fused. We also define combined vaccination strategies based on the two *Marinobacter algicola* flagellins and the *Salmonella typh-*

*imurium* flagellin, as well as the synthesis methods for the vaccine adjuvants that comprise the flagellins described in this invention.

DESCRIPTION OF THE FIGURES

FIG. 1. Levels of IL-8 measured by ELISA following the stimulation of CACO-2 cells in the presence of different *Marinobacter* flagellins (Flagellins F and FR) and *Salmonella typhimurium* flagellins (Flagellins STF and STF4DUD). STF4DUD: purified recombinant *Salmonella typhimurium* flagellin (STF) fused to 4 tandem copies of the DUD epitope (DUD is a gene sequence that encodes a dynein-binding peptide). As negative controls, the cells have been cultured in the presence of PBS and in the absence of PBS (MOCK). The figure represents the arithmetic mean of the levels of IL-8 in two measurements performed by means of ELISA. The results are expressed as the optical density measured at 490 nm (Y-axis).

FIG. 2. Level of IgG antibodies (1/100 dilution) against the DUD sequence induced by the different flagellins and measured by means of ELISA. The data represented correspond to the arithmetic means of all the animals (n=5) in each group. The results are expressed as the optical density measured at 405 nm (Y-axis) of the two measurements performed. STF4DUD: represents the levels of IgG obtained in the serum of mice immunised by subcutaneous route with the purified recombinant *Salmonella typhimurium* flagellin (STF) fused to 4 tandem copies of the DUD epitope. F4DUD: represents the levels of IgG obtained in the serum of mice immunised by subcutaneous route with the purified recombinant *Marinobacter* flagellin (F) fused to 4 tandem copies of the DUD epitope. FR4DUD: represent the levels of IgG obtained in the serum of mice immunised by subcutaneous route with the purified recombinant *Marinobacter* flagellin (FR) fused to 4 tandem copies of the DUD epitope. F4DUD-in: represents the levels of IgG obtained in the serum of mice immunised by intranasal route with the purified recombinant *Marinobacter* flagellin (F) fused to 4 tandem copies of the DUD epitope. 4DUD: corresponds to the negative control of the experiment. They represent the levels of IgG obtained in the serum of mice immunised by subcutaneous route with 4 tandem copies of the DUD epitope, without flagellins.

FIG. 3. Titre of IgG antibodies (1/12,800 dilution) against the DUD sequence induced by the different flagellins and measured by means of ELISA. The results are expressed as the optical density measured at 405 nm (Y-axis) of the two measurements performed. STF4DUD: represents the levels of IgG obtained in the serum of mice immunised by subcutaneous route with the purified recombinant *Salmonella typhimurium* flagellin (STF) fused to 4 tandem copies of the DUD epitope. F4DUD: represents the levels of IgG obtained in the serum of mice immunised by subcutaneous route with the purified recombinant *Marinobacter* flagellin (F) fused to 4 tandem copies of the DUD epitope. FR4DUD: represents the levels of IgG obtained in the serum of mice immunised by subcutaneous route with the purified recombinant *Marinobacter* flagellin (FR) fused to 4 tandem copies of the DUD epitope. F4DUD-in: represents the levels of IgG obtained in the serum of mice immunised by intranasal route with the purified recombinant *Marinobacter* flagellin (F) fused to 4 tandem copies of the DUD epitope. 4DUD: corresponds to the negative control of the experiment. They represent the levels of IgG obtained in the serum of mice immunised by subcutaneous route with 4 tandem copies of the DUD epitope, without flagellins. 3×4DUD: is another negative control of the experiment. It represents three times the optical density value of the 4DUD tetrapeptide. This optical density value serves as a cut-off line that all the sera should exceed in order to conclude that they are capable of producing a potent immune response.

FIG. 4. Titre of IgG antibodies against sequence 4M2-2009 induced by fusion flagellin FR-4M2-2009 and measured by means of ELISA. 4M2-2009: corresponds to the 4 tandem copies of the M2-2009 epitope, pertaining to the influenza virus A/Castilla-La-Mancha/GP13/2009/H1N1 pandemic strain. The results are expressed as the optical density measured at 405 nm (Y-axis) of the two measurements performed. The X-axis represents the degree of dilution of the sera. R1, R2, R3 and R4 represent the sera of the mice inoculated with flagellin FR-4M2-2009. C1, C2, C3 and C4 represent the sera of the control mice that were inoculated with the M2-2009 peptide in PBS.

FIG. 5. Titre of IgG antibodies that recognise *Salmonella typhimurium* flagellin STF, and which are present in sera against the *Salmonella typhimurium* flagellin (serum group A), in sera against *Marinobacter* flagellin F (serum group B) and in an anti-4DUD serum (serum D1). The optical density measured at 405 nm (Y-axis) of the two measurements performed is represented. The X-axis represents the serum from each subject from lower to greater dilution (see legend).

FIG. 6. Titre of IgG antibodies that recognise *Marinobacter* flagellin F, and which are present in sera against *Marinobacter* flagellin F (serum group B), in sera against the *Salmonella typhimurium* flagellin (serum group A) and in an anti-4DUD serum (serum D1). The optical density measured at 405 nm (Y-axis) of the two measurements performed is represented. The X-axis represents the serum from each subject from lower to greater dilution (see legend).

FIG. 7. Titre of IgG antibodies that recognise *Salmonella typhimurium* flagellin STF, and which are present in a serum against *Salmonella typhimurium* flagellin STF (serum A1), in sera against *Marinobacter* flagellin FR (serum group C) and in an anti-4DUD serum (serum D1). The optical density measured at 405 nm (Y-axis) of the two measurements performed is represented. The X-axis represents the serum from each subject from lower to greater dilution (see legend).

FIG. 8. Titre of IgG antibodies that recognise *Marinobacter* flagellin FR, and which are present in sera against *Marinobacter* flagellin FR (serum group C), in sera against the *Salmonella typhimurium* flagellin (serum group A) and in an anti-4DUD serum (serum D1). The optical density measured at 405 nm (Y-axis) of the two measurements performed is represented. The X-axis represents the serum from each subject from lower to greater dilution (see legend).

FIG. 9. Titre of IgG antibodies that recognise *Marinobacter* flagellin F, and which are present in sera against *Marinobacter* flagellins F and FR. The optical density measured at 405 nm (Y-axis) of the two measurements performed is represented. The brick-shaped bars represent the mouse sera that contain antibodies against flagellin FR (*Marinobacter*). The black bars and the bars with oblique lines, respectively, represent the sera from 2 different mice that contain antibodies against flagellin F (*Marinobacter*).

DETAILED DESCRIPTION OF THE INVENTION

This invention describes the use of the flagellins called F and FR from the species *Marinobacter algicola* (DG893T strain) as vaccine adjuvants and vaccines per se, capable of developing a specific immune response against peptides, proteins or vaccinal antigens fused to the flagellins, or administered unfused jointly with these flagellins. It also defines new combined vaccination strategies based on the two *Marino-* bacter algicola flagellins and the *Salmonella typhimurium* flagellin (STF), in addition to the synthesis methods for the vaccine adjuvants that comprise the flagellins described in this invention.

In order to show the vaccinal and adjuvant capacity, in vitro and in vivo, of *Marinobacter* flagellins F and FR, as compared to *Salmonella typhimurium* flagellin STF, in this invention we have used different versions of the gene sequences that encode the recombinant proteins of the above-mentioned flagellins. On the one hand, the gene sequences that encode the recombinant flagellins by themselves (F, FR and STF) and, on the other hand, the gene sequences that encode the recombinant flagellins fused to different epitopes. An epitope is understood to be a protein sequence of a macromolecule that is recognised by the immunological system, specifically by antibodies, B cells or T cells, which, moreover, is capable of generating an immunological response.

In this invention, the gene sequence that encodes a dynein-binding peptide (DUD) and the gene sequence that encodes a peptide used as a vaccine target for the influenza or flu virus have been used as epitopes. The DUD peptide is formed by the gene sequence responsible for the binding of the p54 protein (the protein responsible for the binding of the African swine fever (ASF) virus to the host cell) [38] to a gene sequence specific for the dynein light chains, DLC8. The amino acid sequence responsible for the binding of the p54 protein to dynein light chain DLC8, is made up of a 13-amino-acid epitope (SEQ ID NO: 13) of said p54 protein [39]. The peptide used as the vaccine target against the influenza virus is the peptide known as the ectodomain of the M2 protein (M2e). The M2 protein has a significant role in the viral cycle of the influenza virus. It forms an ion channel that allows for the entry of protons into the virus, thereby reducing the pH and allowing for dissociation of the protein from the M1 matrix of the NP ribonucleoprotein, in order to finally discharge the entire content into the cytoplasm of the infected cell. The M2e region is especially conserved. In this invention, the M2e region of the flu virus A/Castilla-La-Mancha/GP13/2009/H1N1 pandemic strain (M2-2009), which encodes a 24-amino-acid peptide (SEQ ID NO: 27), has been selected. Antibodies against epitopes SEQ ID NO: 13 and SEQ ID NO: 27 do not appear in animals following immunisation with the recombinant p54 and M2 proteins, respectively, in the absence of adjuvants; they only appear in animals that have been hyperimmunised against the ASF virus and against the influenza virus, respectively; therefore, we may affirm that these epitopes are good models for testing the vaccinal and adjuvant capacity of *Marinobacter* flagellins F and FR as compared to *Salmonella typhimurium* flagellin STF.

Previous studies have shown that the immune response developed against four tandem copies of an epitope is greater than that developed against a single copy of this epitope [20]. For this reason, in order to demonstrate the vaccinal-adjuvant capacity of *Marinobacter* flagellins, this invention has used the recombinant proteins of flagellin F by itself (SEQ ID NO: 20), of flagellin F bound to a histidine tail and to a KDEL sequence (SEQ ID NO: 2), of flagellin F fused to four tandem copies of the modified DUD peptide, leading to fusion flagellin F F4DUD (SEQ ID NO: 24) and the above-mentioned fusion flagellin F F4DUD bound to a histidine tail and to a KDEL sequence (SEQ ID NO: 6). Moreover, in this invention we have used the recombinant proteins of flagellin FR by itself (SEQ ID NO: 22), of flagellin FR fused to a histidine tail and to a KDEL sequence (SEQ ID NO: 4), of flagellin FR fused to four tandem copies of the modified DUD peptide, leading to fusion flagellin FR FR4DUD (SEQ ID NO: 26) and of said fusion flagellin FR FR4DUD bound to a histidine tail and to a KDEL sequence (SEQ ID NO: 8). We have also used the recombinant proteins of flagellin FR fused to four tandem copies of the M2-2009 peptide, leading to fusion flagellin FR FR4M2-2009 (SEQ ID NO: 31) and fusion flagellin FR FR4M2-2009 bound to a histidine tail and to a KDEL sequence (SEQ ID NO: 29). Finally, we have used the *Salmonella typhimurium* flagellin (STF) by itself (SEQ ID NO: 15), flagellin STF fused to four tandem copies of the modified DUD peptide bound to a histidine tail and to a KDEL sequence, leading to fusion flagellin STF STF4DUD (SEQ ID NO: 10). The modified DUD peptide SEQ ID NO: 14) is different from the unmodified DUD peptide (SEQ ID NO: 13) in that it contains an amino acid sequence from the binding region of p54 that is amplified with five additional amino acids at the 3'-end and with seven additional amino acids at the 5'-end, in order that the recognition of the epitopes for the development of the humoural response be as similar as possible to the response induced by the complete protein under physiological conditions.

Thus, this invention analyses the functionality and the adjuvant-vaccinal capacity of *Marinobacter algicola* flagellins F and FR (DG893T strain) in different versions: F (SEQ ID NO: 2), FR (SEQ ID NO: 4), F4DUD (SEQ ID NO: 6), FR4DUD (SEQ ID NO: 8) and FR4M2-2009 (SEQ ID NO: 29). Flagellins F4DUD (SEQ ID NO: 6) and FR4DUD (SEQ ID NO: 8) are flagellins F and FR with 4 tandem copies of the DUD peptide fused to the 3'-end thereof. Flagellin FR4M2-2009 (SEQ ID NO: 29) is flagellin FR with 4 tandem copies of the M2-2009 peptide fused to the 3'-end thereof. In order to compare the activity and the function of the *Marinobacter* flagellins, we have also obtained the *Salmonella typhimurium* flagellin in the following versions: STF (SEQ ID NO: 15) and STF4DUD (SEQ ID NO: 10), the latter being a fusion flagellin that carries 4 tandem copies of the DUD peptide fused to the 3'-end thereof.

The genes of *Marinobacter algicola* flagellins F (SEQ ID NO: 1) and FR (SEQ ID NO: 3) used in this invention were chemically synthesised from their primary DNA sequence (Genbank: NZ_ABCP01000018.1). On the other hand, the gene of *Salmonella typhimurium* flagellin STF was obtained from the DNA of *Salmonella typhimurium* by PCR amplification with specific primers for sequences SEQ ID NO: 11 and SEQ ID NO: 12. All the sequences of the flagellins by themselves: F, FR and STF, and of the fusion flagellins with the epitope, either the DUD epitope or the M2-2009 epitope, in tandem: F4DUD, FR4DUD, STF4DUD and FR4M2-2009, include, at the 3'-end or the 5'-end thereof, a histidine tail in order that the recombinant proteins subsequently expressed, either by means of the baculovirus-insect cell system, or the transformation of bacteria with the plasmids carrying said sequences, are easier to purify by means of chromatography, although any method or system recognised in the state of the art that facilitates the subsequent purification of said recombinant proteins may be used. Furthermore, all the sequences of the flagellins described in this invention include the "KDEL" amino acid sequence, which serves to retain the proteins in the endoplasmic reticulum, thereby being less exposed to degradation, and ultimately increasing the amount of the protein expressed. In the same manner as discussed above, any amino acid sequence capable of preventing the degradation of the recombinant proteins obtained may be used. In the particular case of this invention, the production of the flagellins of interest F, F4DUD, FR, FR4DUD, FR4M2-2009, STF and STF4DUD is increased.

Figure 2:
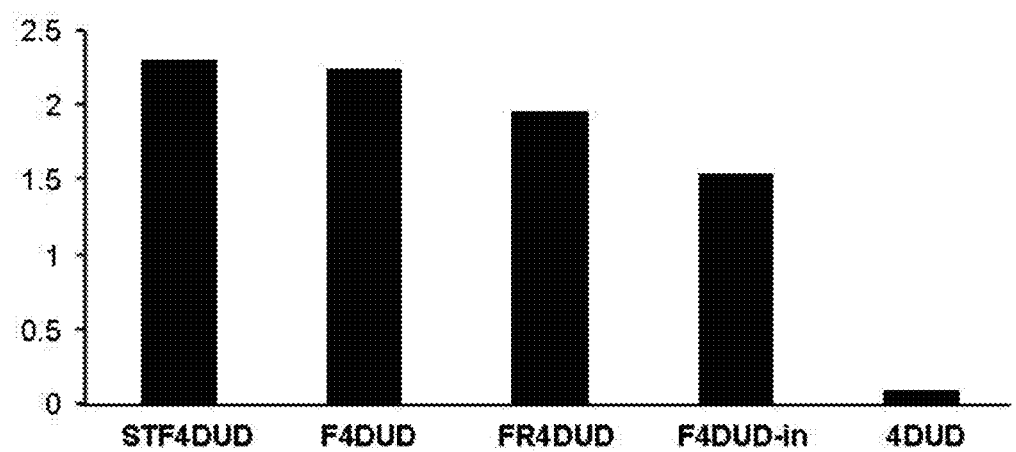
Figure 3:
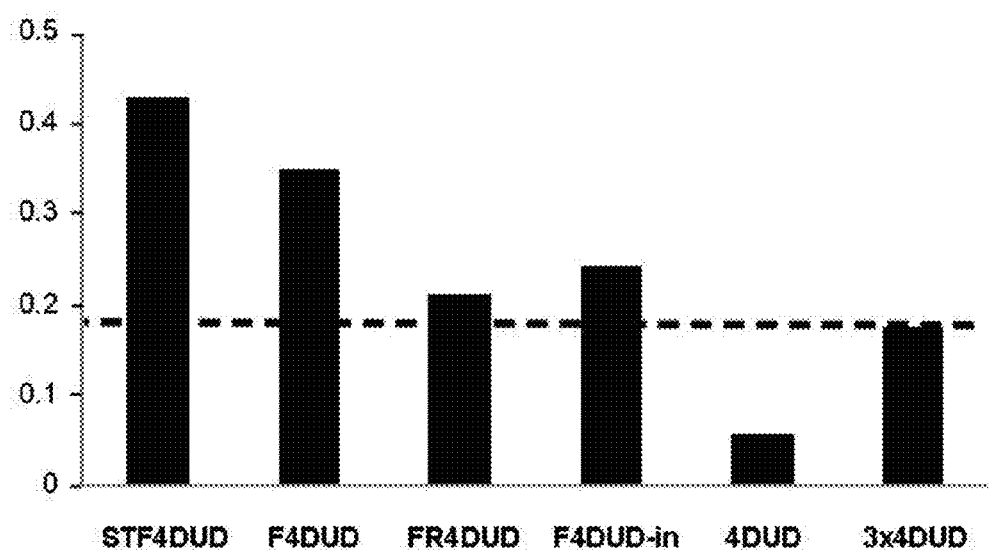
Figure 4:
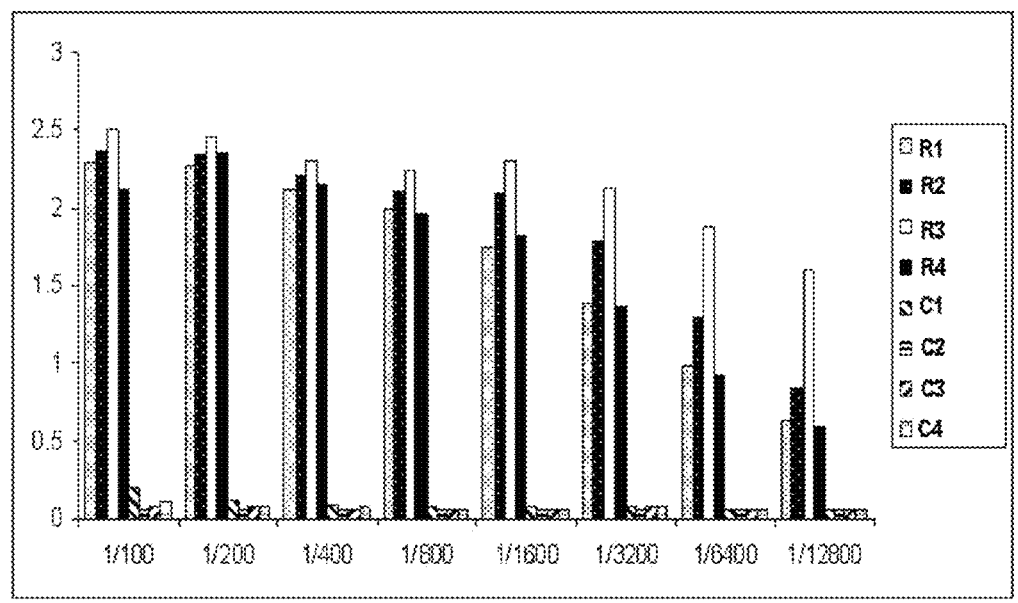

This invention demonstrates the capacity of the *Marinobacter* flagellins to evoke an immune response similar to that triggered by *Salmonella typhimurium* flagellin STF, both at the in vitro level, being capable of inducing the release of cytokine IL-8 to the extracellular medium in cell cultures in the presence of flagellins F and FR (FIG. 1), and in vivo; and similar levels of IgG anti-DUD antibodies (FIG. 2) are obtained in serum samples from mice immunised by subcutaneous (sc) or intranasal (in) route with the purified *Marinobacter* fusion flagellins, F4DUD and FR4DUD, as compared to the mice immunised with *Salmonella typhimurium* fusion flagellin STF4DUD (FIGS. 2 and 3). Likewise, high levels of IgG anti-4M2-2009 antibodies were obtained in serum samples from mice immunised by subcutaneous route with purified fusion flagellins FR-4M2-2009, as compared to the levels obtained in the sera of control mice immunised with the M2-2009 peptide in PBS (FIG. 4). Therefore, these results show that the *Marinobacter* flagellins appropriately interact with the TLR5 receptor, in a similar manner to the *Salmonella typhimurium* flagellin.

The amino acid sequences of *Marinobacter* flagellins F and FR, which interact with TLR5, triggering the activation of the immune system, are different from those of *Salmonella typhimurium* flagellins. These amino acid sequences of interaction between the TLR5 receptor and flagellins FR and F are defined by SEQ ID NO: 16 and SEQ ID NO: 17, respectively. In this invention, we have also shown that the interaction sequence of flagellin F amplified with additional amino acids at the 3'-region (SEQ ID NO: 18) is still capable of binding to the TLR5 receptor and triggering the activation of the immune system. Using the BLAST and CLUSTAL W biocomputer programmes [40-42], we have analysed the homology between the protein sequences of *Marinobacter algicola* (DG893T Strain) flagellins F (SEQ ID NO: 20) and FR (SEQ ID NO: 22) and of *Salmonella typhimurium* flagellin STF (SEQ ID NO: 15), showing that:

a) When the complete sequences of all the above-mentioned flagellins are analysed, the homology between F and FR is 63%, the homology between F and STF is 33%, and that between FR and STF is 36%.

b) When the most conserved regions are analysed (excluding the central part, which is hypervariable), which correspond to the first 170 amino acids of the amino-terminal area and to the last 90 amino acids (carboxyl-terminal area) of the above-mentioned flagellins, the homology between F and FR is 78%, the homology between F and STF is 55%, and that between FR and STF is 57%.

In this invention, we have also analysed the cross-reactivity of the antibodies against the *Salmonella typhimurium* flagellin as compared to the *Marinobacter* flagellins, and vice-versa, as well as the cross-reactivity between both *Marinobacter* flagellins (FIGS. 5-9). The purpose of said analysis was to study the presence of antibodies capable of recognising different flagellins, following a standard immunisation process, although in this invention we have used higher doses of vaccinal flagellins than necessary (30 μg), in order to develop an effective immune response with said molecules. As previously discussed, the antibodies generated against the flagellin used for the immunisation (for example, *Salmonella typhimurium*) could be specific for regions that do not interact with TLR5 or for regions that are important for this recognition. In sum, the appearance of these antibodies may neutralise the functionality of new administrations of vaccinal flagellin, which makes the repeated use of the flagellin of the same organism as a vaccine more complicated. On the other hand, the absence of recognition of the antibodies generated by the flagellin from the species *Salmonella typhimurium* as compared to the *Marinobacter* flagellins, and vice-versa, would make it possible to establish new vaccination strategies, which would solve said problem.

Figure 7:
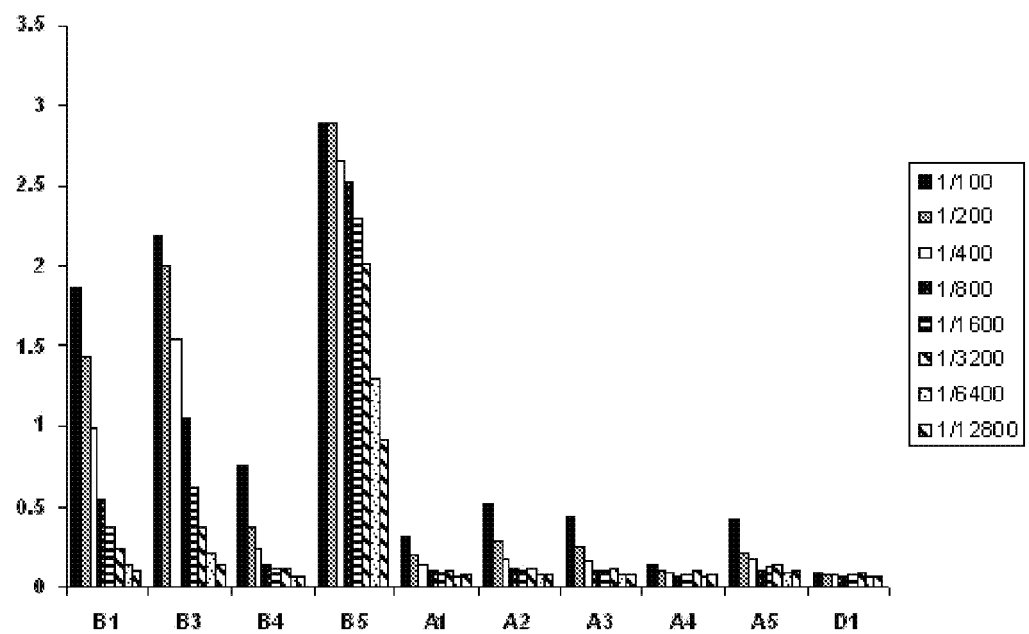

The results shown in this invention indicate that, in general, the antibodies against *Marinobacter* flagellin F slightly recognise *Salmonella typhimurium* flagellin STF (FIG. 5), and the serum that is most positive in anti-F antibodies recognises the *Salmonella* flagellin (STF) between 16 and 32 times less than a positive serum. The sera against flagellin FR also slightly react toward flagellin STF, although the most positive serum recognises flagellin STF 32 times less than a positive control (FIG. 7).

On the other hand, the antibodies against the *Salmonella typhimurium* flagellin (STF) slightly recognise flagellin F (FIG. 6), and there is practically no recognition of *Marinobacter* flagellin FR (FIG. 8) at a 1/100 dilution. The sera against the *Salmonella typhimurium* flagellin have a titre of IgG greater than 1/12,800, which could reach 1/25,600, which indicates that the scant cross-reactivity between the *Marinobacter* (especially FR) and the *Salmonella typhimurium* flagellins could be explained by the low sequence homology, which is 33%-36%. However, the anti-F and anti-FR antibodies exhibit cross-reactivity with *Marinobacter* flagellins FR and F, respectively. This fact may be explained by the degree of homology between flagellins F and FR, which is 63% of the complete structure, and 78% of the structure that represents the most conserved areas, as mentioned above.

This invention describes a new vaccination strategy based on the use of *Marinobacter* flagellins F and FR. On the one hand, it proposes the use of vaccines based on flagellins F or FR in subjects that have been in contact with *Salmonella typhimurium* and present antibodies against the *Salmonella* flagellin due to previous infections or prior immunisation with the *Salmonella typhimurium* flagellin; these subjects may be vaccinated with at least one effective dose of one of the *Marinobacter* flagellins bound to or administered jointly with a specific epitope in order to generate immunity and, on the other hand, be vaccinated with at least another effective dose of the other *Marinobacter* flagellin bound to or administered jointly with an epitope different from the preceding one, thereby generating double immunity against two different epitopes. On the other hand, it proposes that subjects which have not been previously exposed to *Salmonella*, nor immunised with the flagellin thereof, could first be immunised with at least one effective dose of a vaccine based on any of the *Marinobacter* flagellins (F or FR) and, subsequently, receive at least another effective dose based on the *Salmonella* flagellin, preferably based on the *Salmonella typhimurium* flagellin, and vice-versa; that is, first be immunised with at least one effective dose of a vaccine based on the *Salmonella* flagellin, preferably *Salmonella typhimurium* and, in the second place, be immunised with at least one effective dose of a vaccine of any of the *Marinobacter* flagellins (F or FR). Another vaccination strategy to be considered in subjects that do not have prior immunity against the *Salmonella* flagellin, preferably *Salmonella typhimurium*, is to immunise them with at least one effective dose of a vaccine based on this flagellin, subsequently immunise them with at least one effective dose of a vaccine based on one of the *Marinobacter* flagellins bound to or administered jointly with a specific epitope, in order to generate immunity, and, on the other hand, immunise them with at least one effective dose of a vaccine based on the other *Marinobacter* flagellin bound to or administered jointly with an epitope different from the preceding one, thereby generating triple immunity against three differente epitopes. The order of administration of the effective doses of the vaccines to the subjects is interchangeable: they may first be vaccinated with the vaccines based on the *Marinobacter* flagellins and, in the second place, with the vaccine based on the *Salmonella typhimurium* flagellin, or vice-versa. The vaccination strategies described in this invention enhance the use of the vaccines for multiple antigens without reducing the efficacy thereof due to potential cross-seroneutralisation between flagellins.

Thus, one of the objects of this invention relates to a vaccine adjuvant that comprises at least one flagellin from the genus *Marinobacter*, preferably from the species *Marinobacter algicola*.

In another preferred embodiment, the vaccine adjuvant of the invention may be fused to at least one epitope capable of generating an immunological response, preferably 4 tandem copies. In another preferred embodiment of the invention, the epitopes capable of generating an immunological response are not fused to the vaccine adjuvant, but may be jointly administered therewith, without being fused thereto.

In another preferred embodiment, the vaccine adjuvant of the invention comprises at least one amino acid sequence selected from: SEQ ID NO: 16, SEQ ID NO: 17 and SEQ ID NO: 18.

In another preferred embodiment, the vaccine adjuvant of the invention is characterised in that it contains, at least, one amino acid sequence selected from: SEQ ID NO: 2, SEQ ID NO: 4, SEQ ID NO: 6, SEQ ID NO: 8, SEQ ID NO: 20, SEQ ID NO: 22, SEQ ID NO: 24, SEQ ID NO: 26, SEQ ID NO: 29 or SEQ ID NO: 31, or one amino acid sequence encoded by: SEQ ID NO: 1, SEQ ID NO: 3, SEQ ID NO: 5, SEQ ID NO: 7, SEQ ID NO: 19, SEQ ID NO: 21, SEQ ID NO: 23, SEQ ID NO: 25, SEQ ID NO: 28 or SEQ ID NO: 30.

Another object of this invention relates to a vaccine that comprises at least one vaccine adjuvant as described above, optionally comprising other vaccine adjuvants; it may additionally contain an epitope capable of generating an immunological response, but not fused to the vaccine adjuvant.

Another object of this invention relates to the method of synthesising vaccine adjuvants, characterised in that they comprise at least one bacterial flagellin from the genus *Marinobacter*, characterised by the following:

a) Selecting at least one of the gene sequences that encode flagellins from the genus *Marinobacter*.

b) Cloning at least one of the gene sequences from the preceding step in an expression vector.

c) Generating modified organisms by the insertion of the vector from the preceding step.

d) Growing the organisms modified in the preceding step under suitable conditions to favour the expression of at least one of the sequences included in the vector.

e) Isolating at least one of the proteins expressed by the organisms carrying the expression vector from the preceding step.

In another preferred embodiment, the method of the invention is characterised in that the gene sequences that encode the flagellins are preferably selected from SEQ ID NO: 1, SEQ ID NO: 3, SEQ ID NO: 5, SEQ ID NO: 7, SEQ ID NO: 19, SEQ ID NO: 21, SEQ ID NO: 23, SEQ ID NO: 25, SEQ ID NO: 28 and SEQ ID NO: 30.

In a preferred embodiment, the method of the invention is characterised in that at least one epitope capable of generating a specific immunological response, preferably 4 tandem copies, may be added to the gene sequences that encode the flagellins from the genus *Marinobacter*.

In another preferred embodiment, the method of the invention is characterised in that a gene sequence that encodes a peptide capable of facilitating the isolation or purification of the flagellin may be added to the gene sequences of the flagellins from the genus *Marinobacter*. This sequence may be added to both the 3'-end and the 5'-end, and is preferably added to the 3'-end.

In another preferred embodiment, the method of the invention is characterised in that the sequence that encodes a peptide sequence capable of facilitating the isolation or purification of the flagellin is preferably a histidine tail.

In another preferred embodiment, the method of the invention is characterised in that a gene sequence that encodes a peptide capable of preventing the degradation of the flagellin, preferably a sequence that encodes the KDEL peptide, may also be added to the gene sequences of the flagellins from the genus *Marinobacter*.

In another preferred embodiment, the method of the invention is characterised in that the expression vector used is preferably selected from those comprised in the following strains: CECT 7633, CECT 7634, CECT 7635 and CECT 7636.

In another preferred embodiment, the method of the invention is characterised in that the modified organisms are preferably selected from viruses and bacteria.

In another preferred embodiment, the method of the invention is characterised in that the viruses are preferably baculoviruses.

In another preferred embodiment, the method of the invention is characterised in that the viruses generated by the method of the invention are preferably Baculoviruses and are used to transfect mammalian or insect cells, preferably insect cells.

Another object of this invention relates to an expression vector characterised in that it comprises any of sequences SEQ ID NO: 1, SEQ ID NO: 3, SEQ ID NO: 5, SEQ ID NO: 7, SEQ ID NO: 19, SEQ ID NO: 21, SEQ ID NO: 23, SEQ ID NO: 25, SEQ ID NO: 28 and SEQ ID NO: 30, and is preferably selected from any of those comprised by the following strains: CECT 7633, CECT 7634, CECT 7635 and CECT 7636.

Another object of this invention are the viruses transformed with any of the expression vectors mentioned above, preferably baculoviruses.

Another object of this invention are the bacteria transformed with any of the expression vectors mentioned above, preferably bacteria from the *E. coli* DH5α strain.

Another object of this invention are the cells infected with the viruses transformed with the vectors described above, and may be mammalian or insect cells.

Another object of this invention relates to the use of any of the sequences selected from: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 29, SEQ ID NO: 30 and SEQ ID NO: 31, for the manufacturing of vaccine adjuvants and/or vaccines.

Another object of this invention is a vaccination method that comprises administering to a subject at least one effective dose of a vaccine that comprises the vaccine adjuvants of the invention.

In a preferred embodiment, the vaccination method of the invention is characterised in that it additionally comprises administering to a subject at least a second effective dose of a vaccine that comprises, at least, a *Salmonella typhimurium* flagellin as a vaccine adjuvant, before or after the administration of the dose of any of the vaccines described in this invention.

The effective dose is the minimum dose capable of producing the desired effect. In the case of this invention, an effective dose is understood to be the minimum dose capable of inducing a specific immunological response in those subjects whereto a vaccine is administered. Different doses of each of the vaccines may be administered until immunity is achieved in the subject.

Deposit of Microorganisms in Accordance with the Budapest Treaty

The plasmid-carrying strains of *Eschericia coli* DH5α used in this invention were deposited in the Spanish Type Culture Collection (CECT), located at the Research Building of the University of Valencia, Campus Burjassot, Burjassot 46100 (Valencia, Spain) on 26 Nov. 2009, with the following deposit nos.:

CECT 7633: pFastBac-FR4DUD-HisKdel; contains the gene sequence that encodes the recombinant *Marinobacter* flagellin FR, bound to 4 tandem copies of the DUD epitope.

CECT 7634: pFastBac-F4DUD-HisKdel; contains the gene sequence that encodes the recombinant *Marinobacter* flagellin F, bound to 4 tandem copies of the DUD epitope.

CECT 7635: pFastBac-F-HisKdel; contains the gene sequence that encodes the recombinant *Marinobacter* flagellin F.

CECT 7636: pFastBac-FR-HisKdel; contains the gene sequence that encodes the recombinant *Marinobacter* flagellin FR.

They all additionally comprise the gene sequence that encodes a histidine tail and the KDEL peptide.

The objective of the examples explained below is to illustrate the invention without limiting the scope thereof.

EXAMPLE 1

Obtainment and Purification of the Recombinant Flagellin Sequences

In this invention, we study the functionality and the adjuvant-vaccinal capacity of *Marinobacter algicola* flagellins F and FR (DG893T strain). In order to compare the activity and the function of the *Marinobacter* flagellins, we have also obtained and used *Salmonella typhimurium* flagellin STF.

The F and FR genes of the *Marinobacter algicola* flagellins were chemically synthesised (MrGene, Germany) from the primary DNA sequences of both flagellins, SEQ ID NO: 19 and SEQ ID NO: 21, respectively. Subsequently, a sequence that encodes a histidine tail was added to said sequences (in order to facilitate the purification of the recombinant protein obtained) and a sequence that encodes for the KDEL peptide was also added (it prevents the degradation of the recombinant protein obtained). On the other hand, starting from the *Salmonella typhimurium* DNA (GenBank: AY649721), the flagellin gene was obtained by polymerase chain reaction amplification with specific primers, SEQ ID NO: 11 and SEQ ID NO: 12. The PCR conditions were: 5 min at 96° C.; 30 20-second cycles at 96° C., 30 s at 60° C., 1 min and 45 s at 72° C.; and a final 10-min cycle at 72° C.

As previously discussed, all the flagellin gene sequences include, at the 3'-ends (although they may also be included at the 5'-end), a sequence that encodes a histidine tail, subsequently used for the purification of said proteins following the expression thereof, and a region that encodes the "KDEL" peptide, which serves to retain proteins in the endoplasmic reticulum, thereby leaving the recombinant protein less exposed to degradation and increasing the amount of protein expressed. Moreover, all the flagellin DNA gene sequences used included restriction targets (Bam HI and Xba I) in order to be subsequently cloned in the pFastbac plasmid. The *Eschericia coli* DH5α strain was used for the transformation and growth of the different plasmids carrying the flagellin sequences of the invention. Said strains were deposited at the Spanish Type Culture Collection with deposit numbers CECT 7633 (pFastBac-FR4DUD-HisKdel), CECT 7634 (pFastBac-F4DUD-HisKdel), CECT 7635 (pFastBac-F-HisKdel) and CECT 7636 (pFastBac-FR-HisKdel).

The recombinant flagellin proteins were obtained by two different mechanisms; on the one hand, with recombinant baculoviruses, using the commercial "Bac-to-Bac® Baculovirus system" (Invitrogen, USA), following the manufacturer's instructions, and subsequently transfecting insect cells (used as a biofactory) with said recombinant baculoviruses, in order to obtain the recombinant flagellins. The other mechanism used to obtain the recombinant flagellins was to obtain a recombinant plasmid specific for the transformation of BL21(DE3) pLysS bacteria, following the manufacturer's recommendations (Invitrogen, United Kingdom). Subsequently, the expression of the recombinant flagellin proteins in said bacteria was induced by adding IPTG (isopropyl b-D-thiogalactoside, an artificial inducer of the lacZ gene, a determinant of β-galactosidase) to the bacterial culture medium.

In order to obtain the recombinant flagellins from the recombinant baculoviruses generated, the latter were grown until a titre of $10^8$ pfu/ml was obtained. Subsequently, Sf21 and Sf9 insect cells from the species *Spodoptera frugiperda*, which grow in monolayer and in suspension, respectively, were transfected with said recombinant baculoviruses for 72 hours. Once this time had elapsed, the recombinant flagellins were purified by affinity chromatography thanks to the histidine tail (Clontech-Takara Bio Europe, France; Amocol, Germany) that incorporates all the flagellins expressed.

In order to obtain the recombinant flagellins by bacterial transformation, the following procedure was used. The fragment of interest, containing the fusion flagellin jointly with the histidine tail and the KDEL sequence, was isolated from the plasmids carrying the flagellin sequences of the invention by digestion with the Bam HI and Hind III restriction enzymes, and it was cloned by standard methods (rapid DNA ligation kit, Roche, Spain) in the pRSET-A vector (Invitrogen, United Kingdom), to produce the recombinant pRSETA plasmid bound to the flagellin sequence of interest. The recombinant pRSETA plasmid was used to transform BL21 (DE3)pLysS bacteria, following the manufacturer's recommendations (Invitrogen, United Kingdom). The expression of the protein in these transformed bacteria was induced after adding IPTG at a final concentration of 1 mM. The purification was performed by affinity chromatography, as explained above.

EXAMPLE 2

In Vitro Study of the Activity of *Marinobacter* Flagellins F and FR

In order to analyse the in vitro activity of the recombinant *Marinobacter* flagellins F and FR obtained using the commercial "Bac-to-Bac® Baculovirus system" method (Invitrogen, USA), human CACO-2 colon carcinoma cells were used which constitutively express the TLR5 receptor. When TLR5 is activated in these cells, it induces the activation of MyD88 in order to finally secrete IL-8 to the extracellular medium [8-10].

CACO-2 cells (0.5 ml) were cultured in a 24-well plate (Nunc, Denmark) with an 80% confluence and a concentration of 5×10$^5$ cells/well. Subsequently, the recombinant proteins from flagellin STF (*Salmonella typhimurium*), used as a positive control, F and FR (*Marinobacter algicola*) at a final concentration of 1 µg/ml, were added to the culture medium, and incubated for 18 hours at 37° C. in a 5% CO$_2$ atmosphere. Samples whereto nothing was added (MOCK) and others whereto PBS was added were used as negative controls. After said time had elapsed, the supernatants were collected and 100 µl thereof were used to determine the levels of cytokine IL-8 secreted by means of ELISA, following the manufacturer's instructions (eBioscience, Ltd., United Kingdom). The optical density was measured at 490 nm after stopping the development reaction.

The levels of IL-8 secreted by the CACO-2 cells cultured in the presence of the different flagellins are shown in FIG. 1. *Marinobacter* flagellins F and FR induce, through the activation of TLR5, IL-8 secretion levels similar to those induced by the *Salmonella typhimurium* flagellin (STF), by itself or fused to the 4DUD peptide (STF4DUD). On the other hand, the negative CACO-2 controls (PBS and MOCK) show a very low optical density, which indicates the validity of the assay. The values represented correspond to the arithmetic means of two independent assays.

EXAMPLE 3

"In Vivo" Study of the Vaccinal Capacity and the Immunogenicity of *Marinobacter* Fusion Flagellins F and FR Bound to 4 Tandem Copies of the DUD Epitope In order to analyse in vivo the vaccinal capacity and the immunogenicity of the *Marinobacter* flagellins F and FR obtained using the commercial "Bac-to-Bac® Baculovirus system" method (Invitrogen, USA), groups of 5 mice were immunised, by subcutaneous route (sc), with 30 µg of purified fusion flagellins STF4DUD (*Salmonella typhimurium*), F4DUD and FR4DUD (*Marinobacter algicola*). A group of 5 mice were also immunised by intranasal route (in) with the F4DUD protein. As a control group, 5 mice were inoculated with the DUD tetrapeptide (4DUD). 3 immunisations without adjuvants were applied on days 0, 15 and 30 of the assay, and blood samples were obtained from all the animals prior to each immunisation and 15 days following the last immunisation, although the serological studies of the presence of antibodies were performed with the sera following the second immunisation.

The serum from the blood extracted from each group of animals included in the assay was isolated and analysed by means of indirect ELISA on Maxisorp plastic 96-well plates (Nunc, Denmark) coated with 500 ng of purified p54 protein, which contains the DUD epitope. The protein is allowed to be adsorbed at 4° C. overnight. The analysis was performed using 100 µl/well, starting from a 1/100 dilution of the sera and one-half serial dilutions (1/100, 1/200, 1/400, 1/800, 1/1,600, 1/3,200, 1/6,400, 1/12,800) with BSA-PBST buffer, composed of 2% BSA (bovine serum albumin) in 0.1% Tween-20 phosphate buffer (PBST). The serum dilutions are incubated for 60 minutes and, subsequently, the wells are washed with 300 µl of PBST. Thereafter, the wells were incubated for 60 minutes with 100 µl of mouse anti-IgG monoclonal antibody conjugated with HRP (horseradish peroxidase) at a dilution of 1/2,000 (Amersham, UK). Subsequently, the wells were washed with PBST buffer. 100 µl/well of ABTS (2,2'-azino-bis(3-ethylbenzothiazoline-6-sulphonic acid)) (KPL, USA) were added for the development. The peroxidase reaction is allowed to develop for 15 minutes at ambient temperature, and the optical density at 405 nm is measured in an ELISA reader (Multiskan EX, Thermo Electron Corp, USA).

FIG. 2 shows the presence of IgG anti-DUD antibodies present in the sera of the different groups of mice on day 30, using a 1/100 dilution of said sera. This figure demonstrates that, when they are inoculated by subcutaneous route, the *Marinobacter* flagellins induce a humoural immune response against the DUD epitope that is as potent as that induced by *Salmonella typhimurium* flagellin STF, whereas the 4DUD peptide by itself is not capable of inducing antibodies. The data represented in FIG. 2 correspond to the arithmetic means of all the animals within each group. Thus, Table 1 shows the maximum and minimum mean optical densities at 405 nm for each group of mouse serum samples. On the other hand, the IgG antibody response induced by F4DUD, when it is inoculated by intranasal route (in), is very good, although slightly lower (in the arithmetic mean) than that obtained by subcutaneous route (sc) (FIG. 2 and table 1).

TABLE 1

Arithmetic means of the maximum and minimum values of IgG anti-DUD antibodies present in the sera of the mice immunised with fusion flagellins FR4DUD, F4DUD, STF4DUD and F4FUDin (intranasal).

|  | Maximum | Minimum |
| --- | --- | --- |
| FR4DUD | 2.28 | 1.63 |
| F4DUD | 2.494 | 2.115 |
| STF4DUD | 2.541 | 2.023 |
| F4DUDin | 2.144 | 1.236 |

The sera of the animals immunised with the *Marinobacter* flagellins (F4DUD and FR4DUD) and the *Salmonella typhimurium* flagellin (STF4DUD) have IgG anti-DUD antibodies at a titre greater than 1/12,800 (FIG. 3), since the optical density values of all the sera are above the cut-off point, defined as 3 times the optical density value of the 4DUD tetrapeptide (FIG. 3). These data indicate that the *Marinobacter* fusion flagellins (with the DUD epitope) induce a very potent immune response against said DUD epitope, without the aid of adjuvants, reaching titres of antibodies greater than 1/12,800. These results indicate that the *Marinobacter* flagellins appropriately interact with TLR5, thereby potently activating the immune system, in a manner similar to the *Salmonella typhimurium* flagellin, but without the potential disadvantages associated with said flagellins in subjects that have prior immunity against *Salmonella typhimurium*.

EXAMPLE 4

"In Vivo" Study of the Vaccinal Capacity of *Marinobacter* Fusion Flagellin FR Bound to 4 Tandem Copies of the M2-2009 Epitope In this example, we have studied "in vivo" the vaccinal and immunogenic capacity of *Marinobacter* flagellin FR in transcriptional fusion with 4 tandem copies of the M2-2009 peptide (SEQ ID NO: 27) at the 3'-end (c-terminal) of said flagellin FR. The M2 peptide sequence corresponds to the flu virus A/Castilla-La Mancha/GP13/2009(H1N1) pandemic strain (GenBank: FJ985750), which in this invention has been called 4M2-2009 (SEQ ID NO: 27). This recombinant flagellin FR was obtained from the pFastbac-FR-4M2-2009 plasmid (SEQ ID NO: 29). The fragment of interest, which contains the fusion flagellin, jointly with the histidine tail and the KDEL sequence (SEQ ID NO: 29), was isolated starting from this plasmid, by means of digestion with the Bam HI and Hind III restriction enzymes, and cloned by standard methods (rapid DNA ligation kit, Roche, Spain) in the pRSET-A vector (Invitrogen, United Kingdom), in order to produce a recombinant pRSETA-FR4M2-2009 plasmid (SEQ ID NO: 33). Using this recombinant plasmid, BL21(DE3)pLysS bacteria were transformed following the manufacturer's recommendations (Invitrogen, United Kingdom). The expression of the protein in these transformed bacteria was induced after adding IPTG at a final concentration of 1 mM. The purification was performed by means of affinity chromatography.

In order to evaluate the immunogenicity of recombinant flagellin FR-4M2-2009, 4 mice were inoculated by subcutaneous route (sc) with 10 µg of said purified flagellin and, as a control group, 4 mice were inoculated with 10 µg of the 4M2-2009 peptide in PBS. 2 immunisations were applied, without adjuvants, on days 0 and 15 of the assay, and blood samples were obtained from all the animals, prior to each immunisation and 15 days after the last immunisation, although the serological studies of the presence of antibodies were performed with the sera following the second immunisation.

The serum was isolated from the blood extracted and analysed by means of indirect ELISA on Maxisorp plastic 96-well plates (Nunc, Denmark) coated with 500 ng of a carrier protein containing the 4 copies of the M2-2009 peptide. The ELISA was performed using 100 µl/well, starting from a 1/100 dilution of the sera and one-half serial dilutions (1/100, 1/200, 1/400, 1/800, 1/1,600, 1/3,200, 1/6,400, 1/12, 800) with BSA-PBST buffer, following the steps explained above.

FIG. 4 shows the level of IgG anti-4M2-2009 antibodies present in the sera of the 4 mice studied (R1, R2, R3 and R4). A high titre of antibodies is observed in the mice immunised with FR-4M2-2009 as compared to the control mice (C1, C2, C3 and C4), which indicates that this flagellin is functional and suitable to generate an immune response against the 4M2-2009 epitope.

EXAMPLE 5

Cross-Reactivity Between *Marinobacter* Flagellins F and FR and *Salmonella* Flagellin STF In order to study the potential cross-reactivity between the *Marinobacter* flagellins (F and FR) and the *Salmonella thyphimurium* flagellin (STF) (obtained using the commercial "Bac-to-Bac® Baculovirus system" method (Invitrogen, USA)), all the sera from each group of animals immunised with the different versions of flagellins-4DUD were analysed. The study is performed following a standard immunisation pattern, as described in Example 2.

5.1. Cross-reactivity Toward *Salmonella* Flagellin STF.

Figure 5:
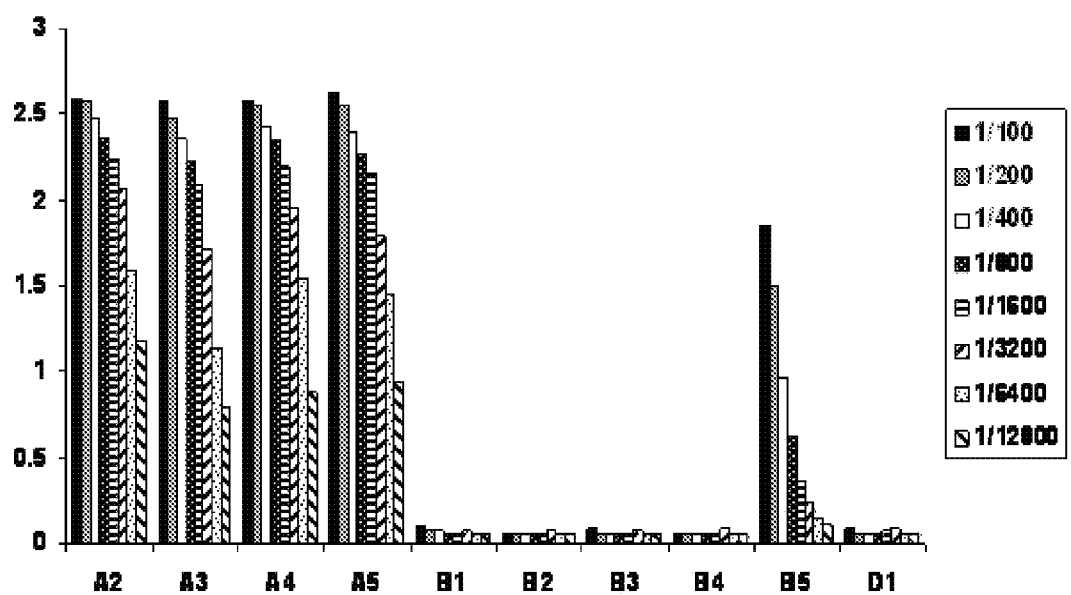
Figure 6:
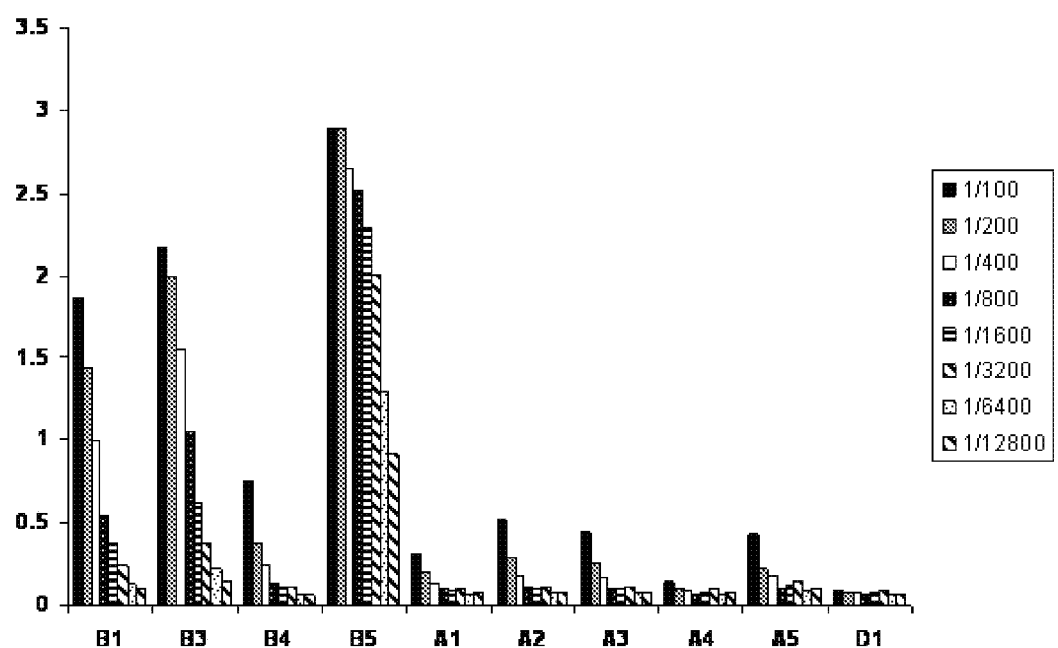

In order to analyse the cross-reactivity between flagellin STF and the antibodies against *Marinobacter* flagellin F and *Salmonella* flagellin STF, as a positive control, the above-mentioned 96-well culture plates were coated with 500 ng of STF protein previously purified by affinity chromatography based on the presence of the histidine tail, as explained above. The purified STF protein is allowed to be adsorbed on the culture plate overnight at 4° C. The analysis was performed by studying the sera of mice immunised with flagellin STF4DUD (serum group A), as a positive control, and the sera of mice that contained antibodies against flagellin F4DUD (serum group B) (FIG. 5). The indirect ELISA method described above was used, starting from the sera at a 1/100 dilution and performing one-half serial dilutions with the BSA-PBST buffer until a 1/12,800 dilution was reached. The result (FIG. 5) shows that the sera of animals immunised with STF4DUD (serum group A) contain a large quantity of anti-STF antibodies which bind to the purified STF protein present in the culture plate, reaching a titre greater than 1/12, 800. On the other hand, the sera of mice immunised with F4DUD (serum group B) exhibit a very low reactivity toward flagellin STF, with the exception of serum B5, which is the only one that exhibits reactivity, although at antibody levels that are 32 times lower than those of the positive controls (serum group A). The titres of IgG antibodies against flagellin F (serum group B) are shown in FIG. 6, where it may be observed that serum B5 has a higher titre of antibodies than the rest of the sera in that group. However, the response induced against DUD in each of the mice in that group was very good (represented in FIG. 2). Therefore, there may be a very good immunity against the epitope carried by the flagellin in fusion, but a heterogeneous immunity against the vaccinal flagellin.

These results indicate that it is possible that no cross-reaction takes place between the antibodies generated against *Marinobacter* flagellin F and *Salmonella typhimurium* flagellin STF, but, should it exist, it would be 32 times lower than a very positive serum (greater than 1/12,800).

Figure 8:
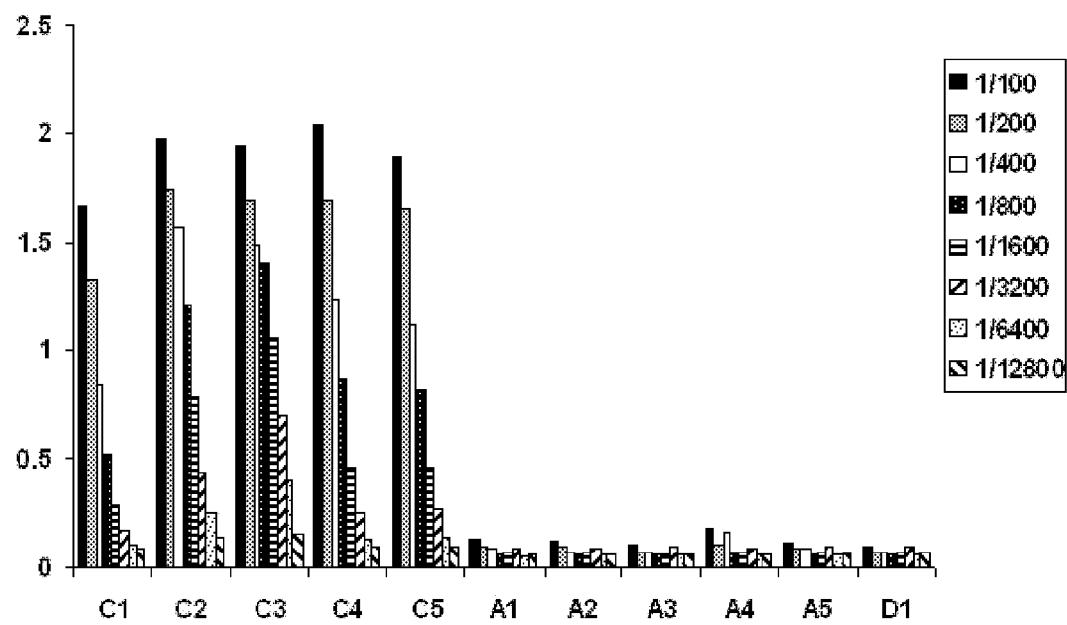
Figure 9:
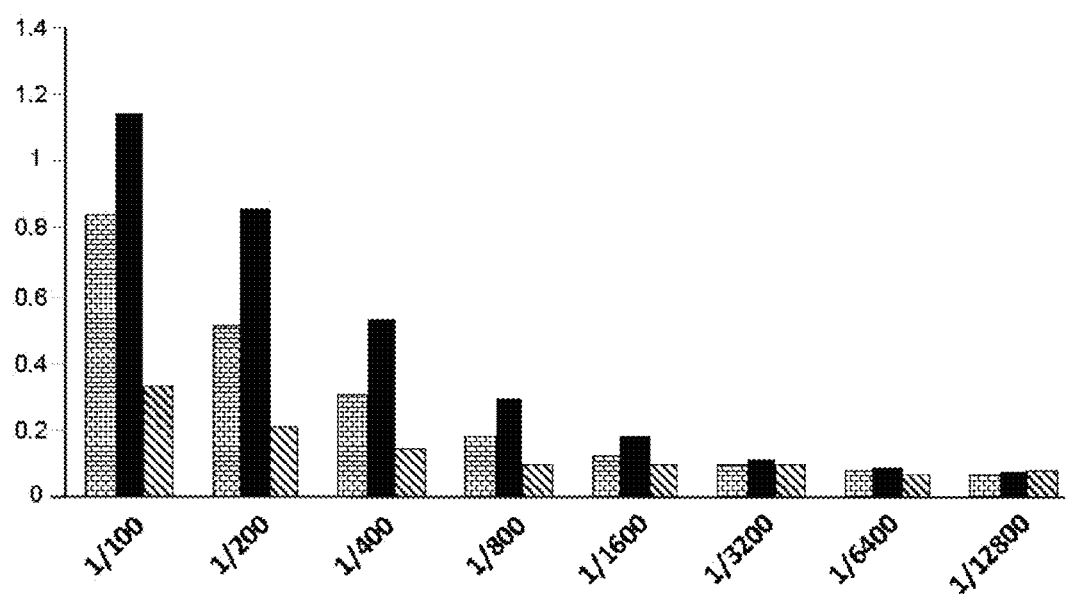

The cross-reaction between *Salmonella* flagellin STF and the anti-FR antibodies (serum group C) (FIG. 7) was also assayed, and the behaviour was similar to that observed for the anti-F antibodies. Only one of the five sera from the group of mice immunised with flagellin FR4DUD (serum group C) exhibits a greater cross-reactivity against STF (serum C3), although this reactivity may be quantified as 32 times lower than that of the positive controls for STF. Serum C3 exhibits a higher titre of anti-FR antibodies (3,200>IgG>6,400) than the rest of the sera in its group (FIG. 8). It may be stated that the most positive sera of animals immunised with *Marinobacter* flagellin FR would recognise the *Salmonella typhimurium* flagellin to a lesser extent.

5.2. Cross-reactivity Toward *Marinobacter* Flagellin F.

In order to analyse the cross-reactivity between flagellin F and the antibodies against *Salmonella typhimurium* flagellin STF and *Marinobacter* flagellin F, as a positive control, the same experimental protocol described above was used, coating the culture plate with 500 ng of flagellin F purified by means of affinity chromatography. We analysed the sera of mice that contain antibodies against flagellin STF4DUD (serum group A) and the sera of mice that contain antibodies against flagellin F4DUD (serum group B), which will act as a positive control. The result (FIG. 6) shows that the sera of animals immunised with F4DUD (serum group B) positively react toward the recognition of flagellin F, and it is observed that the positivity decreases with the serum dilution. On the other hand, the sera of mice immunised with STF4DUD (serum group A) exhibit scant cross-reaction with *Marinobacter* flagellin F, being very weakly positive at a 1/100 dilution, and having between 16 and 32 times less reactivity than the sera containing antibodies against flagellin F, which act as a positive control. However, these anti-STF sera that produce this scant reactivity are very positive toward the recognition of STF (FIGS. 3 and 5), with IgG anti-STF titres greater than 1/12,800, which possibly reach 1/25,600 (FIG. 5).

5.3. Cross-reactivity Toward *Marinobacter* Flagellin FR.

In order to analyse the cross-reactivity between flagellin FR and the antibodies against *Salmonella typhimurium* flagellin STF and *Marinobacter* flagellin FR, as a positive control, the same experimental protocol described above was used, coating the culture plate with 500 ng of flagellin FR purified by means of affinity chromatography. We studied the sera of mice that contain antibodies against flagellin FR4DUD (serum group C) and the sera of mice that contain antibodies against flagellin STF4DUD (serum group A). The result (FIG. 8) shows that the sera of animals immunised with FR4DUD (serum group C) positively react toward the recognition of flagellin FR, and it may be observed that the positivity decreases with the serum dilution. On the other hand, the antisera that recognise flagellin STF (serum group A) (following immunisation with STF4DUD) practically do not recognise flagellin FR, which represents between 64 and 128 times less recognition than the positive sera with anti-STF antibodies, which are very positive for the detection of STF (FIGS. 3 and 5), with IgG anti-STF titres greater than 1/12, 800 that may possibly reach 1/25,600 (FIG. 5).

5.4. Cross-reactivity of the Sera Against *Marinobacter* Flagellins F and FR Toward Flagellin F.

In order to analyse the cross-reactivity between both *Marinobacter* flagellins, an ELISA was performed using mouse sera that contained antibodies against *Marinobacter* flagellins FR and F, the latter as positive controls. 96-well culture plates were coated with 500 ng of flagellin F purified by means of affinity chromatography. We analysed the sera of mouse that contained antibodies against flagellin FR4DUD and the sera of mouse that contained antibodies against flagellin F4DUD (positive control). The result (FIG. 9) shows that the anti-FR serum (brick-shaped bars) has an optical density of 0.838, slightly lower than that obtained by the positive control (black bars), with an optical density of 1.14, these values corresponding to the 1/100 serum dilution. The other serum with anti-F4DUD antibodies analysed (bars with black oblique lines) has an optical density value of 0.329 at a 1/100 dilution, which indicates that it has not behaved as a good positive control, because, albeit being positive, it has less antibodies than its homologue (black bars, optical density of 1.14).

In sum, these results indicate that *Marinobacter* flagellin F has a slightly lower, albeit considerable, cross-reactivity toward the antibodies against flagellin FR than toward the antibodies against flagellin F. This may be explained by the amino acid sequence homology between both *Marinobacter* flagellins F and FR.

In this invention, the recognition of *Salmonella typhimurium* flagellin (STF) by the sera against *Marinobacter* flagellin F (FIG. 6) was very scant, and it is especially noteworthy that practically no recognition of STF by the antibodies against *Marinobacter* flagellin FR was observed. These data could be explained by the differences in amino acid sequence homology between the proteins. The *Salmonella* flagellin must have immunodominant antigenic determinants against which antibodies are produced, and these determinants are either absent from flagellins F and FR, or there is a change in the amino acid sequence that does not allow for them to be recognised. It is worth noting that, in the immunisation pattern against STF4DUD, no antibodies have appeared against the regions of interaction with TLR5, since, should these exist, they would show positive reactivity toward anti-F and anti-FR sera.

The existence of antibodies against the *Salmonella typhimurium* flagellin due to previous infections or the prior vaccinal use of the *Salmonella* flagellin may progressively inhibit the functionality of vaccines based on the *Salmonella typhimurium* flagellin, until it is finally eliminated. In this regard, this invention makes it possible to specify the administration of vaccinal *Marinobacter* flagellins F and FR (preferably) to subjects with a large amount of antibodies against the *Salmonella* flagellin, being sure that the vaccinal *Marinobacter* flagellins will not be recognised by the pre-formed antibodies against the *Salmonella typhimurium* flagellin, generated after an immunisation procedure with high doses of the *Salmonella typhimurium* flagellin such as the one described.

Thus, subjects from any species exposed to *Salmonella typhimurium*, or vaccinated with the *Salmonella typhimurium* flagellin, which exhibit a certain titre of pre-formed antibodies against this *Salmonella* flagellin could be vaccinated with the *Marinobacter* flagellins (F or FR), using standard immunisation patterns, being sure that these vaccinal *Marinobacter* flagellins will not be recognised by the pre-formed antibodies against the *Salmonella typhimurium* flagellin. On the other hand, in subjects that have not been previously exposed to *Salmonella typhimurium*, another vaccination strategy could be used, which consists of initially administering any of the two *Marinobacter* flagellins (F or FR) and, subsequently, administering another vaccine based on the *Salmonella* flagellin, or vice-versa, that is, administering the vaccinal *Salmonella* flagellin and, subsequently, the vaccinal *Marinobacter* flagellin. This would enhance the use of these vaccines for multiple antigens without reducing the efficacy thereof due to cross-seroneutralisation between flagellins. Therefore, these results make it possible to establish new administration strategies for multiple flagellin-based vaccines, applying the *Marinobacter* flagellin vaccines by themselves, or jointly with *Salmonella* flagellin vaccines.

BIBLIOGRAPHY

1. Yonekura, K., S. Maki-Yonekura, and K. Namba, Complete atomic model of the bacterial flagellar filament by electron cryomicroscopy. Nature, 2003. 424(6949): pp. 643-50.
2. Samatey, F. A., et al., Structure of the bacterial flagellar protofilament and implications for a switch for supercoiling. Nature, 2001. 410(6826): pp. 331-37.
3. Stecher, B., et al., Flagella and chemotaxis are required for efficient induction of *Salmonella enterica* serovar *Typhimurium* colitis in streptomycin-pretreated mice. Infect Immun, 2004. 72(7): pp. 4138-50.
4. Smith, K. D., et al., Toll-like receptor 5 recognizes a conserved site on flagellin required for protofilament formation and bacterial motility. Nat Immunol, 2003. 4(12): pp. 1247-53.
5. Rumbo, M., et al., Mucosal interplay among commensal and pathogenic bacteria: lessons from flagellin and Toll-like receptor 5. FEBS Lett, 2006. 580(12): pp. 2976-84.
6. Rock, F. L., et al., A family of human receptors structurally related to *Drosophila* Toll. Proc Natl Acad Sci USA, 1998. 95(2): pp. 588-93.
7. Janssens, S. m and R. Beyaert, Role of Toll-like receptors in pathogen recognition. Clin Microbiol Rev, 2003. 16(4): pp. 637-46.
8. Akira, S., K. Takeda, and T. Kaisho, Toll-like receptors: critical proteins linking innate and acquired immunity. Nat Immunol, 2001. 2(8): pp. 675-80.
9. Honko, A. N. m and S. B. Mizel, Effects of flagellin on innate and adaptive immunity. Immunol Res, 2005. 33(1): pp. 83-101.
10. Akira, S., and K. Takeda, Functions of toll-like receptors: lessons from KO mice. C R Biol, 2004. 327(6): pp. 581-89.
11. McDermott, P. F., et al., High-affinity interaction between gram-negative flagellin and a cell surface polypeptide results in human monocyte activation. Infect Immun, 2000. 68(10): pp. 5525-29.

12. Andersen-Nissen, E., et al., Evasion of Toll-like receptor 5 by flagellated bacteria. Proc Natl Acad Sci USA, 2005. 102(26): pp. 9247-52.
13. Galkin, V. E., et al., Divergence of quaternary structures among bacterial flagellar filaments. Science, 2008. 320 (5874): pp. 382-85.
14. Audibert, F. M., and L. D. Lise, Adjuvants: current status, clinical perspectives and future prospects. Immunol Today, 1993. 14(6): pp. 281-84.
15. Levine, M. M., and M. B. Sztein, Vaccine development strategies for improving immunization: the role of modern immunology. Nat Immunol, 2004. 5(5): pp. 460-64.
16. Pearson, C. M., Development of arthritis, periarthritis and periostitis in rats given adjuvants. Proc Soc Exp Biol Med, 1956. 91(1): pp. 95-101.
17. Schijns, V. E., Immunological concepts of vaccine adjuvant activity. Curr Opin Immunol, 2000. 12(4): pp. 456-63.
18. Newton, S. M., C. O. Jacob, and B. A. Stocker, Immune response to cholera toxin epitope inserted in *Salmonella* flagellin. Science, 1989. 244(4900): pp. 70-72.
19. Ben-Yedidia, T., and R. Arnon, Epitope-based vaccine against influenza. Expert Rev Vaccines, 2007. 6(6): pp. 939-48.
20. Huleatt, J. W., et al., Potent immunogenicity and efficacy of a universal influenza vaccine candidate comprising a recombinant fusion protein linking influenza M2e to the TLR5 ligand flagellin. Vaccine, 2008. 26(2): pp. 201-14.
21. Honko, A. N., et al., Flagellin is an effective adjuvant for immunization against lethal respiratory challenge with *Yersinia pestis*. Infect Immun, 2006. 74(2): pp. 1113-20.
22. Mizel, S. B., et al., Flagellin-F1-V fusion protein is an effective plague vaccine in mice and two species of non-human primates. Clin Vaccine Immunol, 2009. 16(1): pp. 21-28.
23. Bargieri, D. Y., et al., New malaria vaccine candidates based on the *Plasmodium vivax* Merozoite Surface Protein-1 and the TLR-5 agonist *Salmonella Typhimurium* FliC flagellin. Vaccine, 2008. 26(48): pp. 6132-42.
24. McDonald, W. F., et al., A West Nile virus recombinant protein vaccine that coactivates innate and adaptive immunity. J Infect Dis, 2007. 195(11): pp. 1607-17.
25. Fierer, J., and D. G. Guiney, Diverse virulence traits underlying different clinical outcomes of *Salmonella* infection. J Clin Invest, 2001. 107(7): pp. 775-80.
26. Wells, J. V., H. H. Fudenberg, and I. R. MacKay, Relation of the human antibody response to flagellin to GM genotype. J Immunol, 1971. 107(6): pp. 1505-11
27. Dalby, T., et al., Rapid decay of *Salmonella* flagella antibodies during human gastroenteritis: a follow up study. J Microbiol Methods, 2005. 62(2): pp. 233-43.
28. Ben-Yedidia, T., and R. Arnon, Effect of pre-existing carrier immunity on the efficacy of synthetic influenza vaccine. Immunol Lett, 1998. 64(1): pp. 9-15.
29. McDonough, P. L., et al., Interpretations of antibody responses to *Salmonella enterica* serotype enteritidis gm flagellin in poultry flocks are enhanced by a kinetics-based enzyme-linked immunosorbent assay. Clin Diagn Lab Immunol, 1998. 5(4): pp. 550-55.
30. Nempont, C., et al., Deletion of flagellin's hypervariable region abrogates antibody-mediated neutralization and systemic activation of TLR5-dependent immunity. J Immunol, 2008. 181(3): pp. 2036-43.
31. Huu, N. B., et al., *Marinobacter aquaeolei* sp. nov., a halophilic bacterium isolated from a Vietnamese oil-producing well. Int J Syst Bacteriol, 1999. 49 Pt 2: pp. 367-75.
32. Shieh, W. Y., et al., *Marinobacter lutaoensis* sp. nov., a thermotolerant marine bacterium isolated from a coastal hot spring in Lutao, Taiwan. Can J Microbiol, 2003. 49(4): pp. 244-52.
33. Yoon, J. H., et al., *Marinobacter flavimaris* sp. nov. and *Marinobacter daepoensis* sp. nov., slightly halophilic organisms isolated from sea water of the Yellow Sea in Korea. Int J Syst Evol Microbiol, 2004. 54 (Pt 5): pp. 1799-803.
34. Shivaji, S., et al., *Marinobacter maritimus* sp. nov., a psychrotolerant strain isolated from sea water off the sub-antarctic Kerguelen islands. Int J Syst Evol Microbiol, 2005. 55 (Pt 4): pp. 1453-56.
35. Martin, S., et al., *Marinobacter lipolyticus* sp. nov., a novel moderate halophile with lipolytic activity. Int J Syst Evol Microbiol, 2003. 53 (Pt 5): pp. 1383-87.
36. Gorshkova, N. M., et al., *Marinobacter excellens* sp. nov., isolated from sediments of the Sea of Japan. Int J Syst Evol Microbiol, 2003. 53 (Pt 6): pp. 2073-78.
37. Green, D. H., et al., *Marinobacter algicola* sp. nov., isolated from laboratory cultures of paralytic shellfish toxin-producing dinoflagellates. Int J Syst Evol Microbiol, 2006. 56 (Pt 3): pp. 523-27.
38. Gómez-Puertas, P., et al., The African swine fever virus proteins p54 and p30 are involved in two distinct steps of virus attachment and both contribute to the antibody-mediated protective immune response. Virology, 1998. 243 (2): pp. 461-71.
39. Alonso, C., et al., African swine fever virus protein p54 interacts with the microtubular motor complex through direct binding to light-chain dynein. J Virol, 2001. 75(20): pp. 9819-27.
40. Altschul, S. F., et al., Gapped BLAST and PSI-BLAST: a new generation of protein database search programs. Nucleic Acids Res, 1997. 25(17): pp. 3389-402.
41. Altschul, S. F., et al., Protein database searches using compositionally adjusted substitution matrices. FEBS J, 2005. 272(20): pp. 5101-09.
42. Larkin, M. A., et al., Clustal W and Clustal X version 2.0. Bioinformatics, 2007. 23(21): pp. 2947-48.

The invention claimed is:

1. A vaccination method that comprises administering to a subject at least one effective dose of a first vaccine that comprises a vaccine adjuvant comprising at least one flagellin from *Marinobacter algicola*, wherein the vaccine adjuvant is fused to at least one epitope capable of generating an immunological response, and wherein the vaccine adjuvant is characterised in that it contains at least one amino acid sequence selected from the group consisting of: SEQ ID NO: 2, SEQ ID NO: 4, SEQ ID NO: 20, and SEQ ID NO: 22 or one amino acid sequence encoded by: SEQ ID NO: 1, SEQ ID NO: 3, SEQ ID NO: 19, or SEQ ID NO: 21.

2. The vaccination method of claim 1, further comprising administering at least one effective dose of a second vaccine that comprises *Salmonella* flagellin.

3. The vaccination method of claim 2, wherein an order of administration of the effective dose of the first vaccine and the effective dose of the second vaccine is interchangeable.

4. The vaccination method of claim 1, wherein four tandem copies of the epitope are fused to the vaccine adjuvant.

5. The vaccination method of claim 1, wherein the vaccine adjuvant is further fused to an amino acid sequence consisting of Lys-Asp-Glu-Leu.

6. The vaccination method of claim 1, wherein the first vaccine comprises at least one amino acid sequence selected from the group consisting of: SEQ ID NO: 6, SEQ ID NO: 8, SEQ ID NO: 24, SEQ ID NO: 26, SEQ ID NO: 29 and SEQ ID NO: 31, or one amino acid sequence encoded by: SEQ ID NO: 5, SEQ ID NO: 7, SEQ ID NO: 23, SEQ ID NO: 25, SEQ ID NO: 28 or SEQ ID NO: 30.

* * * * *

SEQUENCE LISTING

```
<160> NUMBER OF SEQ ID NOS: 33

<210> SEQ ID NO 1
<211> LENGTH: 1566
<212> TYPE: DNA
<213> ORGANISM: Marinobacter algicola (DG893)
<220> FEATURE:
<221> NAME/KEY: Flagellin F
<222> LOCATION: (1)..(1566)
<220> FEATURE:
<221> NAME/KEY: characteristic
```

<222> LOCATION: (1525)..(1545)
<223> OTHER INFORMATION: Region that encodes a histidine tail
<220> FEATURE:
<221> NAME/KEY: characteristic
<222> LOCATION: (1553)..(1563)
<223> OTHER INFORMATION: Region that encodes the KDEL sequence

<400> SEQUENCE: 1

```
atgcctcaga tcatcaacac caatattgcg tcgctgaatg cacagcgaaa cctgaatact    60
tcgcaggaag actccaacgt tgccctgcag cgactgtcat ccggcctgcg tatcaactcc   120
gccaaggacg acgccgccgg actggccatc tccgagcgat tcacatcgca gatcaaaggt   180
ctcaaccagg ccattcgaaa cgccaatgac ggtatttccc tggctcagac cgccgaaggc   240
gccctgggcg aatccggaaa catcctgcag cgcatccggg aactcgccgt acagtccgcc   300
aacgctacca actccgcatc tgacaggaag gccctgcagt ctgaagtaaa ccagctaaaa   360
ggtgagctcg agcgcattgc caccaccacc gaattcaacg gactgaaact tctggacggc   420
accttccagg ctcagaagtt ccaggctggc gccaacgaaa accagagcat cgccgttccc   480
atcgaaggtg cccgaaccgc cgacctagca acaacacgc tcgacgctgc caacgcaacc    540
ctgaaccagg gcaccggttc aacaacggca gcgaatgcga cgttacccgc acaaaacacg   600
atcgccacgc agaatctcac catttccagc tcgctggaca gccaggtggt gcccattaca   660
gcaggtgaca cagcggaaga catcgccgca gccatcaacg acattggtgc cacgacgggt   720
gtgaacgcaa cggcaagaac atcggcgacc ctgagcaaca ccgctaccac gccaatcgcc   780
gtgcctcaaa ccgtatcgct cacgctttcc aacggtagca gttcagcaac catttccgcg   840
cagatcaccg atgcgaacga cctctcagca attgcacgtg aggtgaacgc agcttccggc   900
aagaccggca ttaccgcgga agtcgctaac gacggcagca tcacgctgat tcaggagcaa   960
ggtaaagaca tcactattga agactttacc gcagcgggct ctcagcaact ggcggtacag  1020
ggtagtggcg atccaagtgc catcgaactg acaaacggtg gtgccaatgc cacacgtatc  1080
gccggggaat tgacactgga ctcctccgtt agcttcgcgg cgacgtctga cgccaccctg  1140
gccgcaggca gcgttctgaa cagtgcacag aataccgccg ccggctccac acctgaagaa  1200
gtggcaggta ttgatataag caccgttgac ggcgcaacca gtgcacttgc agttgtggat  1260
gcggcattgg aaaccatcag tggcattcgt gccgatctgg gcgccgcgca gaatcgactc  1320
gagtcgacca ttgccaacct gagtacgacc tctgagaacc tttcggccgc gcgttcgcga  1380
attcgtgatg cagactttgc cgccgaatcc gcggaactcg cccgcaccca agtgctccag  1440
caggctggct tgtcggtatt ggcccaggcc aacgcaagac cgcagcaggt tctgcagctg  1500
ctgcagggtg catgcggttc tagacatcac caccaccatc accatgctag aaaagatgaa  1560
ctgtaa                                                             1566
```

<210> SEQ ID NO 2
<211> LENGTH: 521
<212> TYPE: PRT
<213> ORGANISM: Marinobacter algicola (DG893)
<220> FEATURE:
<221> NAME/KEY: Flagellin F
<222> LOCATION: (1)..(521)
<220> FEATURE:
<221> NAME/KEY: CHARACTERISTIC
<222> LOCATION: (509)..(515)
<223> OTHER INFORMATION: Histidine tail
<220> FEATURE:
<221> NAME/KEY: CHARACTERISTIC
<222> LOCATION: (518)..(521)
<223> OTHER INFORMATION: KDEL sequence

<400> SEQUENCE: 2

```
Met Pro Gln Ile Ile Asn Thr Asn Ile Ala Ser Leu Asn Ala Gln Arg
1               5                   10                  15

Asn Leu Asn Thr Ser Gln Glu Asp Ser Asn Val Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Lys Gly Leu Asn Gln Ala
    50                  55                  60

Ile Arg Asn Ala Asn Asp Gly Ile Ser Leu Ala Gln Thr Ala Glu Gly
65                  70                  75                  80

Ala Leu Gly Glu Ser Gly Asn Ile Leu Gln Arg Ile Arg Glu Leu Ala
                85                  90                  95

Val Gln Ser Ala Asn Ala Thr Asn Ser Ala Ser Asp Arg Lys Ala Leu
            100                 105                 110

Gln Ser Glu Val Asn Gln Leu Lys Gly Glu Leu Glu Arg Ile Ala Thr
        115                 120                 125

Thr Thr Glu Phe Asn Gly Leu Lys Leu Leu Asp Gly Thr Phe Gln Ala
130                 135                 140

Gln Lys Phe Gln Ala Gly Ala Asn Glu Asn Gln Ser Ile Ala Val Ser
145                 150                 155                 160

Ile Glu Gly Ala Arg Thr Ala Asp Leu Ala Asn Asn Thr Leu Asp Ala
                165                 170                 175

Ala Asn Ala Thr Leu Asn Gln Gly Thr Gly Ser Thr Thr Ala Ala Asn
            180                 185                 190

Ala Thr Leu Pro Ala Gln Asn Thr Ile Ala Thr Gln Asn Leu Thr Ile
        195                 200                 205

Ser Ser Ser Leu Asp Ser Gln Val Val Pro Ile Thr Ala Gly Asp Thr
    210                 215                 220

Ala Glu Asp Ile Ala Ala Ala Ile Asn Asp Ile Gly Ala Thr Thr Gly
225                 230                 235                 240

Val Asn Ala Thr Ala Arg Thr Ser Ala Thr Leu Ser Asn Thr Ala Thr
                245                 250                 255

Thr Pro Ile Ala Val Pro Gln Thr Val Ser Leu Thr Leu Ser Asn Gly
            260                 265                 270

Ser Ser Ser Ala Thr Ile Ser Ala Gln Ile Thr Asp Ala Asn Asp Leu
        275                 280                 285

Ser Ala Ile Ala Arg Glu Val Asn Ala Ala Ser Gly Lys Thr Gly Ile
    290                 295                 300

Thr Ala Glu Val Ala Asn Asp Gly Ser Ile Thr Leu Ile Gln Glu Gln
305                 310                 315                 320

Gly Lys Asp Ile Thr Ile Glu Asp Phe Thr Ala Ala Gly Ser Gln Gln
                325                 330                 335

Leu Ala Val Gln Gly Ser Gly Asp Pro Ser Ala Ile Glu Leu Thr Asn
            340                 345                 350

Gly Gly Ala Asn Ala Thr Arg Ile Ala Gly Glu Leu Thr Leu Asp Ser
        355                 360                 365

Ser Val Ser Phe Ala Ala Thr Ser Asp Ala Thr Leu Ala Ala Gly Ser
    370                 375                 380

Val Leu Asn Ser Ala Gln Asn Thr Ala Gly Ser Thr Pro Glu Glu
385                 390                 395                 400

Val Ala Gly Ile Asp Ile Ser Thr Val Asp Gly Ala Thr Ser Ala Leu
```

```
                     405                 410                 415
Ala Val Val Asp Ala Ala Leu Glu Thr Ile Ser Gly Ile Arg Ala Asp
                420                 425                 430

Leu Gly Ala Ala Gln Asn Arg Leu Glu Ser Thr Ile Ala Asn Leu Ser
            435                 440                 445

Thr Thr Ser Glu Asn Leu Ser Ala Ala Arg Ser Arg Ile Arg Asp Ala
        450                 455                 460

Asp Phe Ala Ala Glu Ser Ala Glu Leu Ala Arg Thr Gln Val Leu Gln
465                 470                 475                 480

Gln Ala Gly Leu Ser Val Leu Ala Gln Ala Asn Ala Arg Pro Gln Gln
                485                 490                 495

Val Leu Gln Leu Leu Gln Gly Ala Cys Gly Ser Arg His His His His
            500                 505                 510

His His His Ala Arg Lys Asp Glu Leu
        515                 520

<210> SEQ ID NO 3
<211> LENGTH: 1557
<212> TYPE: DNA
<213> ORGANISM: Marinobacter algicola (DG893)
<220> FEATURE:
<221> NAME/KEY: Flagellin FR
<222> LOCATION: (1)..(1557)
<220> FEATURE:
<221> NAME/KEY: characteristic
<222> LOCATION: (1516)..(1536)
<223> OTHER INFORMATION: Region that encodes a histidine tail
<220> FEATURE:
<221> NAME/KEY: characteristic
<222> LOCATION: (1543)..(1554)
<223> OTHER INFORMATION: Region that encodes the KDEL sequence

<400> SEQUENCE: 3
atggctctcg gtattaacac taacgttgcg tcactgtcag ctcagaacca gctgaacaaa      60
tcccaggagc tttctaacca agctctggag cgtctgtctt ccggtctgcg catcaactcc     120
gccaaggacg atgctgctgg ccttgcaatt tcgacccgtt ttcagtccca gatctctggt     180
ctgaatgttg cccagcgtaa cgccaacgac ggtatttccc tggctcagac tgctgaaggt     240
gctctggaag aaaccaccaa catcctgcag cgcatccgtg agctgtctgt tcagtcggcc     300
aactctacca actcttcttc cgaccgctct gcacttcagg gcgaagtaaa ccagctgaag     360
caagagcttg atcgtattgc cggtaccacc cagtttaacg gcctcaacct tctggatggc     420
agcttcactg cccagtcatt ccaggttggt gccaacgcta accagaccat ctcggtctct     480
gtaactggcg ctcgtggtgc cgaccttggt aacaacaccg tatccggtga agtgatacc     540 actgtcagtc agggcacggg ttctgttgca gtcgcggccg ctgatgtggc aaccgttgcc     600
aacaatacga ttgctacaca gaacatcacc gtttctggaa ctgaaggctc tgaggtcatc     660
ggtattaccc aggcgatac tgcagaagcg attgcggctg ctgttaacgc tgaaaccggc     720
acgactggtg taacggctac ggcatccacc acggcaaccc tcgctggtct gtctgacgat     780
ggtacggttt cctttacgct tggcagtggt ggcgacacag cgaccatctc cgcagcggta     840
acgaccactg acctgggtgc gctggccaaa gcgatcaacg atacctcagg caccactggt     900
gttacggctg aagcaaacgg tggcgaaatc acactgaccc aggctgatgg caaagacatc     960
cgtctgcagg actttgccaa ctcaggtaac gcgaccggta ccgccacgct gcagggcagc     1020
ggtgacccat cagcggttac tttgaccgct ggcagcactg acagcacgat tgcttctggc     1080
tctgttgaat cgcctcttc cggtgcattc tcagtaagct cctctgtcgc agagactgcc     1140
```

```
ggtagcattc tgaacgtcgc agccgacacc gtggttggtt ccaacctcca gtcagtgtct   1200
tctatcgaca tcggtactgt tgcgggcgct aacagcgcaa tcgagattgc agatgcggct   1260
ctggagcaga tcagtggtat ccgcgccgat ctgggtgctg cccagaaccg gttcgagtct   1320
acgatcgcca acctgagcac aactgccgaa aacctgtcgg ccgctaacag ccggattctg   1380
gatgcagact tcgcatctga aactgctaag ctgtccaagg cgcaggttct ccagcaagct   1440
ggtatctctg tactggcaca ggcgaatgcc cgtccacagc aggttctgtc cctcctgcag   1500
gcatgcggtt ctagacatca ccaccaccat caccatgcta gaaaagatga actgtaa     1557
```

<210> SEQ ID NO 4
<211> LENGTH: 518
<212> TYPE: PRT
<213> ORGANISM: Marinobacter algicola (DG893)
<220> FEATURE:
<221> NAME/KEY: Flagellin FR
<222> LOCATION: (1)..(518)
<220> FEATURE:
<221> NAME/KEY: CHARACTERISTIC
<222> LOCATION: (506)..(512)
<223> OTHER INFORMATION: Histidine tail
<220> FEATURE:
<221> NAME/KEY: CHARACTERISTIC
<222> LOCATION: (514)..(518)
<223> OTHER INFORMATION: KDEL sequence

<400> SEQUENCE: 4

```
Met Ala Leu Gly Ile Asn Thr Asn Val Ala Ser Leu Ser Ala Gln Asn
1               5                   10                  15

Gln Leu Asn Lys Ser Gln Glu Leu Ser Asn Gln Ala Leu Glu Arg Leu
            20                  25                  30

Ser Ser Gly Leu Arg Ile Asn Ser Ala Lys Asp Asp Ala Ala Gly Leu
        35                  40                  45

Ala Ile Ser Thr Arg Phe Gln Ser Gln Ile Ser Gly Leu Asn Val Ala
    50                  55                  60

Gln Arg Asn Ala Asn Asp Gly Ile Ser Leu Ala Gln Thr Ala Glu Gly
65                  70                  75                  80

Ala Leu Glu Glu Thr Thr Asn Ile Leu Gln Arg Ile Arg Glu Leu Ser
                85                  90                  95

Val Gln Ser Ala Asn Ser Thr Asn Ser Ser Ser Asp Arg Ser Ala Leu
            100                 105                 110

Gln Gly Glu Val Asn Gln Leu Lys Gln Glu Leu Asp Arg Ile Ala Gly
        115                 120                 125

Thr Thr Gln Phe Asn Gly Leu Asn Leu Leu Asp Gly Ser Phe Thr Ala
    130                 135                 140

Gln Ser Phe Gln Val Gly Ala Asn Ala Asn Gln Thr Ile Ser Val Ser
145                 150                 155                 160

Val Thr Gly Ala Arg Gly Ala Asp Leu Gly Asn Asn Thr Val Ser Gly
                165                 170                 175

Glu Ser Asp Thr Thr Val Ser Gln Gly Thr Gly Ser Val Ala Val Ala
            180                 185                 190

Ala Ala Asp Val Ala Thr Val Ala Asn Asn Thr Ile Ala Thr Gln Asn
        195                 200                 205

Ile Thr Val Ser Gly Thr Glu Gly Ser Glu Val Ile Gly Ile Thr Gln
    210                 215                 220

Gly Asp Thr Ala Glu Ala Ile Ala Ala Ala Val Asn Ala Glu Thr Gly
225                 230                 235                 240
```

-continued

```
Thr Thr Gly Val Thr Ala Thr Ala Ser Thr Thr Ala Thr Leu Ala Gly
            245                 250                 255

Leu Ser Asp Asp Gly Thr Val Ser Phe Thr Leu Gly Ser Gly Gly Asp
        260                 265                 270

Thr Ala Thr Ile Ser Ala Ala Val Thr Thr Asp Leu Gly Ala Leu
        275                 280                 285

Ala Lys Ala Ile Asn Asp Thr Ser Gly Thr Gly Val Thr Ala Glu
    290                 295                 300

Ala Asn Gly Gly Glu Ile Thr Leu Thr Gln Ala Asp Gly Lys Asp Ile
305                 310                 315                 320

Arg Leu Gln Asp Phe Ala Asn Ser Gly Asn Ala Thr Gly Thr Ala Thr
                325                 330                 335

Leu Gln Gly Ser Gly Asp Pro Ser Ala Val Thr Leu Thr Ala Gly Ser
            340                 345                 350

Thr Asp Ser Thr Ile Ala Ser Gly Ser Val Glu Phe Ala Ser Ser Gly
        355                 360                 365

Ala Phe Ser Val Ser Ser Ser Val Ala Glu Thr Ala Gly Ser Ile Leu
    370                 375                 380

Asn Val Ala Ala Asp Thr Val Val Gly Ser Asn Leu Gln Ser Val Ser
385                 390                 395                 400

Ser Ile Asp Ile Gly Thr Val Ala Gly Ala Asn Ser Ala Ile Glu Ile
                405                 410                 415

Ala Asp Ala Ala Leu Glu Gln Ile Ser Gly Ile Arg Ala Asp Leu Gly
            420                 425                 430

Ala Ala Gln Asn Arg Phe Glu Ser Thr Ile Ala Asn Leu Ser Thr Thr
        435                 440                 445

Ala Glu Asn Leu Ser Ala Ala Asn Ser Arg Ile Leu Asp Ala Asp Phe
    450                 455                 460

Ala Ser Glu Thr Ala Lys Leu Ser Lys Ala Gln Val Leu Gln Gln Ala
465                 470                 475                 480

Gly Ile Ser Val Leu Ala Gln Ala Asn Ala Arg Pro Gln Gln Val Leu
                485                 490                 495

Ser Leu Leu Gln Ala Cys Gly Ser Arg His His His His His His
            500                 505                 510

Ala Arg Lys Asp Glu Leu
        515

<210> SEQ ID NO 5
<211> LENGTH: 1884
<212> TYPE: DNA
<213> ORGANISM: Marinobacter algicola (DG893)
<220> FEATURE:
<221> NAME/KEY: Flagellin F4DUD
<222> LOCATION: (1)..(1884)
<220> FEATURE:
<221> NAME/KEY: characteristic
<222> LOCATION: (1516)..(1590)
<223> OTHER INFORMATION: DUD epitope
<220> FEATURE:
<221> NAME/KEY: characteristic
<222> LOCATION: (1597)..(1671)
<223> OTHER INFORMATION: DUD epitope
<220> FEATURE:
<221> NAME/KEY: characteristic
<222> LOCATION: (1678)..(1752)
<223> OTHER INFORMATION: DUD epitope
<220> FEATURE:
<221> NAME/KEY: characteristic
<222> LOCATION: (1759)..(1833)
<223> OTHER INFORMATION: DUD epitope
<220> FEATURE:
```

<210> SEQ ID NO 5
<211> LENGTH: 1884
<212> TYPE: DNA
<213> ORGANISM: Artificial Sequence
<220> FEATURE:
<223> OTHER INFORMATION: Synthetic construct
<220> FEATURE:
<221> NAME/KEY: characteristic
<222> LOCATION: (1834)..(1863)
<223> OTHER INFORMATION: Sequence that encodes a histidine tail
<220> FEATURE:
<221> NAME/KEY: characteristic
<222> LOCATION: (1870)..(1881)
<223> OTHER INFORMATION: Sequence that encodes the KDEL sequence

<400> SEQUENCE: 5

```
atgcctcaga tcatcaacac caatattgcg tcgctgaatg cacagcgaaa cctgaatact      60
tcgcaggaag actccaacgt tgccctgcag cgactgtcat ccggcctgcg tatcaactcc     120
gccaaggacg acgccgccgg actggccatc tccgagcgat tcacatcgca gatcaaaggt     180
ctcaaccagg ccattcgaaa cgccaatgac ggtatttccc tggctcagac cgccgaaggc     240
gccctgggcg aatccggaaa catcctgcag cgcatccggg aactcgccgt acagtccgcc     300
aacgctacca actccgcatc tgacaggaag gccctgcagt ctgaagtaaa ccagctaaaa     360
ggtgagctcg agcgcattgc caccaccacc gaattcaacg gactgaaact tctggacggc     420
accttccagg ctcagaagtt ccaggctggc gccaacgaaa accagagcat cgccgtttcc     480
atcgaaggtg cccgaaccgc cgacctagca acaacacgc tcgacgctgc caacgcaacc     540
ctgaaccagg gcaccggttc aacaacggca gcgaatgcga cgttacccgc acaaaacacg     600
atcgccacgc agaatctcac catttccagc tcgctggaca gccaggtggt gcccattaca     660
gcaggtgaca gcggaaga catcgccgca gccatcaaca cattggtgc cacgacgggt     720
gtgaacgcaa cggcaagaac atcggcgacc ctgagcaaca ccgctaccac gccaatcgcc     780
gtgcctcaaa ccgtatcgct cacgctttcc aacggtagca gttcagcaac catttccgcg     840
cagatcaccg atgcgaacga cctctcagca attgcacgtg aggtgaacgc agcttccggc     900
aagaccggca ttaccgcgga agtcgctaac gacggcagca tcacgctgat tcaggagcaa     960
ggtaaagaca tcactattga agactttacc gcagcgggct ctcagcaact ggcggtacag    1020
ggtagtggcg atccaagtgc catcgaactg acaaacggtg gtgccaatgc cacacgtatc    1080
gccggggaat tgacactgga ctcctccgtt agcttcgcgg cgacgtctga cgccacccctg    1140
gccgcaggca gcgttctgaa cagtgcacag aataccgccg ccggctccac acctgaagaa    1200
gtggcaggta ttgatataag caccgttgac ggcgcaacca gtgcacttgc agttgtggat    1260
gcggcattgg aaaccatcag tggcattcgt gccgatctgg gcgccgcgca gaatcgactc    1320
gagtcgacca ttgccaacct gagtacgacc tctgagaacc tttcggccgc gcgttcgcga    1380
attcgtgatg cagactttgc cgccgaatcc gcggaactcg cccgcaccca agtgctccag    1440
caggctggct tgtcggtatt ggcccaggcc aacgcaagac cgcagcaggt tctgcagctg    1500
ctgcagggtg catgccatcc gactgagcct acacgacag tcactactca gaacactgct    1560
tcacaaacaa tgtcggctat tgaaaattta ggtacccatc cgactgagcc ttacacgaca    1620
gtcactactc agaacactgc ttcacaaaca atgtcggcta ttgaaaattt agctagccat    1680
ccgactgagc cttacacgac agtcactact cagaacactg cttcacaaac aatgtcggct    1740
attgaaaatt tactcgagca tccgactgag ccttacacga cagtcactac tcagaacact    1800
gcttcacaaa caatgtcggc tattgaaaat ttacaccatc accatcacca tcaccatcac    1860
cattctagaa aagatgaact gtaa                                           1884
```

<210> SEQ ID NO 6
<211> LENGTH: 626
<212> TYPE: PRT
<213> ORGANISM: Marinobacter algicola (DG893)

```
<220> FEATURE:
<221> NAME/KEY: Flagellin F4DUD
<222> LOCATION: (1)..(626)
<220> FEATURE:
<221> NAME/KEY: CHARACTERISTIC
<222> LOCATION: (506)..(530)
<223> OTHER INFORMATION: DUD epitope
<220> FEATURE:
<221> NAME/KEY: CHARACTERISTIC
<222> LOCATION: (533)..(557)
<223> OTHER INFORMATION: DUD epitope
<220> FEATURE:
<221> NAME/KEY: CHARACTERISTIC
<222> LOCATION: (560)..(584)
<223> OTHER INFORMATION: DUD epitope
<220> FEATURE:
<221> NAME/KEY: CHARACTERISTIC
<222> LOCATION: (587)..(611)
<223> OTHER INFORMATION: DUD epitope
<220> FEATURE:
<221> NAME/KEY: CHARACTERISTIC
<222> LOCATION: (612)..(621)
<223> OTHER INFORMATION: Histidine tail
<220> FEATURE:
<221> NAME/KEY: CHARACTERISTIC
<222> LOCATION: (623)..(626)
<223> OTHER INFORMATION: KDEL sequence

<400> SEQUENCE: 6

Met Pro Gln Ile Ile Asn Thr Asn Ile Ala Ser Leu Asn Ala Gln Arg
1               5                   10                  15

Asn Leu Asn Thr Ser Gln Glu Asp Ser Asn Val Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Lys Gly Leu Asn Gln Ala
    50                  55                  60

Ile Arg Asn Ala Asn Asp Gly Ile Ser Leu Ala Gln Thr Ala Glu Gly
65                  70                  75                  80

Ala Leu Gly Glu Ser Gly Asn Ile Leu Gln Arg Ile Arg Glu Leu Ala
                85                  90                  95

Val Gln Ser Asn Ala Thr Asn Ser Ala Ser Asp Arg Lys Ala Leu Gln
            100                 105                 110

Ser Glu Val Asn Gln Leu Lys Gly Glu Leu Glu Arg Ile Ala Thr Thr
        115                 120                 125

Thr Glu Phe Asn Gly Leu Lys Leu Leu Asp Gly Thr Phe Gln Ala Gln
    130                 135                 140

Lys Phe Gln Ala Gly Ala Asn Glu Asn Gln Ser Ile Ala Val Ser Ile
145                 150                 155                 160

Glu Gly Ala Arg Thr Ala Asp Leu Ala Asn Asn Thr Leu Asp Ala Ala
                165                 170                 175

Asn Ala Thr Leu Asn Gln Gly Thr Gly Ser Thr Thr Ala Ala Asn Ala
            180                 185                 190

Thr Leu Pro Ala Gln Asn Thr Ile Ala Thr Gln Asn Leu Thr Ile Ser
        195                 200                 205

Ser Ser Leu Asp Ser Gln Val Val Pro Ile Thr Ala Gly Asp Thr Ala
    210                 215                 220

Glu Asp Ile Ala Ala Ile Asn Asp Ile Gly Ala Thr Thr Gly Val
225                 230                 235                 240

Asn Ala Thr Ala Arg Thr Ser Ala Thr Leu Ser Asn Thr Ala Thr Thr
                245                 250                 255

Pro Ile Ala Val Pro Gln Thr Val Ser Leu Thr Leu Ser Asn Gly Ser
```

```
            260                 265                 270
Ser Ser Ala Thr Ile Ser Ala Gln Ile Thr Asp Ala Asn Asp Leu Ser
            275                 280                 285
Ala Ile Ala Arg Glu Val Asn Ala Ala Ser Gly Lys Thr Gly Ile Thr
            290                 295                 300
Ala Glu Val Ala Asn Asp Gly Ser Ile Thr Leu Ile Gln Glu Gln Gly
305                 310                 315                 320
Lys Asp Ile Thr Ile Glu Asp Phe Thr Ala Ala Gly Ser Gln Gln Leu
                325                 330                 335
Ala Val Gln Gly Ser Gly Asp Pro Ser Ala Ile Glu Leu Thr Asn Gly
                340                 345                 350
Gly Ala Asn Ala Thr Arg Ile Ala Gly Glu Leu Thr Leu Asp Ser Ser
            355                 360                 365
Val Ser Phe Ala Ala Thr Ser Asp Ala Thr Leu Ala Ala Gly Ser Val
            370                 375                 380
Leu Asn Ser Ala Gln Asn Thr Ala Ala Gly Ser Thr Pro Glu Val
385                 390                 395                 400
Ala Gly Ile Asp Ile Ser Thr Val Asp Gly Ala Thr Ser Ala Leu Ala
                405                 410                 415
Val Val Asp Ala Ala Leu Glu Thr Ile Ser Gly Ile Arg Ala Asp Leu
                420                 425                 430
Gly Ala Ala Gln Asn Arg Leu Glu Ser Thr Ile Ala Asn Leu Ser Thr
            435                 440                 445
Thr Ser Glu Asn Leu Ser Ala Ala Arg Ser Arg Ile Arg Asp Ala Asp
450                 455                 460
Phe Ala Ala Glu Ser Ala Glu Leu Ala Arg Thr Gln Val Leu Gln Gln
465                 470                 475                 480
Ala Gly Leu Ser Val Leu Ala Gln Ala Asn Ala Arg Pro Gln Gln Val
                485                 490                 495
Leu Gln Leu Leu Gln Gly Ala Cys His Pro Thr Glu Pro Tyr Thr Thr
            500                 505                 510
Val Thr Thr Gln Asn Thr Ala Ser Gln Thr Met Ser Ala Ile Glu Asn
            515                 520                 525
Leu Gly Thr His Pro Thr Glu Pro Tyr Thr Thr Val Thr Thr Gln Asn
            530                 535                 540
Thr Ala Ser Gln Thr Met Ser Ala Ile Glu Asn Leu Ala Ser His Pro
545                 550                 555                 560
Thr Glu Pro Tyr Thr Thr Val Thr Thr Gln Asn Thr Ala Ser Gln Thr
                565                 570                 575
Met Ser Ala Ile Glu Asn Leu Leu Glu His Pro Thr Glu Pro Tyr Thr
                580                 585                 590
Thr Val Thr Thr Gln Asn Thr Ala Ser Gln Thr Met Ser Ala Ile Glu
            595                 600                 605
Asn Leu His His His His His His His His Ser Arg Lys Asp
            610                 615                 620
Glu Leu
625

<210> SEQ ID NO 7
<211> LENGTH: 1875
<212> TYPE: DNA
<213> ORGANISM: Marinobacter algicola (DG893)
<220> FEATURE:
<221> NAME/KEY: Flagellin FR4DUD
<222> LOCATION: (1)..(1875)
```

```
<220> FEATURE:
<221> NAME/KEY: characteristic
<222> LOCATION: (1507)..(1581)
<223> OTHER INFORMATION: DUD epitope
<220> FEATURE:
<221> NAME/KEY: characteristic
<222> LOCATION: (1588)..(1662)
<223> OTHER INFORMATION: DUD epitope
<220> FEATURE:
<221> NAME/KEY: characteristic
<222> LOCATION: (1669)..(1743)
<223> OTHER INFORMATION: DUD epitope
<220> FEATURE:
<221> NAME/KEY: characteristic
<222> LOCATION: (1750)..(1824)
<223> OTHER INFORMATION: DUD epitope
<220> FEATURE:
<221> NAME/KEY: characteristic
<222> LOCATION: (1825)..(1854)
<223> OTHER INFORMATION: Sequence that encodes a histidine tail
<220> FEATURE:
<221> NAME/KEY: characteristic
<222> LOCATION: (1861)..(1872)
<223> OTHER INFORMATION: Sequence that encodes the KDEL sequence

<400> SEQUENCE: 7
atggctctcg gtattaacac taacgttgcg tcactgtcag ctcagaacca gctgaacaaa      60
tcccaggagc tttctaacca agctctggag cgtctgtctt ccggtctgcg catcaactcc     120
gccaaggaca tgctgctgg ccttgcaatt tcgacccgtt ttcagtccca gatctctggt     180
ctgaatgttg cccagcgtaa cgccaacgac ggtatttccc tggctcagac tgctgaaggt     240
gctctggaag aaaccaccaa catcctgcag cgcatccgtg agctgtctgt tcagtcggcc     300
aactctacca actcttcttc cgaccgctct gcacttcagg gcgaagtaaa ccagctgaag     360
caagagcttg atcgtattgc cggtaccacc cagtttaacg gcctcaacct tctggatggc     420
agcttcactg cccagtcatt ccaggttggt gccaacgcta accagaccat ctcggtctct     480
gtaactggcg ctcgtggtgc cgaccttggt aacaacaccg tatccggtga agtgatacc      540 actgtcagtc agggcacggg ttctgttgca gtcgcggccg ctgatgtggc aaccgttgcc     600
aacaatacga ttgctacaca gaacataccc gtttctggaa ctgaaggctc tgaggtcatc     660
ggtattaccc agggcgatac tgcagaagcg attgcgctg ctgttaacgc tgaaaccggc     720
acgactggtg taacggctac ggcatccacc acggcaaccc tcgctggtct gtctgacgat     780
ggtacggttt cctttacgct tggcagtggt ggcgacacag cgaccatctc cgcagcggta     840
acgaccactg acctgggtgc gctggccaaa gcgatcaacg atacctcagg caccactggt     900
gttacggctg aagcaaacgg tggcgaaatc acactgaccc aggctgatgg caaagacatc     960
cgtctgcagg actttgccaa ctcaggtaac gcgaccggta ccgccacgct gcagggcagc    1020
ggtgacccat cagcggttac tttgaccgct ggcagcactg acagcacgat tgcttctggc    1080
tctgttgaat cgcctcttc cggtgcattc tcagtaagct cctctgtcgc agagactgcc    1140
ggtagcattc tgaacgtcgc agccgacacc gtggttggtt caacctcca gtcagtgtct    1200 tctatcgaca tcggtactgt tgcgggcgct aacagcgcaa tcgagattgc agatgcggct    1260
ctggagcaga tcagtggtat ccgcgccgat ctgggtgctg cccagaaccg gttcgagtct    1320
acgatcgcca acctgagcac aactgccgaa aacctgtcgg ccgctaacag ccggattctg    1380
gatgcagact tcgcatctga aactgctaag ctgtccaagg cgcaggttct ccagcaagct    1440
ggtatctctg tactggcaca ggcgaatgcc cgtccacagc aggttctgtc cctcctgcag    1500
caattccatc cgactgagcc ttacacgaca gtcactactc agaacactgc ttcacaaaca    1560
```

-continued

```
atgtcggcta ttgaaaattt aggtacccat ccgactgagc cttacacgac agtcactact   1620
cagaacactg cttcacaaac aatgtcggct attgaaaatt tagctagcca tccgactgag   1680
ccttacacga cagtcactac tcagaacact gcttcacaaa caatgtcggc tattgaaaat   1740
ttactcgagc atccgactga gccttacacg acagtcacta ctcagaacac tgcttcacaa   1800
acaatgtcgg ctattgaaaa tttacaccat caccatcacc atcaccatca ccattctaga   1860
aaagatgaac tgtaa                                                    1875
```

```
<210> SEQ ID NO 8
<211> LENGTH: 624
<212> TYPE: PRT
<213> ORGANISM: Marinobacter algicola (DG893)
<220> FEATURE:
<221> NAME/KEY: Flagellin FR4DUD
<222> LOCATION: (1)..(624)
<220> FEATURE:
<221> NAME/KEY: CHARACTERISTIC
<222> LOCATION: (503)..(527)
<223> OTHER INFORMATION: DUD epitope
<220> FEATURE:
<221> NAME/KEY: CHARACTERISTIC
<222> LOCATION: (530)..(554)
<223> OTHER INFORMATION: DUD epitope
<220> FEATURE:
<221> NAME/KEY: CHARACTERISTIC
<222> LOCATION: (557)..(581)
<223> OTHER INFORMATION: DUD epitope
<220> FEATURE:
<221> NAME/KEY: CHARACTERISTIC
<222> LOCATION: (584)..(608)
<223> OTHER INFORMATION: DUD epitope
<220> FEATURE:
<221> NAME/KEY: CHARACTERISTIC
<222> LOCATION: (609)..(618)
<223> OTHER INFORMATION: Histidine tail
<220> FEATURE:
<221> NAME/KEY: CHARACTERISTIC
<222> LOCATION: (621)..(624)
<223> OTHER INFORMATION: KDEL sequence
```

<400> SEQUENCE: 8

```
Met Ala Leu Gly Ile Asn Thr Asn Val Ala Ser Leu Ser Ala Gln Asn
1               5                   10                  15

Gln Leu Asn Lys Ser Gln Glu Leu Ser Asn Gln Ala Leu Glu Arg Leu
            20                  25                  30

Ser Ser Gly Leu Arg Ile Asn Ser Ala Lys Asp Asp Ala Ala Gly Leu
        35                  40                  45

Ala Ile Ser Thr Arg Phe Gln Ser Gln Ile Ser Gly Leu Asn Val Ala
    50                  55                  60

Gln Arg Asn Ala Asn Asp Gly Ile Ser Leu Ala Gln Thr Ala Glu Gly
65                  70                  75                  80

Ala Leu Glu Glu Thr Thr Asn Ile Leu Gln Arg Ile Arg Glu Leu Ser
                85                  90                  95

Val Gln Ser Ala Asn Ser Thr Asn Ser Ser Asp Arg Ser Ala Leu
            100                 105                 110

Gln Gly Glu Val Asn Gln Leu Lys Gln Glu Leu Asp Arg Ile Ala Gly
        115                 120                 125

Thr Thr Gln Phe Asn Gly Leu Asn Leu Leu Asp Gly Ser Phe Thr Ala
    130                 135                 140

Gln Ser Phe Gln Val Gly Ala Asn Ala Asn Gln Thr Ile Ser Val Ser
145                 150                 155                 160

Val Thr Gly Ala Arg Gly Ala Asp Leu Gly Asn Asn Thr Val Ser Gly
                165                 170                 175
```

```
Glu Ser Asp Thr Thr Val Ser Gln Gly Thr Gly Ser Val Ala Val Ala
            180                 185                 190

Ala Ala Asp Val Ala Thr Val Ala Asn Asn Thr Ile Ala Thr Gln Asn
            195                 200                 205

Ile Thr Val Ser Gly Thr Glu Gly Ser Glu Val Ile Gly Ile Thr Gln
210                 215                 220

Gly Asp Thr Ala Glu Ala Ile Ala Ala Val Asn Ala Glu Thr Gly
225                 230                 235                 240

Thr Thr Gly Val Thr Ala Thr Ala Ser Thr Thr Ala Thr Leu Ala Gly
            245                 250                 255

Leu Ser Asp Asp Gly Thr Val Ser Phe Thr Leu Gly Ser Gly Gly Asp
            260                 265                 270

Thr Ala Thr Ile Ser Ala Ala Val Thr Thr Thr Asp Leu Gly Ala Leu
            275                 280                 285

Ala Lys Ala Ile Asn Asp Thr Ser Gly Thr Thr Gly Val Thr Ala Glu
            290                 295                 300

Ala Asn Gly Gly Glu Ile Thr Leu Thr Gln Ala Asp Gly Lys Asp Ile
305                 310                 315                 320

Arg Leu Gln Asp Phe Ala Asn Ser Gly Asn Ala Thr Gly Thr Ala Thr
            325                 330                 335

Leu Gln Gly Ser Gly Asp Pro Ser Ala Val Thr Leu Thr Ala Gly Ser
            340                 345                 350

Thr Asp Ser Thr Ile Ala Ser Gly Ser Val Glu Phe Ala Ser Ser Gly
            355                 360                 365

Ala Phe Ser Val Ser Ser Ser Val Ala Glu Thr Ala Gly Ser Ile Leu
            370                 375                 380

Asn Val Ala Ala Asp Thr Val Val Gly Ser Asn Leu Gln Ser Val Ser
385                 390                 395                 400

Ser Ile Asp Ile Gly Thr Val Ala Gly Ala Asn Ser Ala Ile Glu Ile
            405                 410                 415

Ala Asp Ala Ala Leu Glu Gln Ile Ser Gly Ile Arg Ala Asp Leu Gly
            420                 425                 430

Ala Ala Gln Asn Arg Phe Glu Ser Thr Ile Ala Asn Leu Ser Thr Thr
            435                 440                 445

Ala Glu Asn Leu Ser Ala Ala Asn Ser Arg Ile Leu Asp Ala Asp Phe
450                 455                 460

Ala Ser Glu Thr Ala Lys Leu Ser Lys Ala Gln Val Leu Gln Gln Ala
465                 470                 475                 480

Gly Ile Ser Val Leu Ala Gln Ala Asn Ala Arg Pro Gln Gln Val Leu
            485                 490                 495

Ser Leu Leu Gln Gln Phe His Pro Thr Glu Pro Tyr Thr Thr Val Thr
            500                 505                 510

Thr Gln Asn Thr Ala Ser Gln Thr Met Ser Ala Ile Glu Asn Leu Gly
            515                 520                 525

Thr His Pro Thr Glu Pro Tyr Thr Thr Val Thr Thr Gln Asn Thr Ala
            530                 535                 540

Ser Gln Thr Met Ser Ala Ile Glu Asn Leu Ala Ser His Pro Thr Glu
545                 550                 555                 560

Pro Tyr Thr Thr Val Thr Thr Gln Asn Thr Ala Ser Gln Thr Met Ser
            565                 570                 575

Ala Ile Glu Asn Leu Leu Glu His Pro Thr Glu Pro Tyr Thr Thr Val
            580                 585                 590
```

Thr Thr Gln Asn Thr Ala Ser Gln Thr Met Ser Ala Ile Glu Asn Leu
        595                 600                 605

His His His His His His His His His Ser Arg Lys Asp Glu Leu
    610                 615                 620

<210> SEQ ID NO 9
<211> LENGTH: 1893
<212> TYPE: DNA
<213> ORGANISM: Salmonella typhimurium
<220> FEATURE:
<221> NAME/KEY: Flagellin STF4DUD
<222> LOCATION: (1)..(1893)
<220> FEATURE:
<221> NAME/KEY: characteristic
<222> LOCATION: (1525)..(1599)
<223> OTHER INFORMATION: DUD epitope
<220> FEATURE:
<221> NAME/KEY: characteristic
<222> LOCATION: (1606)..(1680)
<223> OTHER INFORMATION: DUD epitope
<220> FEATURE:
<221> NAME/KEY: characteristic
<222> LOCATION: (1686)..(1761)
<223> OTHER INFORMATION: DUD epitope
<220> FEATURE:
<221> NAME/KEY: characteristic
<222> LOCATION: (1768)..(1842)
<223> OTHER INFORMATION: DUD epitope
<220> FEATURE:
<221> NAME/KEY: characteristic
<222> LOCATION: (1843)..(1872)
<223> OTHER INFORMATION: Sequence that encodes a histidine tail
<220> FEATURE:
<221> NAME/KEY: characteristic
<222> LOCATION: (1889)..(1890)
<223> OTHER INFORMATION: Sequence that encodes the KDEL sequence

<400> SEQUENCE: 9

| | | | | | |
|---|---|---|---|---|---|
| atggcacaag | taatcaacac | taacagtctg | tcgctgctga | cccagaataa | cctgaacaaa | 60 |
| tcccagtccg | cactgggcac | cgctatcgag | cgtctgtctt | ctggtctgcg | tatcaacagc | 120 |
| gcgaaagacg | atgcggcagg | tcaggcgatt | gctaaccgtt | tcaccgcgaa | catcaaaggt | 180 |
| ctgactcagg | cttcccgtaa | cgctaacgac | ggtatctcca | ttgcgcagac | cactgaaggc | 240 |
| gcgctgaacg | aaatcaacaa | caacctgcag | cgtgtgcgtg | aactggcggt | tcagtctgct | 300 |
| aacagcacca | actcccagtc | tgacctcgac | tccatccagg | ctgaaatcac | ccagcgcctg | 360 |
| aacgaaatcg | accgtgtatc | cggccagact | cagttcaacg | gcgtgaaagt | cctggcgcag | 420 |
| gacaacaccc | tgaccatcca | ggttggcgcc | aacgacggtg | aaactatcga | tatcgatctg | 480 |
| aagcagatca | actctcagac | cctgggtctg | gactcactga | acgtgcagaa | agcgtatgat | 540 |
| gtgaaagata | cagcagtaac | aacgaaagct | tatgccaata | atggtactac | actggatgta | 600 |
| tcgggtcttg | atgatgcagc | tattaaagcg | gctacgggtg | gtacgaatgg | tacggcttct | 660 |
| gtaaccggtg | gtgcggttaa | atttgacgca | gataataaca | agtactttgt | tactattggt | 720 |
| ggctttactg | gtgctgatgc | cgccaaaaat | ggcgattatg | aagttaacgt | tgctactgac | 780 |
| ggtacagtaa | cccttgcggc | tggcgcaact | aagaccacaa | tgcctgctgg | tgcgacaact | 840 |
| aaaacagaag | tacaggagtt | aaaagatacc | ccggcagttg | tttcagcaga | tgctaaaaat | 900 |
| gccttaattg | ctgcggcgt | tgacgctacc | gatgctaatg | cgctgagtt | ggtcaaaatg | 960 |
| tcttataccg | ataaaaatgg | taagacaatt | gaaggcggtt | atgcgcttaa | agctggcgat | 1020 |
| aagtattacg | ccgcagatta | cgatgaagcg | acaggagcaa | ttaaagctaa | aaccacaagt | 1080 |
| tatactgctg | ctgacggcac | taccaaaaca | gcggctaacc | aactgggtgg | cgtagacggt | 1140 |

```
aaaaccgaag tcgttactat cgacggtaaa acctacaatg ccagcaaagc cgctggtcat    1200
gatttcaaag cacaaccaga gctggcggaa gcagccgcta aaaccaccga aaacccgctg    1260
cagaaaattg atgccgcgct ggcgcaggtg gatgcgctgc gctctgatct gggtgcggta    1320
caaaaccgtt tcaactctgc tatcaccaac ctgggcaata ccgtaaacaa tctgtctgaa    1380
gcgcgtagcc gtatcgaaga ttccgactac gcgaccgaag tttccaacat gtctcgcgcg    1440
cagattctgc agcaggccgg tacttccgtt ctggcgcagg ctaaccaggt cccgcagaac    1500
gtgctgtctc tgttacgtga attccatccg actgagcctt acacgacagt cactactcag    1560
aacactgctt cacaaacaat gtcggctatt gaaaatttag gtaccatccc gactgagcct    1620
tacacgacag tcactactca gaacactgct tcacaaacaa tgtcggctat tgaaaattta    1680
gctagccatc cgactgagcc ttacacgaca gtcactactc agaacactgc ttcacaaaca    1740
atgtcggcta ttgaaaattt actcgagcat ccgactgagc cttacacgac agtcactact    1800
cagaacactg cttcacaaac aatgtcggct attgaaaatt tacaccatca ccatcaccat    1860
caccatcacc attctagaaa agatgaactg taa                                 1893
```

<210> SEQ ID NO 10
<211> LENGTH: 630
<212> TYPE: PRT
<213> ORGANISM: Salmonella typhimurium
<220> FEATURE:
<221> NAME/KEY: Flagellin STF4DUD
<222> LOCATION: (1)..(630)
<220> FEATURE:
<221> NAME/KEY: CHARACTERISTIC
<222> LOCATION: (509)..(533)
<223> OTHER INFORMATION: DUD epitope
<220> FEATURE:
<221> NAME/KEY: CHARACTERISTIC
<222> LOCATION: (536)..(560)
<223> OTHER INFORMATION: DUD epitope
<220> FEATURE:
<221> NAME/KEY: CHARACTERISTIC
<222> LOCATION: (563)..(587)
<223> OTHER INFORMATION: DUD epitope
<220> FEATURE:
<221> NAME/KEY: CHARACTERISTIC
<222> LOCATION: (590)..(614)
<223> OTHER INFORMATION: DUD epitope
<220> FEATURE:
<221> NAME/KEY: CHARACTERISTIC
<222> LOCATION: (615)..(624)
<223> OTHER INFORMATION: Histidine tail
<220> FEATURE:
<221> NAME/KEY: CHARACTERISTIC
<222> LOCATION: (627)..(630)
<223> OTHER INFORMATION: KDEL sequence

<400> SEQUENCE: 10

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

```
Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
        180                 185                 190

Asn Asn Gly Thr Thr Leu Asp Val Ser Gly Leu Asp Asp Ala Ala Ile
    195                 200                 205

Lys Ala Ala Thr Gly Gly Thr Asn Gly Thr Ala Ser Val Thr Gly Gly
210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
        260                 265                 270

Thr Met Pro Ala Gly Ala Thr Thr Lys Thr Glu Val Gln Glu Leu Lys
    275                 280                 285

Asp Thr Pro Ala Val Val Ser Ala Asp Ala Lys Asn Ala Leu Ile Ala
290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
                325                 330                 335

Lys Ala Gly Asp Lys Tyr Tyr Ala Ala Asp Tyr Asp Glu Ala Thr Gly
        340                 345                 350

Ala Ile Lys Ala Lys Thr Thr Ser Tyr Thr Ala Ala Asp Gly Thr Thr
    355                 360                 365

Lys Thr Ala Ala Asn Gln Leu Gly Gly Val Asp Gly Lys Thr Glu Val
370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
        420                 425                 430

Leu Arg Ser Asp Leu Gly Ala Val Gln Asn Arg Phe Asn Ser Ala Ile
    435                 440                 445

Thr Asn Leu Gly Asn Thr Val Asn Asn Leu Ser Glu Ala Arg Ser Arg
450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg Glu Phe His Pro Thr Glu
        500                 505                 510

Pro Tyr Thr Thr Val Thr Thr Gln Asn Thr Ala Ser Gln Thr Met Ser
```

```
                515                 520                 525
Ala Ile Glu Asn Leu Gly Thr His Pro Thr Glu Pro Tyr Thr Thr Val
        530                 535                 540

Thr Thr Gln Asn Thr Ala Ser Gln Thr Met Ser Ala Ile Glu Asn Leu
545                 550                 555                 560

Ala Ser His Pro Thr Glu Pro Tyr Thr Thr Val Thr Thr Gln Asn Thr
                565                 570                 575

Ala Ser Gln Thr Met Ser Ala Ile Glu Asn Leu Leu Glu His Pro Thr
            580                 585                 590

Glu Pro Tyr Thr Thr Val Thr Thr Gln Asn Thr Ala Ser Gln Thr Met
        595                 600                 605

Ser Ala Ile Glu Asn Leu His His His His His His His His
    610                 615                 620

Ser Arg Lys Asp Glu Leu
625                 630

<210> SEQ ID NO 11
<211> LENGTH: 29
<212> TYPE: DNA
<213> ORGANISM: Salmonella typhimurium

<400> SEQUENCE: 11
gccggatcca tggcacaagt aatcaacac                                          29

<210> SEQ ID NO 12
<211> LENGTH: 27
<212> TYPE: DNA
<213> ORGANISM: Salmonella typhimurium

<400> SEQUENCE: 12
gcggaattca cgtaacagag acagcac                                            27

<210> SEQ ID NO 13
<211> LENGTH: 13
<212> TYPE: PRT
<213> ORGANISM: African swine fever virus (ASF)
<220> FEATURE:
<221> NAME/KEY: CHARACTERISTIC
<222> LOCATION: (1)..(13)
<223> OTHER INFORMATION: DCL8-dynein-binding domain of protein p54

<400> SEQUENCE: 13

Tyr Thr Thr Val Thr Thr Gln Asn Thr Ala Ser Gln Thr
1               5                   10

<210> SEQ ID NO 14
<211> LENGTH: 25
<212> TYPE: PRT
<213> ORGANISM: African swine fever virus (ASF)
<220> FEATURE:
<221> NAME/KEY: CHARACTERISTIC
<222> LOCATION: (1)..(25)
<223> OTHER INFORMATION: Modified peptide from the dynein-binding area
      of protein p54 (modified DUD)
<220> FEATURE:
<221> NAME/KEY: CHARACTERISTIC
<222> LOCATION: (1)..(5)
<223> OTHER INFORMATION: Sequence of amino acids added to the 5-end
<220> FEATURE:
<221> NAME/KEY: CHARACTERISTIC
<222> LOCATION: (19)..(25)
<223> OTHER INFORMATION: Sequence of amino acids added to the 3-end

<400> SEQUENCE: 14
```

His Pro Thr Glu Pro Tyr Thr Thr Val Thr Thr Gln Asn Thr Ala Ser
1               5                   10                  15

Gln Thr Met Ser Ala Ile Glu Asn Leu
            20                  25

<210> SEQ ID NO 15
<211> LENGTH: 495
<212> TYPE: PRT
<213> ORGANISM: Salmonella typhimurium
<220> FEATURE:
<221> NAME/KEY: Flagellin STF
<222> LOCATION: (1)..(495)

<400> SEQUENCE: 15

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

```
Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 16
<211> LENGTH: 15
<212> TYPE: PRT
<213> ORGANISM: Marinobacter algicola (DG893)
<220> FEATURE:
<221> NAME/KEY: Interaction sequence of flagellin FR with TLR5
<222> LOCATION: (1)..(15)

<400> SEQUENCE: 16

Asn Ile Leu Gln Arg Ile Arg Glu Leu Ser Val Gln Ser Ala Asn
1               5                   10                  15

<210> SEQ ID NO 17
<211> LENGTH: 15
<212> TYPE: PRT
<213> ORGANISM: Marinobacter algicola (DG893)
<220> FEATURE:
<221> NAME/KEY: Interaction sequence of flagellin F with TLR5
<222> LOCATION: (1)..(15)

<400> SEQUENCE: 17

Asn Ile Leu Gln Arg Ile Arg Glu Leu Ala Val Gln Ser Ala Asn
1               5                   10                  15

<210> SEQ ID NO 18
<211> LENGTH: 17
<212> TYPE: PRT
<213> ORGANISM: Marinobacter algicola (DG893)
<220> FEATURE:
<221> NAME/KEY: Amplified interaction sequence of flagellin F with TLR5
<222> LOCATION: (1)..(17)

<400> SEQUENCE: 18

Asn Ile Leu Gln Arg Ile Arg Glu Leu Ala Val Gln Ser Ala Asn Ala
1               5                   10                  15

Thr

<210> SEQ ID NO 19
<211> LENGTH: 1512
<212> TYPE: DNA
```

```
<213> ORGANISM: Marinobacter algicola (DG893)
<220> FEATURE:
<221> NAME/KEY: Flagellin F
<222> LOCATION: (1)..(1512)

<400> SEQUENCE: 19
```

| | | |
|---|---|---|
| atgcctcaga tcatcaacac caatattgcg tcgctgaatg cacagcgaaa cctgaatact | 60 |
| tcgcaggaag actccaacgt tgccctgcag cgactgtcat ccggcctgcg tatcaactcc | 120 |
| gccaaggacg acgccgccgg actggccatc tccgagcgat tcacatcgca gatcaaaggt | 180 |
| ctcaaccagg ccattcgaaa cgccaatgac ggtatttccc tggctcagac cgccgaaggc | 240 |
| gccctgggcg aatccggaaa catcctgcag cgcatccggg aactcgccgt acagtccgcc | 300 |
| aacgctacca actccgcatc tgacaggaag gccctgcagt ctgaagtaaa ccagctaaaa | 360 |
| ggtgagctcg agcgcattgc caccaccacc gaattcaacg gactgaaact tctggacggc | 420 |
| accttccagg ctcagaagtt ccaggctggc gccaacgaaa accagagcat cgccgtttcc | 480 |
| atcgaaggtg cccgaaccgc cgacctagca acaacacgc tcgacgctgc caacgcaacc | 540 |
| ctgaaccagg gcaccggttc aacaacggca gcgaatgcga cgttacccgc acaaaacacg | 600 |
| atcgccacgc agaatctcac catttccagc tcgctggaca gccaggtggt gcccattaca | 660 |
| gcaggtgaca cagcggaaga catcgccgca gccatcaacg acattggtgc cacgacgggt | 720 |
| gtgaacgcaa cggcaagaac atcggcgacc ctgagcaaca ccgctaccac gccaatcgcc | 780 |
| gtgcctcaaa ccgtatcgct cacgctttcc aacggtagca gttcagcaac catttccgcg | 840 |
| cagatcaccg atgcgaacga cctctcagca attgcacgtg aggtgaacgc agcttccggc | 900 |
| aagaccggca ttaccgcgga agtcgctaac gacggcagca tcacgctgat tcaggagcaa | 960 |
| ggtaaagaca tcactattga agactttacc gcagcgggct ctcagcaact ggcggtacag | 1020 |
| ggtagtggcg atccaagtgc catcgaactg acaaacggtg gtgccaatgc acacgtatc | 1080 |
| gccggggaat tgacactgga ctcctccgtt agcttcgcgg cgacgtctga cgccaccctg | 1140 |
| gccgcaggca gcgttctgaa cagtgcacag aataccgccg ccggctccac acctgaagaa | 1200 |
| gtggcaggta ttgatataag caccgttgac ggcgcaacca gtgcacttgc agttgtggat | 1260 |
| gcggcattgg aaaccatcag tggcattcgt gccgatctgg gcgccgcgca gaatcgactc | 1320 |
| gagtcgacca ttgccaacct gagtacgacc tctgagaacc tttcggccgc gcgttcgcga | 1380 |
| attcgtgatg cagactttgc cgccgaatcc gcggaactcg cccgcaccca agtgctccag | 1440 |
| caggctggct tgtcggtatt ggcccaggcc aacgcaagac cgcagcaggt tctgcagctg | 1500 |
| ctgcagggtt aa | 1512 |

```
<210> SEQ ID NO 20
<211> LENGTH: 503
<212> TYPE: PRT
<213> ORGANISM: Marinobacter algicola (DG893)
<220> FEATURE:
<221> NAME/KEY: Flagellin F
<222> LOCATION: (1)..(503)

<400> SEQUENCE: 20

Met Pro Gln Ile Ile Asn Thr Asn Ile Ala Ser Leu Asn Ala Gln Arg
1               5                   10                  15

Asn Leu Asn Thr Ser Gln Glu Asp Ser Asn Val Ala Leu Gln Arg Leu
            20                  25                  30

Ser Ser Gly Leu Arg Ile Asn Ser Ala Lys Asp Asp Ala Ala Gly Leu
        35                  40                  45
```

```
Ala Ile Ser Glu Arg Phe Thr Ser Gln Ile Lys Gly Leu Asn Gln Ala
 50                  55                  60

Ile Arg Asn Ala Asn Asp Gly Ile Ser Leu Ala Gln Thr Ala Glu Gly
 65                  70                  75                  80

Ala Leu Gly Glu Ser Gly Asn Ile Leu Gln Arg Ile Arg Glu Leu Ala
                 85                  90                  95

Val Gln Ser Ala Asn Ala Thr Asn Ser Ala Ser Asp Arg Lys Ala Leu
            100                 105                 110

Gln Ser Glu Val Asn Gln Leu Lys Gly Glu Leu Glu Arg Ile Ala Thr
            115                 120                 125

Thr Thr Glu Phe Asn Gly Leu Lys Leu Leu Asp Gly Thr Phe Gln Ala
130                 135                 140

Gln Lys Phe Gln Ala Gly Ala Asn Glu Asn Gln Ser Ile Ala Val Ser
145                 150                 155                 160

Ile Glu Gly Ala Arg Thr Ala Asp Leu Ala Asn Asn Thr Leu Asp Ala
                165                 170                 175

Ala Asn Ala Thr Leu Asn Gln Gly Thr Gly Ser Thr Thr Ala Ala Asn
            180                 185                 190

Ala Thr Leu Pro Ala Gln Asn Thr Ile Ala Thr Gln Asn Leu Thr Ile
            195                 200                 205

Ser Ser Ser Leu Asp Ser Gln Val Val Pro Ile Thr Ala Gly Asp Thr
210                 215                 220

Ala Glu Asp Ile Ala Ala Ile Asn Asp Ile Gly Ala Thr Thr Gly
225                 230                 235                 240

Val Asn Ala Thr Ala Arg Thr Ser Ala Thr Leu Ser Asn Thr Ala Thr
                245                 250                 255

Thr Pro Ile Ala Val Pro Gln Thr Val Ser Leu Thr Leu Ser Asn Gly
            260                 265                 270

Ser Ser Ser Ala Thr Ile Ser Ala Gln Ile Thr Asp Ala Asn Asp Leu
            275                 280                 285

Ser Ala Ile Ala Arg Glu Val Asn Ala Ala Ser Gly Lys Thr Gly Ile
290                 295                 300

Thr Ala Glu Val Ala Asn Asp Gly Ser Ile Thr Leu Ile Gln Glu Gln
305                 310                 315                 320

Gly Lys Asp Ile Thr Ile Glu Asp Phe Thr Ala Ala Gly Ser Gln Gln
                325                 330                 335

Leu Ala Val Gln Gly Ser Gly Asp Pro Ser Ala Ile Glu Leu Thr Asn
            340                 345                 350

Gly Gly Ala Asn Ala Thr Arg Ile Ala Gly Glu Leu Thr Leu Asp Ser
            355                 360                 365

Ser Val Ser Phe Ala Ala Thr Ser Asp Ala Thr Leu Ala Ala Gly Ser
370                 375                 380

Val Leu Asn Ser Ala Gln Asn Thr Ala Ala Gly Ser Thr Pro Glu Glu
385                 390                 395                 400

Val Ala Gly Ile Asp Ile Ser Thr Val Asp Gly Ala Thr Ser Ala Leu
                405                 410                 415

Ala Val Val Asp Ala Ala Leu Glu Thr Ile Ser Gly Ile Arg Ala Asp
            420                 425                 430

Leu Gly Ala Ala Gln Asn Arg Leu Glu Ser Thr Ile Ala Asn Leu Ser
            435                 440                 445

Thr Thr Ser Glu Asn Leu Ser Ala Ala Arg Ser Arg Ile Arg Asp Ala
450                 455                 460

Asp Phe Ala Ala Glu Ser Ala Glu Leu Ala Arg Thr Gln Val Leu Gln
```

465             470             475             480
Gln Ala Gly Leu Ser Val Leu Ala Gln Ala Asn Ala Arg Pro Gln Gln
                485             490             495

Val Leu Gln Leu Leu Gln Gly
            500

<210> SEQ ID NO 21
<211> LENGTH: 1503
<212> TYPE: DNA
<213> ORGANISM: Marinobacter algicola (DG893)
<220> FEATURE:
<221> NAME/KEY: Flagellin FR
<222> LOCATION: (1)..(1503)

<400> SEQUENCE: 21

| | | | | | | |
|---|---|---|---|---|---|---|
| atggctctcg | gtattaacac | taacgttgcg | tcactgtcag | ctcagaacca | gctgaacaaa | 60 |
| tcccaggagc | tttctaacca | agctctggag | cgtctgtctt | ccggtctgcg | catcaactcc | 120 |
| gccaaggacg | atgctgctgg | ccttgcaatt | tcgacccgtt | ttcagtccca | gatctctggt | 180 |
| ctgaatgttg | cccagcgtaa | cgccaacgac | ggtatttccc | tggctcagac | tgctgaaggt | 240 |
| gctctggaag | aaaccaccaa | catcctgcag | cgcatccgtg | agctgtctgt | tcagtcggcc | 300 |
| aactctacca | actcttcttc | cgaccgctct | gcacttcagg | gcgaagtaaa | ccagctgaag | 360 |
| caagagcttg | atcgtattgc | cggtaccacc | cagtttaacg | gcctcaacct | tctggatggc | 420 |
| agcttcactg | cccagtcatt | ccaggttggt | gccaacgcta | accagaccat | ctcggtctct | 480 |
| gtaactggcg | ctcgtggtgc | cgaccttggt | aacaacaccg | tatccggtga | aagtgatacc | 540 |
| actgtcagtc | agggcacggg | ttctgttgca | gtcgcggccg | ctgatgtggc | aaccgttgcc | 600 |
| aacaatacga | ttgctacaca | gaacatcacc | gtttctggaa | ctgaaggctc | tgaggtcatc | 660 |
| ggtattaccc | agggcgatac | tgcagaagcg | attgcggctg | ctgttaacgc | tgaaaccggc | 720 |
| acgactggtg | taacggctac | ggcatccacc | acggcaaccc | tcgctggtct | gtctgacgat | 780 |
| ggtacggttt | cctttacgct | tggcagtggt | ggcgacacag | cgaccatctc | cgcagcggta | 840 |
| acgaccactg | acctgggtgc | gctggccaaa | gcgatcaacg | atacctcagg | caccactggt | 900 |
| gttacggctg | aagcaaacgg | tggcgaaatc | acactgaccc | aggctgatgg | caaagacatc | 960 |
| cgtctgcagg | actttgccaa | ctcaggtaac | gcgaccggta | ccgccacgct | gcagggcagc | 1020 |
| ggtgacccat | cagcggttac | tttgaccgct | ggcagcactg | cagcacgat | tgcttctggc | 1080 |
| tctgttgaat | cgcctcttc | cggtgcattc | tcagtaagct | cctctgtcgc | agagactgcc | 1140 |
| ggtagcattc | tgaacgtcgc | agccgacacc | gtggttggtt | ccaacctcca | gtcagtgtct | 1200 |
| tctatcgaca | tcggtactgt | tgcgggcgct | aacagcgcaa | tcgagattgc | agatgcggct | 1260 |
| ctggagcaga | tcagtggtat | ccgcgccgat | ctgggtgctg | cccagaaccg | gttcgagtct | 1320 |
| acgatcgcca | acctgagcac | aactgccgaa | aacctgtcgg | ccgctaacag | ccggattctg | 1380 |
| gatgcagact | tcgcatctga | aactgctaag | ctgtccaagg | cgcaggttct | ccagcaagct | 1440 |
| ggtatctctg | tactggcaca | ggcgaatgcc | cgtccacagc | aggttctgtc | cctcctgcag | 1500 |
| taa | | | | | | 1503 |

<210> SEQ ID NO 22
<211> LENGTH: 500
<212> TYPE: PRT
<213> ORGANISM: Marinobacter algicola (DG893)
<220> FEATURE:
<221> NAME/KEY: Flagellin FR
<222> LOCATION: (1)..(500)

-continued

```
<400> SEQUENCE: 22

Met Ala Leu Gly Ile Asn Thr Asn Val Ala Ser Leu Ser Ala Gln Asn
1               5                   10                  15

Gln Leu Asn Lys Ser Gln Glu Leu Ser Asn Gln Ala Leu Glu Arg Leu
            20                  25                  30

Ser Ser Gly Leu Arg Ile Asn Ser Ala Lys Asp Asp Ala Ala Gly Leu
        35                  40                  45

Ala Ile Ser Thr Arg Phe Gln Ser Gln Ile Ser Gly Leu Asn Val Ala
    50                  55                  60

Gln Arg Asn Ala Asn Asp Gly Ile Ser Leu Ala Gln Thr Ala Glu Gly
65                  70                  75                  80

Ala Leu Glu Glu Thr Thr Asn Ile Leu Gln Arg Ile Arg Glu Leu Ser
                85                  90                  95

Val Gln Ser Ala Asn Ser Thr Asn Ser Ser Asp Arg Ser Ala Leu
            100                 105                 110

Gln Gly Glu Val Asn Gln Leu Lys Gln Glu Leu Asp Arg Ile Ala Gly
        115                 120                 125

Thr Thr Gln Phe Asn Gly Leu Asn Leu Leu Asp Gly Ser Phe Thr Ala
130                 135                 140

Gln Ser Phe Gln Val Gly Ala Asn Ala Asn Gln Thr Ile Ser Val Ser
145                 150                 155                 160

Val Thr Gly Ala Arg Gly Ala Asp Leu Gly Asn Asn Thr Val Ser Gly
                165                 170                 175

Glu Ser Asp Thr Thr Val Ser Gln Gly Thr Gly Ser Val Ala Val Ala
            180                 185                 190

Ala Ala Asp Val Ala Thr Val Ala Asn Asn Thr Ile Ala Thr Gln Asn
        195                 200                 205

Ile Thr Val Ser Gly Thr Glu Gly Ser Glu Val Ile Gly Ile Thr Gln
    210                 215                 220

Gly Asp Thr Ala Glu Ala Ile Ala Ala Val Asn Ala Glu Thr Gly
225                 230                 235                 240

Thr Thr Gly Val Thr Ala Thr Ala Ser Thr Thr Ala Thr Leu Ala Gly
                245                 250                 255

Leu Ser Asp Asp Gly Thr Val Ser Phe Thr Leu Gly Ser Gly Gly Asp
            260                 265                 270

Thr Ala Thr Ile Ser Ala Ala Val Thr Thr Asp Leu Gly Ala Leu
        275                 280                 285

Ala Lys Ala Ile Asn Asp Thr Ser Gly Thr Thr Gly Val Thr Ala Glu
    290                 295                 300

Ala Asn Gly Gly Glu Ile Thr Leu Thr Gln Ala Asp Gly Lys Asp Ile
305                 310                 315                 320

Arg Leu Gln Asp Phe Ala Asn Ser Gly Asn Ala Thr Gly Thr Ala Thr
                325                 330                 335

Leu Gln Gly Ser Gly Asp Pro Ser Ala Val Thr Leu Thr Ala Gly Ser
            340                 345                 350

Thr Asp Ser Thr Ile Ala Ser Gly Ser Val Glu Phe Ala Ser Ser Gly
        355                 360                 365

Ala Phe Ser Val Ser Ser Ser Val Ala Glu Thr Gly Ser Ile Leu
    370                 375                 380

Asn Val Ala Ala Asp Thr Val Val Gly Ser Asn Leu Gln Ser Val Ser
385                 390                 395                 400

Ser Ile Asp Ile Gly Thr Val Ala Gly Ala Asn Ser Ala Ile Glu Ile
```

```
                405                 410                 415
Ala Asp Ala Ala Leu Glu Gln Ile Ser Gly Ile Arg Ala Asp Leu Gly
        420                 425                 430

Ala Ala Gln Asn Arg Phe Glu Ser Thr Ile Ala Asn Leu Ser Thr Thr
    435                 440                 445

Ala Glu Asn Leu Ser Ala Ala Asn Ser Arg Ile Leu Asp Ala Asp Phe
450                 455                 460

Ala Ser Glu Thr Ala Lys Leu Ser Lys Ala Gln Val Leu Gln Gln Ala
465                 470                 475                 480

Gly Ile Ser Val Leu Ala Gln Ala Asn Ala Arg Pro Gln Gln Val Leu
                485                 490                 495

Ser Leu Leu Gln
        500

<210> SEQ ID NO 23
<211> LENGTH: 1836
<212> TYPE: DNA
<213> ORGANISM: Marinobacter algicola (DG893)
<220> FEATURE:
<221> NAME/KEY: Flagellin F4DUD
<222> LOCATION: (1)..(1836)
<220> FEATURE:
<221> NAME/KEY: characteristic
<222> LOCATION: (1516)..(1590)
<223> OTHER INFORMATION: DUD epitope
<220> FEATURE:
<221> NAME/KEY: characteristic
<222> LOCATION: (1597)..(1671)
<223> OTHER INFORMATION: DUD epitope
<220> FEATURE:
<221> NAME/KEY: characteristic
<222> LOCATION: (1678)..(1752)
<223> OTHER INFORMATION: DUD epitope
<220> FEATURE:
<221> NAME/KEY: characteristic
<222> LOCATION: (1759)..(1833)
<223> OTHER INFORMATION: DUD epitope

<400> SEQUENCE: 23
atgcctcaga tcatcaacac caatattgcg tcgctgaatg cacagcgaaa cctgaatact      60
tcgcaggaag actccaacgt tgccctgcag cgactgtcat ccggcctgcg tatcaactcc     120
gccaaggacg acgccgccgg actggccatc tccgagcgat tcacatcgca gatcaaaggt     180
ctcaaccagg ccattcgaaa cgccaatgac ggtatttccc tggctcagac cgccgaaggc     240
gccctgggcg aatccggaaa catcctgcag cgcatccggg aactcgccgt acagtccgcc     300
aacgctacca actccgcatc tgacaggaag gccctgcagt ctgaagtaaa ccagctaaaa     360
ggtgagctcg agcgcattgc caccaccacc gaattcaacg gactgaaact tctggacggc     420
accttccagg ctcagaagtt ccaggctggc gccaacgaaa accagagcat cgccgttccc     480
atcgaaggtg cccgaaccgc cgacctagca acaacacgc tcgacgctgc caacgcaacc     540
ctgaaccagg gcaccggttc aacaacggca gcgaatgcga cgttacccgc acaaaacacg     600
atcgccacgc agaatctcac catttccagc tcgctggaca gccaggtggt gcccattaca     660
gcaggtgaca cagcggaaga catcgccgca gccatcaacg acattggtgc cacgacgggt     720
gtgaacgcaa cggcaagaac atcggcgacc ctgagcaaca ccgctaccac gccaatcgcc     780
gtgcctcaaa ccgtatcgct cacgcttttcc aacggtagca gttcagcaac catttccgcg     840
cagatcaccg atgcgaacga cctctcagca attgcacgtg aggtgaacgc agcttccggc     900
aagaccggca ttaccgcgga agtcgctaac gacggcagca tcacgctgat tcaggagcaa     960
```

```
ggtaaagaca tcactattga agactttacc gcagcgggct ctcagcaact ggcggtacag    1020
ggtagtggcg atccaagtgc catcgaactg acaaacggtg gtgccaatgc cacacgtatc    1080
gccggggaat tgacactgga ctcctccgtt agcttcgcgg cgacgtctga cgccaccctg    1140
gccgcaggca gcgttctgaa cagtgcacag aataccgccg ccggctccac acctgaagaa    1200
gtggcaggta ttgatataag caccgttgac ggcgcaacca gtgcacttgc agttgtggat    1260
gcggcattgg aaaccatcag tggcattcgt gccgatctgg gcgccgcgca gaatcgactc    1320
gagtcgacca ttgccaacct gagtacgacc tctgagaacc tttcggccgc gcgttcgcga    1380
attcgtgatg cagactttgc cgccgaatcc gcggaactcg cccgcaccca gtgctccag    1440 caggctggct tgtcggtatt ggcccaggcc aacgcaagac cgcagcaggt tctgcagctg    1500
ctgcagggtg catgccatcc gactgagcct tacacgacag tcactactca gaacactgct    1560
tcacaaacaa tgtcggctat tgaaaattta ggtacccatc cgactgagcc ttacacgaca    1620
gtcactactc agaacactgc ttcacaaaca atgtcggcta ttgaaaattt agctagccat    1680
ccgactgagc cttacacgac agtcactact cagaacactg cttcacaaac aatgtcggct    1740
attgaaaatt tactcgagca tccgactgag ccttacacga cagtcactac tcagaacact    1800
gcttcacaaa caatgtcggc tattgaaaat ttataa                              1836

<210> SEQ ID NO 24
<211> LENGTH: 610
<212> TYPE: PRT
<213> ORGANISM: Marinobacter algicola (DG893)
<220> FEATURE:
<221> NAME/KEY: Flagellin F4DUD
<222> LOCATION: (1)..(610)
<220> FEATURE:
<221> NAME/KEY: CHARACTERISTIC
<222> LOCATION: (506)..(530)
<223> OTHER INFORMATION: DUD epitope
<220> FEATURE:
<221> NAME/KEY: CHARACTERISTIC
<222> LOCATION: (533)..(557)
<223> OTHER INFORMATION: DUD epitope
<220> FEATURE:
<221> NAME/KEY: CHARACTERISTIC
<222> LOCATION: (560)..(584)
<223> OTHER INFORMATION: DUD epitope
<220> FEATURE:
<221> NAME/KEY: CHARACTERISTIC
<222> LOCATION: (587)..(610)
<223> OTHER INFORMATION: DUD epitope

<400> SEQUENCE: 24

Met Pro Gln Ile Ile Asn Thr Asn Ile Ala Ser Leu Asn Ala Gln Arg
1               5                   10                  15

Asn Leu Asn Thr Ser Gln Glu Asp Ser Asn Val Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Lys Gly Leu Asn Gln Ala
    50                  55                  60

Ile Arg Asn Ala Asn Asp Gly Ile Ser Leu Ala Gln Thr Ala Glu Gly
65                  70                  75                  80

Ala Leu Gly Glu Ser Gly Asn Ile Leu Gln Arg Ile Arg Glu Leu Ala
                85                  90                  95

Val Gln Ser Asn Ala Thr Asn Ser Ala Ser Asp Arg Lys Ala Leu Gln
            100                 105                 110

Ser Glu Val Asn Gln Leu Lys Gly Glu Leu Glu Arg Ile Ala Thr Thr
```

```
            115                 120                 125
Thr Glu Phe Asn Gly Leu Lys Leu Leu Asp Gly Thr Phe Gln Ala Gln
            130                 135                 140
Lys Phe Gln Ala Gly Ala Asn Glu Asn Gln Ser Ile Ala Val Ser Ile
145                 150                 155                 160
Glu Gly Ala Arg Thr Ala Asp Leu Ala Asn Asn Thr Leu Asp Ala Ala
                165                 170                 175
Asn Ala Thr Leu Asn Gln Gly Thr Gly Ser Thr Thr Ala Ala Asn Ala
                180                 185                 190
Thr Leu Pro Ala Gln Asn Thr Ile Ala Thr Gln Asn Leu Thr Ile Ser
                195                 200                 205
Ser Ser Leu Asp Ser Gln Val Val Pro Ile Thr Ala Gly Asp Thr Ala
            210                 215                 220
Glu Asp Ile Ala Ala Ala Ile Asn Asp Ile Gly Ala Thr Thr Gly Val
225                 230                 235                 240
Asn Ala Thr Ala Arg Thr Ser Ala Thr Leu Ser Asn Thr Ala Thr Thr
                245                 250                 255
Pro Ile Ala Val Pro Gln Thr Val Ser Leu Thr Leu Ser Asn Gly Ser
                260                 265                 270
Ser Ser Ala Thr Ile Ser Ala Gln Ile Thr Asp Ala Asn Asp Leu Ser
            275                 280                 285
Ala Ile Ala Arg Glu Val Asn Ala Ala Ser Gly Lys Thr Gly Ile Thr
            290                 295                 300
Ala Glu Val Ala Asn Asp Gly Ser Ile Thr Leu Ile Gln Glu Gln Gly
305                 310                 315                 320
Lys Asp Ile Thr Ile Glu Asp Phe Thr Ala Ala Gly Ser Gln Gln Leu
                325                 330                 335
Ala Val Gln Gly Ser Gly Asp Pro Ser Ala Ile Glu Leu Thr Asn Gly
            340                 345                 350
Gly Ala Asn Ala Thr Arg Ile Ala Gly Glu Leu Thr Leu Asp Ser Ser
            355                 360                 365
Val Ser Phe Ala Ala Thr Ser Asp Ala Thr Leu Ala Ala Gly Ser Val
            370                 375                 380
Leu Asn Ser Ala Gln Asn Thr Ala Ala Gly Ser Thr Pro Glu Glu Val
385                 390                 395                 400
Ala Gly Ile Asp Ile Ser Thr Val Asp Gly Ala Thr Ser Ala Leu Ala
                405                 410                 415
Val Val Asp Ala Ala Leu Glu Thr Ile Ser Gly Ile Arg Ala Asp Leu
                420                 425                 430
Gly Ala Ala Gln Asn Arg Leu Glu Ser Thr Ile Ala Asn Leu Ser Thr
            435                 440                 445
Thr Ser Glu Asn Leu Ser Ala Ala Arg Ser Arg Ile Arg Asp Ala Asp
            450                 455                 460
Phe Ala Ala Glu Ser Ala Glu Leu Ala Arg Thr Gln Val Leu Gln Gln
465                 470                 475                 480
Ala Gly Leu Ser Val Leu Ala Gln Ala Asn Ala Arg Pro Gln Gln Val
                485                 490                 495
Leu Gln Leu Leu Gln Gly Ala Cys His Pro Thr Glu Pro Tyr Thr Thr
            500                 505                 510
Val Thr Thr Gln Asn Thr Ala Ser Gln Thr Met Ser Ala Ile Glu Asn
            515                 520                 525
Leu Gly Thr His Pro Thr Glu Pro Tyr Thr Thr Val Thr Gln Asn
            530                 535                 540
```

```
Thr Ala Ser Gln Thr Met Ser Ala Ile Glu Asn Leu Ala Ser His Pro
545                 550                 555                 560

Thr Glu Pro Tyr Thr Thr Val Thr Thr Gln Asn Thr Ala Ser Gln Thr
            565                 570                 575

Met Ser Ala Ile Glu Asn Leu Leu Glu His Pro Thr Glu Pro Tyr Thr
        580                 585                 590

Thr Val Thr Thr Gln Asn Thr Ala Ser Gln Thr Met Ser Ala Ile Glu
    595                 600                 605

Asn Leu
    610

<210> SEQ ID NO 25
<211> LENGTH: 1827
<212> TYPE: DNA
<213> ORGANISM: Marinobacter algicola (DG893)
<220> FEATURE:
<221> NAME/KEY: Flagellin FR4DUD
<222> LOCATION: (1)..(1827)
<220> FEATURE:
<221> NAME/KEY: characteristic
<222> LOCATION: (1507)..(1581)
<223> OTHER INFORMATION: DUD epitope
<220> FEATURE:
<221> NAME/KEY: characteristic
<222> LOCATION: (1588)..(1662)
<223> OTHER INFORMATION: DUD epitope
<220> FEATURE:
<221> NAME/KEY: characteristic
<222> LOCATION: (1669)..(1743)
<223> OTHER INFORMATION: DUD epitope
<220> FEATURE:
<221> NAME/KEY: characteristic
<222> LOCATION: (1750)..(1824)
<223> OTHER INFORMATION: DUD epitope

<400> SEQUENCE: 25
atggctctcg gtattaacac taacgttgcg tcactgtcag ctcagaacca gctgaacaaa    60
tcccaggagc tttctaacca agctctggag cgtctgtctt ccggtctgcg catcaactcc   120
gccaaggacg atgctgctgg cctttgcaatt tcgacccgtt ttcagtccca gatctctggt   180
ctgaatgttg cccagcgtaa cgccaacgac ggtatttccc tggctcagac tgctgaaggt   240
gctctggaag aaaccaccaa catcctgcag cgcatccgtg agctgtctgt tcagtcggcc   300
aactctacca actcttcttc cgaccgctct gcacttcagg gcgaagtaaa ccagctgaag   360
caagagcttg atcgtattgc cggtaccacc cagtttaacg gcctcaacct tctggatggc   420
agcttcactg cccagtcatt ccaggttggt gccaacgcta accagaccat ctcggtctct   480
gtaactggcg ctcgtggtgc cgaccttggt aacaacaccg tatccggtga agtgatacc    540 actgtcagtc agggcacggg ttctgttgca gtcgcggccg ctgatgtggc aaccgttgcc   600
aacaatacga ttgctacaca gaacatcacc gtttctggaa ctgaaggctc tgaggtcatc   660
ggtattaccc agggcgatac tgcagaagcg attgcggctg ctgttaacgc tgaaaccggc   720
acgactggtg taacggctac ggcatccacc acggcaaccc tcgctggtct gtctgacgat   780
ggtacggttt cctttacgct tggcagtggt ggcgacacag cgaccatctc cgcagcggta   840
acgaccactg acctgggtgc gctggccaaa gcgatcaacg atacctcagg caccactggt   900
gttacggctg aagcaaacgg tggcgaaatc acactgaccc aggctgatgg caaagacatc   960
cgtctgcagg actttgccaa ctcaggtaac gcgaccggta ccgccacgct gcagggcagc  1020
ggtgacccat cagcggttac tttgaccgct ggcagcactg acagcacgat tgcttctggc  1080
```

```
tctgttgaat tcgcctcttc cggtgcattc tcagtaagct cctctgtcgc agagactgcc    1140
ggtagcattc tgaacgtcgc agccgacacc gtggttggtt ccaacctcca gtcagtgtct    1200
tctatcgaca tcggtactgt tgcgggcgct aacagcgcaa tcgagattgc agatgcggct    1260
ctggagcaga tcagtggtat ccgcgccgat ctgggtgctg cccagaaccg gttcgagtct    1320
acgatcgcca acctgagcac aactgccgaa aacctgtcgg ccgctaacag ccggattctg    1380
gatgcagact tcgcatctga aactgctaag ctgtccaagg cgcaggttct ccagcaagct    1440
ggtatctctg tactggcaca ggcgaatgcc cgtccacagc aggttctgtc cctcctgcag    1500
caattccatc cgactgagcc ttacacgaca gtcactactc agaacactgc ttcacaaaca    1560
atgtcggcta ttgaaaattt aggtacccat ccgactgagc cttacacgac agtcactact    1620
cagaacactg cttcacaaac aatgtcggct attgaaaatt tagctagcca tccgactgag    1680
ccttacacga cagtcactac tcagaacact gcttcacaaa caatgtcggc tattgaaaat    1740
ttactcgagc atccgactga gccttacacg acagtcacta ctcagaacac tgcttcacaa    1800
acaatgtcgg ctattgaaaa tttataa                                        1827
```

<210> SEQ ID NO 26
<211> LENGTH: 608
<212> TYPE: PRT
<213> ORGANISM: Marinobacter algicola (DG893)
<220> FEATURE:
<221> NAME/KEY: Flagellin FR4DUD
<222> LOCATION: (1)..(608)
<220> FEATURE:
<221> NAME/KEY: CHARACTERISTIC
<222> LOCATION: (503)..(527)
<223> OTHER INFORMATION: DUD epitope
<220> FEATURE:
<221> NAME/KEY: CHARACTERISTIC
<222> LOCATION: (530)..(554)
<223> OTHER INFORMATION: DUD epitope
<220> FEATURE:
<221> NAME/KEY: CHARACTERISTIC
<222> LOCATION: (557)..(581)
<223> OTHER INFORMATION: DUD epitope
<220> FEATURE:
<221> NAME/KEY: CHARACTERISTIC
<222> LOCATION: (584)..(608)
<223> OTHER INFORMATION: DUD epitope

<400> SEQUENCE: 26

Met Ala Leu Gly Ile Asn Thr Asn Val Ala Ser Leu Ser Ala Gln Asn
1               5                   10                  15

Gln Leu Asn Lys Ser Gln Glu Leu Ser Asn Gln Ala Leu Glu Arg Leu
            20                  25                  30

Ser Ser Gly Leu Arg Ile Asn Ser Ala Lys Asp Asp Ala Ala Gly Leu
        35                  40                  45

Ala Ile Ser Thr Arg Phe Gln Ser Gln Ile Ser Gly Leu Asn Val Ala
    50                  55                  60

Gln Arg Asn Ala Asn Asp Gly Ile Ser Leu Ala Gln Thr Ala Glu Gly
65                  70                  75                  80

Ala Leu Glu Glu Thr Thr Asn Ile Leu Gln Arg Ile Arg Glu Leu Ser
                85                  90                  95

Val Gln Ser Ala Asn Ser Thr Asn Ser Ser Ser Asp Arg Ser Ala Leu
            100                 105                 110

Gln Gly Glu Val Asn Gln Leu Lys Gln Glu Leu Asp Arg Ile Ala Gly
        115                 120                 125

Thr Thr Gln Phe Asn Gly Leu Asn Leu Leu Asp Gly Ser Phe Thr Ala
    130                 135                 140

```
Gln Ser Phe Gln Val Gly Ala Asn Ala Asn Gln Thr Ile Ser Val Ser
145                 150                 155                 160

Val Thr Gly Ala Arg Gly Ala Asp Leu Gly Asn Asn Thr Val Ser Gly
            165                 170                 175

Glu Ser Asp Thr Thr Val Ser Gln Gly Thr Gly Ser Val Ala Val Ala
                180                 185                 190

Ala Ala Asp Val Ala Thr Val Ala Asn Asn Thr Ile Ala Thr Gln Asn
        195                 200                 205

Ile Thr Val Ser Gly Thr Glu Gly Ser Glu Val Ile Gly Ile Thr Gln
210                 215                 220

Gly Asp Thr Ala Glu Ala Ile Ala Ala Val Asn Ala Glu Thr Gly
225                 230                 235                 240

Thr Thr Gly Val Thr Ala Thr Ala Ser Thr Ala Thr Leu Ala Gly
                245                 250                 255

Leu Ser Asp Asp Gly Thr Val Ser Phe Thr Leu Gly Ser Gly Gly Asp
                260                 265                 270

Thr Ala Thr Ile Ser Ala Ala Val Thr Thr Asp Leu Gly Ala Leu
        275                 280                 285

Ala Lys Ala Ile Asn Asp Thr Ser Gly Thr Thr Gly Val Thr Ala Glu
290                 295                 300

Ala Asn Gly Gly Glu Ile Thr Leu Thr Gln Ala Asp Gly Lys Asp Ile
305                 310                 315                 320

Arg Leu Gln Asp Phe Ala Asn Ser Gly Asn Ala Thr Gly Thr Ala Thr
                325                 330                 335

Leu Gln Gly Ser Gly Asp Pro Ser Ala Val Thr Leu Thr Ala Gly Ser
                340                 345                 350

Thr Asp Ser Thr Ile Ala Ser Gly Ser Val Glu Phe Ala Ser Ser Gly
            355                 360                 365

Ala Phe Ser Val Ser Ser Val Ala Glu Thr Ala Gly Ser Ile Leu
        370                 375                 380

Asn Val Ala Ala Asp Thr Val Val Gly Ser Asn Leu Gln Ser Val Ser
385                 390                 395                 400

Ser Ile Asp Ile Gly Thr Val Ala Gly Ala Asn Ser Ala Ile Glu Ile
                405                 410                 415

Ala Asp Ala Ala Leu Glu Gln Ile Ser Gly Ile Arg Ala Asp Leu Gly
                420                 425                 430

Ala Ala Gln Asn Arg Phe Glu Ser Thr Ile Ala Asn Leu Ser Thr Thr
        435                 440                 445

Ala Glu Asn Leu Ser Ala Ala Asn Ser Arg Ile Leu Asp Ala Asp Phe
450                 455                 460

Ala Ser Glu Thr Ala Lys Leu Ser Lys Ala Gln Val Leu Gln Gln Ala
465                 470                 475                 480

Gly Ile Ser Val Leu Ala Gln Ala Asn Ala Arg Pro Gln Gln Val Leu
                485                 490                 495

Ser Leu Leu Gln Gln Phe His Pro Thr Glu Pro Tyr Thr Thr Val Thr
                500                 505                 510

Thr Gln Asn Thr Ala Ser Gln Thr Met Ser Ala Ile Glu Asn Leu Gly
            515                 520                 525

Thr His Pro Thr Glu Pro Tyr Thr Thr Val Thr Thr Gln Asn Thr Ala
            530                 535                 540

Ser Gln Thr Met Ser Ala Ile Glu Asn Leu Ala Ser His Pro Thr Glu
545                 550                 555                 560
```

```
Pro Tyr Thr Thr Val Thr Thr Gln Asn Thr Ala Ser Gln Thr Met Ser
                565                 570                 575

Ala Ile Glu Asn Leu Leu Glu His Pro Thr Glu Pro Tyr Thr Thr Val
            580                 585                 590

Thr Thr Gln Asn Thr Ala Ser Gln Thr Met Ser Ala Ile Glu Asn Leu
        595                 600                 605

<210> SEQ ID NO 27
<211> LENGTH: 24
<212> TYPE: PRT
<213> ORGANISM: Influenza A virus
<220> FEATURE:
<221> NAME/KEY: CHARACTERISTIC
<222> LOCATION: (1)..(24)
<223> OTHER INFORMATION: M2-2009 peptide

<400> SEQUENCE: 27

Met Ser Leu Leu Thr Glu Val Glu Thr Pro Thr Arg Ser Glu Trp Glu
1               5                   10                  15

Cys Arg Cys Ser Asp Ser Ser Asp
            20

<210> SEQ ID NO 28
<211> LENGTH: 1854
<212> TYPE: DNA
<213> ORGANISM: Marinobacter algicola (DG893)
<220> FEATURE:
<221> NAME/KEY: Flagellin FR4M2-2009
<222> LOCATION: (1)..(1854)
<220> FEATURE:
<221> NAME/KEY: characteristic
<222> LOCATION: (1538)..(1584)
<223> OTHER INFORMATION: M2-2009 epitope
<220> FEATURE:
<221> NAME/KEY: characteristic
<222> LOCATION: (1585)..(1655)
<223> OTHER INFORMATION: M2-2009 epitope
<220> FEATURE:
<221> NAME/KEY: characteristic
<222> LOCATION: (1656)..(1728)
<223> OTHER INFORMATION: M2-2009 epitope
<220> FEATURE:
<221> NAME/KEY: characteristic
<222> LOCATION: (1729)..(1800)
<223> OTHER INFORMATION: M2-2009 epitope
<220> FEATURE:
<221> NAME/KEY: characteristic
<222> LOCATION: (1807)..(1825)
<223> OTHER INFORMATION: Sequence that encodes a histidine tail
<220> FEATURE:
<221> NAME/KEY: characteristic
<222> LOCATION: (1835)..(1846)
<223> OTHER INFORMATION: Sequence that encodes the KDEP sequence

<400> SEQUENCE: 28
ggatccatgg ctctcggtat taacactaac gttgcgtcac tgtcagctca gaaccagctg      60
aacaaatccc aggagctttc taaccaagct ctggagcgtc tgtcttccgg tctgcgcatc     120
aactccgcca aggacgatgc tgctggcctt gcaatttcga cccgttttca gtcccagatc     180
tctggtctga atgttgccca gcgtaacgcc aacgacggta tttccctggc tcagactgct     240
gaaggtgctc tggaagaaac caccaacatc ctgcagcgca tccgtgagct gtctgttcag     300
tcggccaact ctaccaactc ttcttccgac cgctctgcac ttcagggcga agtaaaccag     360
ctgaagcaag agcttgatcg tattgccggt accacccagt taacggcct caaccttctg     420 gatggcagct tcactgccca gtcattccag gttggtgcca cgctaaccca gaccatctcg     480
gtctctgtaa ctggcgctcg tggtgccgac cttggtaaca acaccgtatc cggtgaaagt     540
```

-continued

```
gataccactg tcagtcaggg cacgggttct gttgcagtcg cggccgctga tgtggcaacc    600
gttgccaaca atacgattgc tacacagaac atcaccgttt ctggaactga aggctctgag    660
gtcatcggta ttacccaggg cgatactgca gaagcgattg cggctgctgt taacgctgaa    720
accggcacga ctggtgtaac ggctacggca tccaccacgg caaccctcgc tggtctgtct    780
gacgatggta cggtttcctt tacgcttggc agtggtggcg acacagcgac catctccgca    840
gcggtaacga ccactgacct gggtgcgctg gccaaagcga tcaacgatac ctcaggcacc    900
actggtgtta cggctgaagc aaacggtggc gaaatcacac tgacccaggc tgatggcaaa    960
gacatccgtc tgcaggactt tgccaactca ggtaacgcga ccgtaccgc acgctgcag    1020 ggcagcggtg acccatcagc ggttactttg accgctggca gcactgacag cacgattgct    1080
tctggctctg ttgaattcgc tcttccggt gcattctcag taagctcctc tgtcgcagag    1140
actgccggta gcattctgaa cgtcgcagcc gacaccgtgg ttggttccaa cctccagtca    1200
gtgtcttcta tcgacatcgg tactgttgcg ggcgctaaca gcgcaatcga gattgcagat    1260
gcggctctgg agcagatcag tggtatccgc gccgatctgg gtgctgccca gaaccggttc    1320
gagtctacga tcgccaacct gagcacaact gccgaaaacc tgtcggccgc taacagccgg    1380
attctggatg cagacttcgc atctgaaact gctaagctgt ccaaggcgca ggttctccag    1440
caagctggta tctctgtact ggcacaggcg aatgcccgtc cacagcaggt tctgtccctc    1500
ctgcagcaat tcatgagtct tctaaccgag gtcgaaacgc taccagaag cgaatgggag    1560 tgcagatgca gcgattcaag tgatatgagt cttctaaccg aggtcgaaac gcctaccaga    1620
agcgaatggg agtgcagatg cagcgattca agtgatatga gtcttctaac cgaggtcgaa    1680
acgcctacca gaagcgaatg ggagtgcaga tgcagcgatt caagtgatat gagtcttcta    1740
accgaggtcg aaacgcctac cagaagcgaa tgggagtgca gatgcagcga ttcaagtgat    1800
tctagacatc accaccacca tcaccatgct agaaaagatg aactgtaaaa gctt          1854
```

<210> SEQ ID NO 29
<211> LENGTH: 617
<212> TYPE: PRT
<213> ORGANISM: Marinobacter algicola (DG893)
<220> FEATURE:
<221> NAME/KEY: Flagellin FR4M2-2009
<222> LOCATION: (1)..(617)
<220> FEATURE:
<221> NAME/KEY: CHARACTERISTIC
<222> LOCATION: (505)..(528)
<223> OTHER INFORMATION: M2-2009 epitope
<220> FEATURE:
<221> NAME/KEY: CHARACTERISTIC
<222> LOCATION: (529)..(552)
<223> OTHER INFORMATION: M2-2009 epitope
<220> FEATURE:
<221> NAME/KEY: CHARACTERISTIC
<222> LOCATION: (553)..(576)
<223> OTHER INFORMATION: M2-2009 epitope
<220> FEATURE:
<221> NAME/KEY: CHARACTERISTIC
<222> LOCATION: (577)..(600)
<223> OTHER INFORMATION: M2-2009 epitope
<220> FEATURE:
<221> NAME/KEY: CHARACTERISTIC
<222> LOCATION: (612)..(615)
<223> OTHER INFORMATION: KDEL sequence

<400> SEQUENCE: 29

Gly Ser Met Ala Leu Gly Ile Asn Thr Asn Val Ala Ser Leu Ser Ala
1               5                   10                  15

-continued

```
Gln Asn Gln Leu Asn Lys Ser Gln Glu Leu Ser Asn Gln Ala Leu Glu
             20                  25                  30

Arg Leu Ser Ser Gly Leu Arg Ile Asn Ser Ala Lys Asp Asp Ala Ala
         35                  40                  45

Gly Leu Ala Ile Ser Thr Arg Phe Gln Ser Gln Ile Ser Gly Leu Asn
     50                  55                  60

Val Ala Gln Arg Asn Ala Asn Asp Gly Ile Ser Leu Ala Gln Thr Ala
 65                  70                  75                  80

Glu Gly Ala Leu Glu Gly Thr Thr Asn Ile Leu Gln Arg Ile Arg Glu
                 85                  90                  95

Leu Ser Val Gln Ser Ala Asn Ser Thr Asn Ser Ser Ser Asp Arg Ser
            100                 105                 110

Ala Leu Gln Gly Glu Val Asn Gln Leu Lys Gln Glu Leu Asp Arg Ile
        115                 120                 125

Ala Gly Thr Thr Gln Phe Asn Gly Leu Asn Leu Leu Asp Gly Ser Phe
    130                 135                 140

Thr Ala Gln Ser Phe Gln Val Gly Ala Asn Ala Asn Gln Thr Ile Ser
145                 150                 155                 160

Val Ser Val Thr Gly Ala Arg Gly Ala Asp Leu Gly Asn Asn Thr Val
                165                 170                 175

Ser Gly Glu Ser Asp Thr Thr Val Ser Gln Gly Thr Gly Ser Val Ala
            180                 185                 190

Val Ala Ala Ala Asp Val Ala Thr Val Ala Asn Asn Thr Ile Ala Thr
        195                 200                 205

Gln Asn Ile Thr Val Ser Gly Thr Glu Gly Ser Glu Val Ile Gly Ile
    210                 215                 220

Thr Gln Gly Asp Thr Ala Glu Ala Ile Ala Ala Val Asn Ala Glu
225                 230                 235                 240

Thr Gly Thr Thr Gly Val Thr Ala Thr Ala Ser Thr Thr Ala Thr Leu
                245                 250                 255

Ala Gly Leu Ser Asp Asp Gly Thr Val Ser Phe Thr Leu Gly Ser Gly
            260                 265                 270

Gly Asp Thr Ala Thr Ile Ser Ala Ala Val Thr Thr Thr Asp Leu Gly
        275                 280                 285

Ala Leu Ala Lys Ala Ile Asn Asp Thr Ser Gly Thr Thr Gly Val Thr
    290                 295                 300

Ala Glu Ala Asn Gly Gly Glu Ile Thr Leu Thr Gln Ala Asp Gly Lys
305                 310                 315                 320

Asp Ile Arg Leu Gln Asp Phe Ala Asn Ser Gly Asn Ala Thr Gly Thr
                325                 330                 335

Ala Thr Leu Gln Gly Ser Gly Asp Pro Ser Ala Val Thr Leu Thr Ala
            340                 345                 350

Gly Ser Thr Asp Ser Thr Ile Ala Ser Gly Ser Val Glu Phe Ala Ser
        355                 360                 365

Ser Gly Ala Phe Ser Val Ser Ser Val Ala Glu Thr Ala Gly Ser
    370                 375                 380

Ile Leu Asn Val Ala Ala Asp Thr Val Val Gly Ser Asn Leu Gln Ser
385                 390                 395                 400

Val Ser Ser Ile Asp Ile Gly Thr Val Ala Gly Ala Asn Ser Ala Ile
                405                 410                 415

Glu Ile Ala Asp Ala Ala Leu Glu Gln Ile Ser Gly Ile Arg Ala Asp
            420                 425                 430

Leu Gly Ala Ala Gln Asn Arg Phe Glu Ser Thr Ile Ala Asn Leu Ser
```

```
                    435                 440                 445
Thr Thr Ala Glu Asn Leu Ser Ala Ala Asn Ser Arg Ile Leu Asp Ala
    450                 455                 460

Asp Phe Ala Ser Glu Thr Ala Lys Leu Ser Lys Ala Gln Val Leu Gln
465                 470                 475                 480

Gln Ala Gly Ile Ser Val Leu Ala Gln Ala Asn Ala Arg Pro Gln Gln
                485                 490                 495

Val Leu Ser Leu Leu Gln Gln Phe Met Ser Leu Leu Thr Glu Val Glu
            500                 505                 510

Thr Pro Thr Arg Ser Glu Trp Glu Cys Arg Cys Ser Asp Ser Ser Asp
        515                 520                 525

Met Ser Leu Leu Thr Glu Val Glu Thr Pro Thr Arg Ser Glu Trp Glu
    530                 535                 540

Cys Arg Cys Ser Asp Ser Ser Asp Met Ser Leu Leu Thr Glu Val Glu
545                 550                 555                 560

Thr Pro Thr Arg Ser Glu Trp Glu Cys Arg Cys Ser Asp Ser Ser Asp
                565                 570                 575

Met Ser Leu Leu Thr Glu Val Glu Thr Pro Thr Arg Ser Glu Trp Glu
            580                 585                 590

Cys Arg Cys Ser Asp Ser Ser Asp Ser Arg His His His His His
        595                 600                 605

His Ala Arg Lys Asp Glu Leu Lys Leu
    610                 615

<210> SEQ ID NO 30
<211> LENGTH: 1815
<212> TYPE: DNA
<213> ORGANISM: Marinobacter algicola (DG893)
<220> FEATURE:
<221> NAME/KEY: Flagellin FR4M2-2009
<222> LOCATION: (1)..(1815)
<220> FEATURE:
<221> NAME/KEY: characteristic
<222> LOCATION: (1538)..(1584)
<223> OTHER INFORMATION: M2-2009 epitope
<220> FEATURE:
<221> NAME/KEY: characteristic
<222> LOCATION: (1585)..(1655)
<223> OTHER INFORMATION: M2-2009 epitope
<220> FEATURE:
<221> NAME/KEY: characteristic
<222> LOCATION: (1656)..(1728)
<223> OTHER INFORMATION: M2-2009 epitope
<220> FEATURE:
<221> NAME/KEY: characteristic
<222> LOCATION: (1729)..(1800)
<223> OTHER INFORMATION: M2-2009 epitope

<400> SEQUENCE: 30
ggatccatgg ctctcggtat taacactaac gttgcgtcac tgtcagctca gaaccagctg      60
aacaaatccc aggagctttc taaccaagct ctggagcgtc tgtcttccgg tctgcgcatc     120
aactccgcca aggacgatgc tgctggcctt gcaatttcga cccgttttca gtcccagatc     180
tctggtctga atgttgccca gcgtaacgcc aacgacggta tttcccctgg tcagactgct     240
gaaggtgctc tggaagaaac caccaacatc ctgcagcgca tccgtgagct gtctgttcag     300
tcggccaact ctaccaactc ttcttccgac cgctctgcac ttcagggcga agtaaaccag     360
ctgaagcaag agcttgatcg tattgccggt accaccccagt ttaacggcct caaccttctg     420
gatggcagct tcactgccca gtcattccag gttggtgcca acgctaacca gaccatctcg     480
gtctctgtaa ctggcgctcg tggtgccgac cttggtaaca acaccgtatc cggtgaaagt     540
```

```
gataccactg tcagtcaggg cacgggttct gttgcagtcg cggccgctga tgtggcaacc    600
gttgccaaca atacgattgc tacacagaac atcaccgttt ctggaactga aggctctgag    660
gtcatcggta ttacccaggg cgatactgca gaagcgattg cggctgctgt taacgctgaa    720
accggcacga ctggtgtaac ggctacggca tccaccacgg caaccctcgc tggtctgtct    780
gacgatggta cggtttcctt tacgcttggc agtggtggcg acacagcgac catctccgca    840
gcggtaacga ccactgacct gggtgcgctg gccaaagcga tcaacgatac ctcaggcacc    900
actggtgtta cggctgaagc aaacggtggc gaaatcacac tgacccaggc tgatggcaaa    960
gacatccgtc tgcaggactt tgccaactca ggtaacgcga ccgtaccgc acgctgcag    1020 ggcagcggtg acccatcagc ggttactttg accgctggca gcactgacag cacgattgct    1080
tctggctctg ttgaattcgc ctcttccggt gcattctcag taagctcctc tgtcgcagag    1140
actgccggta gcattctgaa cgtcgcagcc gacaccgtgg ttggttccaa cctccagtca    1200
gtgtcttcta tcgacatcgg tactgttgcg ggcgctaaca cgcaatcga gattgcagat    1260 gcggctctgg agcagatcag tggtatccgc gccgatctgg gtgctgccca gaaccggttc    1320
gagtctacga tcgccaaccct gagcacaact gccgaaaaacc tgtcggccgc taacagccgg    1380
attctggatg cagacttcgc atctgaaact gctaagctgt ccaaggcgca ggttctccag    1440
caagctggta tctctgtact ggcacaggcg aatgcccgtc cacagcaggt tctgtccctc    1500
ctgcagcaat tcatgagtct tctaaccgag gtcgaaacgc ctaccagaag cgaatgggag    1560
tgcagatgca gcgattcaag tgatatgagt cttctaaccg aggtcgaaac gcctaccaga    1620
agcgaatggg agtgcagatg cagcgattca agtgatatga gtcttctaac cgaggtcgaa    1680
acgcctacca gaagcgaatg ggagtgcaga tgcagcgatt caagtgatat gagtcttcta    1740
accgaggtcg aaacgcctac cagaagcgaa tgggagtgca gatgcagcga ttcaagtgat    1800
tctagataaa agctt                                                    1815
```

<210> SEQ ID NO 31
<211> LENGTH: 604
<212> TYPE: PRT
<213> ORGANISM: Marinobacter algicola (DG893)
<220> FEATURE:
<221> NAME/KEY: Flagellin FR4M2-2009
<222> LOCATION: (1)..(604)
<220> FEATURE:
<221> NAME/KEY: CHARACTERISTIC
<222> LOCATION: (505)..(528)
<223> OTHER INFORMATION: M2-2009 epitope
<220> FEATURE:
<221> NAME/KEY: CHARACTERISTIC
<222> LOCATION: (529)..(552)
<223> OTHER INFORMATION: M2-2009 epitope
<220> FEATURE:
<221> NAME/KEY: CHARACTERISTIC
<222> LOCATION: (553)..(576)
<223> OTHER INFORMATION: M2-2009 epitope
<220> FEATURE:
<221> NAME/KEY: CHARACTERISTIC
<222> LOCATION: (577)..(600)
<223> OTHER INFORMATION: M2-2009 epitope

<400> SEQUENCE: 31

```
Gly Ser Met Ala Leu Gly Ile Asn Thr Asn Val Ala Ser Leu Ser Ala
1               5                   10                  15

Gln Asn Gln Leu Asn Lys Ser Gln Glu Leu Ser Asn Gln Ala Leu Glu
            20                  25                  30

Arg Leu Ser Ser Gly Leu Arg Ile Asn Ser Ala Lys Asp Asp Ala Ala
```

```
                35                  40                  45
Gly Leu Ala Ile Ser Thr Arg Phe Gln Ser Gln Ile Ser Gly Leu Asn
         50                  55                  60
Val Ala Gln Arg Asn Ala Asn Asp Gly Ile Ser Leu Ala Gln Thr Ala
 65                  70                  75                  80
Glu Gly Ala Leu Glu Glu Thr Thr Asn Ile Leu Gln Arg Ile Arg Glu
                 85                  90                  95
Leu Ser Val Gln Ser Ala Asn Ser Thr Asn Ser Ser Ser Asp Arg Ser
                100                 105                 110
Ala Leu Gln Gly Glu Val Asn Gln Leu Lys Gln Glu Leu Asp Arg Ile
                115                 120                 125
Ala Gly Thr Thr Gln Phe Asn Gly Leu Asn Leu Leu Asp Gly Ser Phe
            130                 135                 140
Thr Ala Gln Ser Phe Gln Val Gly Ala Asn Ala Asn Gln Thr Ile Ser
145                 150                 155                 160
Val Ser Val Thr Gly Ala Arg Gly Ala Asp Leu Gly Asn Asn Thr Val
                165                 170                 175
Ser Gly Glu Ser Asp Thr Thr Val Ser Gln Gly Thr Gly Ser Val Ala
                180                 185                 190
Val Ala Ala Ala Asp Val Ala Thr Val Ala Asn Asn Thr Ile Ala Thr
            195                 200                 205
Gln Asn Ile Thr Val Ser Gly Thr Glu Gly Ser Glu Val Ile Gly Ile
        210                 215                 220
Thr Gln Gly Asp Thr Ala Glu Ala Ile Ala Ala Val Asn Ala Glu
225                 230                 235                 240
Thr Gly Thr Thr Gly Val Thr Ala Thr Ala Ser Thr Thr Ala Thr Leu
                245                 250                 255
Ala Gly Leu Ser Asp Asp Gly Thr Val Ser Phe Thr Leu Gly Ser Gly
                260                 265                 270
Gly Asp Thr Ala Thr Ile Ser Ala Ala Val Thr Thr Thr Asp Leu Gly
            275                 280                 285
Ala Leu Ala Lys Ala Ile Asn Asp Thr Ser Gly Thr Thr Gly Val Thr
        290                 295                 300
Ala Glu Ala Asn Gly Gly Glu Ile Thr Leu Thr Gln Ala Asp Gly Lys
305                 310                 315                 320
Asp Ile Arg Leu Gln Asp Phe Ala Asn Ser Gly Asn Ala Thr Gly Thr
                325                 330                 335
Ala Thr Leu Gln Gly Ser Gly Asp Pro Ser Ala Val Thr Leu Thr Ala
                340                 345                 350
Gly Ser Thr Asp Ser Thr Ile Ala Ser Gly Ser Val Glu Phe Ala Ser
            355                 360                 365
Ser Gly Ala Phe Ser Val Ser Ser Val Ala Glu Thr Ala Gly Ser
        370                 375                 380
Ile Leu Asn Val Ala Ala Asp Thr Val Val Gly Ser Asn Leu Gln Ser
385                 390                 395                 400
Val Ser Ser Ile Asp Ile Gly Thr Val Ala Gly Ala Asn Ser Ala Ile
                405                 410                 415
Glu Ile Ala Asp Ala Ala Leu Glu Gln Ile Ser Gly Ile Arg Ala Asp
                420                 425                 430
Leu Gly Ala Ala Gln Asn Arg Phe Glu Ser Thr Ile Ala Asn Leu Ser
            435                 440                 445
Thr Thr Ala Glu Asn Leu Ser Ala Ala Asn Ser Arg Ile Leu Asp Ala
        450                 455                 460
```

```
Asp Phe Ala Ser Glu Thr Ala Lys Leu Ser Lys Ala Gln Val Leu Gln
465                 470                 475                 480

Gln Ala Gly Ile Ser Val Leu Ala Gln Ala Asn Ala Arg Pro Gln Gln
                485                 490                 495

Val Leu Ser Leu Leu Gln Gln Phe Met Ser Leu Leu Thr Glu Val Glu
            500                 505                 510

Thr Pro Thr Arg Ser Glu Trp Glu Cys Arg Cys Ser Asp Ser Ser Asp
            515                 520                 525

Met Ser Leu Leu Thr Glu Val Glu Thr Pro Thr Arg Ser Glu Trp Glu
            530                 535                 540

Cys Arg Cys Ser Asp Ser Ser Asp Met Ser Leu Leu Thr Glu Val Glu
545                 550                 555                 560

Thr Pro Thr Arg Ser Glu Trp Glu Cys Arg Cys Ser Asp Ser Ser Asp
                565                 570                 575

Met Ser Leu Leu Thr Glu Val Glu Thr Pro Thr Arg Ser Glu Trp Glu
            580                 585                 590

Cys Arg Cys Ser Asp Ser Ser Asp Ser Arg Lys Leu
            595                 600

<210> SEQ ID NO 32
<211> LENGTH: 1956
<212> TYPE: DNA
<213> ORGANISM: Marinobacter algicola (DG893)
<220> FEATURE:
<221> NAME/KEY: pRSETA-FR4M2-2009 plasmid
<222> LOCATION: (1)..(1956)
<220> FEATURE:
<221> NAME/KEY: characteristic
<222> LOCATION: (110)..(1607)
<223> OTHER INFORMATION: Sequence of Flagellin FR
<220> FEATURE:
<221> NAME/KEY: characteristic
<222> LOCATION: (1613)..(1684)
<223> OTHER INFORMATION: M2-2009 epitope
<220> FEATURE:
<221> NAME/KEY: characteristic
<222> LOCATION: (1685)..(1756)
<223> OTHER INFORMATION: M2-2009 epitope
<220> FEATURE:
<221> NAME/KEY: characteristic
<222> LOCATION: (1757)..(1828)
<223> OTHER INFORMATION: M2-2009 epitope
<220> FEATURE:
<221> NAME/KEY: characteristic
<222> LOCATION: (1829)..(1901)
<223> OTHER INFORMATION: M2-2009 epitope
<220> FEATURE:
<221> NAME/KEY: characteristic
<222> LOCATION: (1908)..(1928)
<223> OTHER INFORMATION: Sequence that encodes a histidine tail
<220> FEATURE:
<221> NAME/KEY: characteristic
<222> LOCATION: (1935)..(1946)
<223> OTHER INFORMATION: Sequence that encodes the KDEL sequence

<400> SEQUENCE: 32
atgcggggtt ctcatcatca tcatcatcat ggtatggcta gcatgactgg tggacagcaa      60
atgggtcggg atctgtacga cgatgacgat aaggatcgat ggggatccat ggctctcggt     120
attaacacta acgttgcgtc actgtcagct cagaaccagc tgaacaaatc ccaggagctt     180
tctaaccaag ctctggagcg tctgtcttcc ggtctgcgca tcaactccgc caaggacgat     240
gctgctggcc ttgcaatttc gacccgtttt cagtcccaga tctctggtct gaatgttgcc     300
cagcgtaacg ccaacgacgg tatttccctg gctcagactc tgaaggtgc tctggaagaa     360
```

-continued

| | |
|---|---|
| accaccaaca tcctgcagcg catccgtgag ctgtctgttc agtcggccaa ctctaccaac | 420 |
| tcttcttccg accgctctgc acttcagggc gaagtaaacc agctgaagca agagcttgat | 480 |
| cgtattgccg gtaccaccca gtttaacggc ctcaaccttc tggatggcag cttcactgcc | 540 |
| cagtcattcc aggttggtgc caacgctaac cagaccatct cggtctctgt aactggcgct | 600 |
| cgtggtgccg accttggtaa caacaccgta tccggtgaaa gtgataccac tgtcagtcag | 660 |
| ggcacgggtt ctgttgcagt cgcggccgct gatgtggcaa ccgttgccaa caatacgatt | 720 |
| gctacacaga acatcaccgt ttctggaact gaaggctctg aggtcatcgg tattacccag | 780 |
| ggcgatactg cagaagcgat tgcggctgct gttaacgctg aaaccggcac gactggtgta | 840 |
| acggctacgg catccaccac ggcaaccctc gctggtctgt ctgacgatgg tacggtttcc | 900 |
| tttacgcttg gcagtggtgg cgacacagcg accatctccg cagcggtaac gaccactgac | 960 |
| ctgggtgcgc tggccaaagc gatcaacgat acctcaggca ccactggtgt tacggctgaa | 1020 |
| gcaaacggtg gcgaaatcac actgaccag gctgatggca agacatccg tctgcaggac | 1080 |
| tttgccaact caggtaacgc gaccggtacc gccacgctgc agggcagcgg tgacccatca | 1140 |
| gcggttactt tgaccgctgg cagcactgac agcacgattg cttctggctc tgttgaattc | 1200 |
| gcctcttccg gtgcattctc agtaagctcc tctgtcgcag agactgccgg tagcattctg | 1260 |
| aacgtcgcag ccgacaccgt ggttggttcc aacctccagt cagtgtcttc tatcgacatc | 1320 |
| ggtactgttg cgggcgctaa cagcgcaatc gagattgcag atgcggctct ggagcagatc | 1380 |
| agtggtatcc gcgccgatct gggtgctgcc cagaaccggt tcgagtctac gatcgccaac | 1440 |
| ctgagcacaa ctgccgaaaa cctgtcggcc gctaacagcc ggattctgga tgcagacttc | 1500 |
| gcatctgaaa ctgctaagct gtccaaggcg caggttctcc agcaagctgg tatctctgta | 1560 |
| ctggcacagg cgaatgcccg tccacagcag gttctgtccc tcctgcagca attcatgagt | 1620 |
| cttctaaccg aggtcgaaac gcctaccaga agcgaatggg agtgcagatg cagcgattca | 1680 |
| agtgatatga gtcttctaac cgaggtcgaa acgcctacca gaagcgaatg ggagtgcaga | 1740 |
| tgcagcgatt caagtgatat gagtcttcta accgaggtcg aaacgcctac cagaagcgaa | 1800 |
| tgggagtgca gatgcagcga ttcaagtgat atgagtcttc taaccgaggt cgaaacgcct | 1860 |
| accagaagcg aatgggagtg cagatgcagc gattcaagtg attctagaca tcaccaccac | 1920 |
| catcaccatg ctagaaaaga tgaactgtaa aagctt | 1956 |

```
<210> SEQ ID NO 33
<211> LENGTH: 650
<212> TYPE: PRT
<213> ORGANISM: Marinobacter algicola (DG893)
<220> FEATURE:
<221> NAME/KEY: pRSETA-FR4M2-2009 plasmid
<222> LOCATION: (1)..(650)
<220> FEATURE:
<221> NAME/KEY: CHARACTERISTIC
<222> LOCATION: (37)..(536)
<223> OTHER INFORMATION: Flagellin FR
<220> FEATURE:
<221> NAME/KEY: CHARACTERISTIC
<222> LOCATION: (539)..(562)
<223> OTHER INFORMATION: M2-2009 epitope
<220> FEATURE:
<221> NAME/KEY: CHARACTERISTIC
<222> LOCATION: (563)..(586)
<223> OTHER INFORMATION: M2-2009 epitope
<220> FEATURE:
<221> NAME/KEY: CHARACTERISTIC
<222> LOCATION: (587)..(610)
<223> OTHER INFORMATION: M2-2009 epitope
<220> FEATURE:
```

```
<221> NAME/KEY: CHARACTERISTIC
<222> LOCATION: (611)..(634)
<223> OTHER INFORMATION: M2-2009 epitope
<220> FEATURE:
<221> NAME/KEY: CHARACTERISTIC
<222> LOCATION: (637)..(643)
<223> OTHER INFORMATION: Histidine tail
<220> FEATURE:
<221> NAME/KEY: CHARACTERISTIC
<222> LOCATION: (645)..(648)
<223> OTHER INFORMATION: KDEL sequence

<400> SEQUENCE: 33
```

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Met Ala Leu Gly Ile Asn Thr Asn Val Ala Ser Leu
            35                  40                  45

Ser Ala Gln Asn Gln Leu Asn Lys Ser Gln Glu Leu Ser Asn Gln Ala
50                  55                  60

Leu Glu Arg Leu Ser Ser Gly Leu Arg Ile Asn Ser Ala Lys Asp Asp
65                  70                  75                  80

Ala Ala Gly Leu Ala Ile Ser Thr Arg Phe Gln Ser Gln Ile Ser Gly
                85                  90                  95

Leu Asn Val Ala Gln Arg Asn Ala Asn Asp Gly Ile Ser Leu Ala Gln
            100                 105                 110

Thr Ala Glu Gly Ala Leu Glu Glu Thr Thr Asn Ile Leu Gln Arg Ile
            115                 120                 125

Arg Glu Leu Ser Val Gln Ser Ala Asn Ser Thr Asn Ser Ser Ser Asp
130                 135                 140

Arg Ser Ala Leu Gln Gly Glu Val Asn Gln Leu Lys Gln Glu Leu Asp
145                 150                 155                 160

Arg Ile Ala Gly Thr Thr Gln Phe Asn Gly Leu Asn Leu Leu Asp Gly
                165                 170                 175

Ser Phe Thr Ala Gln Ser Phe Gln Val Gly Ala Asn Ala Asn Gln Thr
            180                 185                 190

Ile Ser Val Ser Val Thr Gly Ala Arg Gly Ala Asp Leu Gly Asn Asn
            195                 200                 205

Thr Val Ser Gly Glu Ser Asp Thr Thr Val Ser Gln Gly Thr Gly Ser
210                 215                 220

Val Ala Val Ala Ala Asp Val Ala Thr Val Ala Asn Asn Thr Ile
225                 230                 235                 240

Ala Thr Gln Asn Ile Thr Val Ser Gly Thr Glu Gly Ser Glu Val Ile
                245                 250                 255

Gly Ile Thr Gln Gly Asp Thr Ala Glu Ala Ile Ala Ala Val Asn
            260                 265                 270

Ala Glu Thr Gly Thr Thr Gly Val Thr Ala Thr Ala Ser Thr Thr Ala
            275                 280                 285

Thr Leu Ala Gly Leu Ser Asp Asp Gly Thr Val Ser Phe Thr Leu Gly
290                 295                 300

Ser Gly Gly Asp Thr Ala Thr Ile Ser Ala Ala Val Thr Thr Asp
305                 310                 315                 320

Leu Gly Ala Leu Ala Lys Ala Ile Asn Asp Thr Ser Gly Thr Gly
                325                 330                 335

Val Thr Ala Glu Ala Asn Gly Gly Glu Ile Thr Leu Thr Gln Ala Asp
            340                 345                 350

-continued

```
Gly Lys Asp Ile Arg Leu Gln Asp Phe Ala Asn Ser Gly Asn Ala Thr
    355                 360                 365

Gly Thr Ala Thr Leu Gln Gly Ser Gly Asp Pro Ser Ala Val Thr Leu
    370                 375                 380

Thr Ala Gly Ser Thr Asp Ser Thr Ile Ala Ser Gly Ser Val Glu Phe
385                 390                 395                 400

Ala Ser Ser Gly Ala Phe Ser Val Ser Ser Val Ala Glu Thr Ala
                405                 410                 415

Gly Ser Ile Leu Asn Val Ala Ala Asp Thr Val Val Gly Ser Asn Leu
                420                 425                 430

Gln Ser Val Ser Ser Ile Asp Ile Gly Thr Val Ala Gly Ala Asn Ser
        435                 440                 445

Ala Ile Glu Ile Ala Asp Ala Ala Leu Glu Gln Ile Ser Gly Ile Arg
    450                 455                 460

Ala Asp Leu Gly Ala Ala Gln Asn Arg Phe Glu Ser Thr Ile Ala Asn
465                 470                 475                 480

Leu Ser Thr Thr Ala Glu Asn Leu Ser Ala Ala Asn Ser Arg Ile Leu
                485                 490                 495

Asp Ala Asp Phe Ser Glu Thr Ala Lys Leu Ser Lys Ala Gln Val Leu
                500                 505                 510

Gln Gln Ala Gly Ile Ser Val Leu Ala Gln Ala Asn Ala Arg Pro Gln
        515                 520                 525

Gln Val Leu Ser Leu Leu Gln Gln Phe Met Ser Leu Leu Thr Glu Val
    530                 535                 540

Glu Thr Pro Thr Arg Ser Glu Trp Glu Cys Arg Cys Ser Asp Ser Ser
545                 550                 555                 560

Asp Met Ser Leu Leu Thr Glu Val Glu Thr Pro Thr Arg Ser Glu Trp
                565                 570                 575

Glu Cys Arg Cys Ser Asp Ser Ser Asp Met Ser Leu Leu Thr Glu Val
                580                 585                 590

Glu Thr Pro Thr Arg Ser Glu Trp Glu Cys Arg Cys Ser Asp Ser Ser
        595                 600                 605

Asp Met Ser Leu Leu Thr Glu Val Glu Thr Pro Thr Arg Ser Glu Trp
    610                 615                 620

Glu Cys Arg Cys Ser Asp Ser Ser Asp Ser Arg His His His His
625                 630                 635                 640

His His Ala Arg Lys Asp Glu Leu Lys Leu
                645                 650
```